United States Patent
Chen et al.

(10) Patent No.: US 8,609,864 B2
(45) Date of Patent: Dec. 17, 2013

(54) HYDROXAMIC ACID DERIVATIVES

(75) Inventors: Yu Chen, San Jose, CA (US); Yi Chen, San Jose, CA (US)

(73) Assignee: Purdue Pharmaceutical Products, L.P., Stamford, CT (US)

( * ) Notice: Subject to any disclaimer, the term of this patent is extended or adjusted under 35 U.S.C. 154(b) by 0 days.

(21) Appl. No.: 13/143,155

(22) PCT Filed: Jan. 7, 2010

(86) PCT No.: PCT/US2010/020373
§ 371 (c)(1),
(2), (4) Date: Jul. 1, 2011

(87) PCT Pub. No.: WO2010/085377
PCT Pub. Date: Jul. 29, 2010

(65) Prior Publication Data
US 2011/0269706 A1    Nov. 3, 2011

Related U.S. Application Data

(60) Provisional application No. 61/147,002, filed on Jan. 23, 2009, provisional application No. 61/156,496, filed on Feb. 28, 2009, provisional application No. 61/252,156, filed on Oct. 15, 2009, provisional application No. 61/252,652, filed on Oct. 17, 2009.

(51) Int. Cl.
*A61K 31/4184* (2006.01)
*C07D 235/16* (2006.01)

(52) U.S. Cl.
USPC .......... 548/309.7; 544/311; 544/317; 546/12; 556/137; 556/40; 558/48; 558/81; 514/394; 514/110; 514/507; 514/517; 514/43; 536/28.51; 562/621; 562/43

(58) Field of Classification Search
USPC ...................................................... 548/309.7
See application file for complete search history.

(56) References Cited

U.S. PATENT DOCUMENTS

| 6,087,367 A | 7/2000 | Breslow et al. |
| 2006/0159713 A1 | 7/2006 | Brittain et al. |

FOREIGN PATENT DOCUMENTS

| WO | WO-02/26696 A1 | 4/2002 |
| WO | 2005/097747 | 10/2005 |
| WO | WO-2007/134169 A2 | 11/2007 |
| WO | WO-2008/050125 A1 | 5/2008 |
| WO | 2009/100045 | 8/2009 |

OTHER PUBLICATIONS

Golub et al., Science, vol. 286, Oct. 15, 1999, pp. 531-537.*
Keating, Michael J., et al., "Bendamustine", Nature Reviews/Drug Discovery, vol. 7, Jun. 2008, pp. 473-474.
Wang, et al., "Toward Selective Histone Deacetylase Inhibitor Design: Homology Modeling, docking Studies, and Molecular Dynamics Simulations of Human Class I Histone Deacetylases", J. Med. Chem. 2005, vol. 48, pp. 6936-6947.
Xie, et al., "Quantative Structure-Activity Relationship Study of Histone Deacetylase Inhibitors", Curr. Med. Chem.—Anti-Cancer Agents, 2004, vol. 4, pp. 273-299.
Cai, et al., "Discovery of 7-(4-(3-Ethynylphenylamino)-7-methoxyquinazolin-6-yloxy)-N-hydroxyheptanamide (CUDC-101) as a Potent Multi-Acting HDAC, EGFR, and HER2 Inhibitor for the Treatment of Cancer", J. Med. Chem. 2010, 53, pp. 2000-2009.
Moradei, et al., "Histone Deacetylase Inhibitors: Latest Developments, Trends and Prospects", Curr. Med. Chem.—Anti-Cancer Agents, 2005, vol. 5, pp. 529-560.
Marks, "Discovery and development of SAHA as an anticancer agent", Oncogene, 2007, vol. 26, pp. 1351-1356.
Furumai et al. "Potent histone deacetylase inhibitors built from trichostatin A and cyclic tetrapeptide antibiotics including trapoxin," *PNAS*, 98(1):87-92 (2001).
Griffith et al., "A novel anti-cancer bifunctional platinum drug candidate with dual DNA binding and histone deacetylase inhibitory activity," *Chem. Commun.*, 44:6735-6737 (2009).
Griffith et al., "Novel platinum pyridinehydroxamic acid complexes," *Polyhedron*, 26(16):4697-4706 (2007).
Knauf, "Bendamustine in the treatment of chronic lymphocytic leukemia," *Exp. Rev. Anticancer Ther.*, 9(2):165-174 (2009).
Marmion et al., "Hydroxamic Acids—An Intriguing Family of Enzyme Inhibitors and Biomedical Ligands," *Eur. J. Inorg. Chem.*, 2004(15):3003-3016 (2004).
Miller et al., "Histone Deacetylase Inhibitors," *J. Med. Chem.*, 46(24):5097-5116 (2003).
Paris et al., "Histone Deacetylase Inhibitors: From Bench to Clinic," *J. Med. Chem.*, 51(6):1505-1529 (2008).

* cited by examiner

*Primary Examiner* — Laura L. Stockton
(74) *Attorney, Agent, or Firm* — McCarter & English, LLP; Elizabeth A. Hanley; Yu Lu

(57) ABSTRACT

The disclosure includes hydroxamic compounds of Formula I: (I) wherein P, Z, and m are defined herein. Also disclosed is a method for treating a neoplastic disease or an immune disease with these compounds.

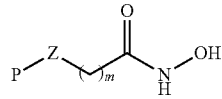

Formula I

16 Claims, No Drawings

HYDROXAMIC ACID DERIVATIVES

RELATED APPLICATIONS

This application is a National Phase application of international application No. PCT/US2010/020373 filed Jan. 7, 2010, which claims priority to and the benefit of U.S. Provisional Application No. 61/147,002, filed on Jan. 23, 2009, U.S. Provisional Application No. 61/156,496, filed on Feb. 28, 2009, U.S. Provisional Application No. 61/252,156, filed on Oct. 15, 2009, and U.S. Provisional Application No. 61/252,652 filed on Oct. 17, 2009. The entire teachings of the above applications are incorporated herein by reference.

BACKGROUND

Cancer is one of the most life threatening diseases in which cells in a part of the body experience out-of-control growth. According to the latest data from American Cancer Society, cancer is the second leading cause of death in the United States (second only to heart disease) and claimed more than 550,000 lives in 2007. In fact, it is estimated that 50% of all men and 33% of all women living in the United States will develop some type of cancer in their lifetime. Therefore cancer constitutes a major public health burden and represents a significant cost in the United States. For decades, surgery, chemotherapy, and radiation were the established treatments for various cancers. Patients usually receive a combination of these treatments depending upon the type and extent of their disease. But the chemotherapy is most important option for cancer patient when the surgery treatment is impossible.

DNA alkylating agents (e.g. nitrogen mustards, platinum-based complex) were among the first chemotherapeutic agents rationally applied to the treatment of cancer. DNA alkylating agents generally exert cytotoxic activity by forming DNA adducts or crosslinks between DNA strands under conditions present in cells, directly interfering with the reproductive cycle of the cell. Mechlorethamine, an analogue of mustard gas and derived from chemical warfare research during World War II, has been used in the cancer chemotherapy for over 60 years. Other approved nitrogen mustards for cancer treatment include the Chlorambucil, Melphalan, Cyclophosphamide, Ifosfamide, Bendamustine, Estramustine, and Uramustine. Some novel nitrogen mustards, such as TH-302 and PR-104, are still in human clinical trials. Another class of widely used DNA alkylating agents is the platinum-based compounds including Cisplatin, Carboplatin, Oxaliplatin, Satraplatin, Picoplatin, Nedaplatin, Lobaplatin, and Heptaplatin (Markus Galanski, et. al., *Current Medicinal Chemistry*, 2005, 12, 2075-2094).

For example, the DNA alkylating agent Bendamustine, first synthesized in 1963, consists of an alkylating nitrogen mustard group and a purine-like benzimidazol moiety (Barman Balfour J A, et al, *Drugs* 2001, 61: 631-640). Bendamustine has been shown to have substantial activity against low-grade lymphomas (Herold M, et al., *Blood*, 1999, 94, Suppl 1: 262a), multiple myelomas (Poenisch W, et al., *Blood* 2000, 96, Suppl 1: 759a), and several solid tumors (Kollmannsberger C, et al., *Anticancer Drugs* 2000, 11: 535-539). It was also reported that bendamustine effectively induces apoptosis in lymphoma cells (Chow K U, et al., *Haematologica,* 2001, 86: 485-493). On March 2008, the FDA granted approval to market bendamustine for the treatment of chronic lymphocytic leukemia (CLL). On October 2008, the FDA granted further approval to market bendamustine for the treatment of indolent B-cell non-Hodgkin's lymphoma (NHL) that has progressed during or within six months of treatment with rituximab or a rituximab-containing regimen. Currently bendamustine is in clinical trial for a variety of cancer indications, such as leukemia, lymphoma, small cell lung cancer, multiple myeloma, MDS, ovarian cancer, breast cancer, and brain tumor.

Cisplatin is another widely used DNA alkylating agent for cancer treatment. The tumor-inhibiting properties of cisplatin were first reported in 1969 by Barnett Rosenberg four years after his pioneering work performed with the original intention of investigating the influence of an electric field on bacterial growth and 125 years after the first synthesis of cisplatin by Michele Peyrone. Today, cisplatin has become one of the most successful anticancer drugs and been used in nearly 50% of all tumor chemotherapies. Although the first-generation cisplatin has a wide spectrum of anticancer activity, it does have significant side toxicity, and its clinical use can also be limited by the existence or development of resistance. In an attempt to overcome these problems, several thousand platinum-based compounds have been synthesized and screened. Substitution of the two ammine moieties of cisplatin with the diaminocyclohexane (DACH) group led to compounds that had good antitumour activity and lack of cross-resistance with cisplatin, but which were poorly water-soluble, limiting their potential for clinical development. Further modifications aimed at improving water solubility by replacing the chloride moieties of cisplatin resulted in the discovery of oxaliplatin. (Joanne Graham et al., *Nature Reviews-Drug Discovery,* 2004, 3, 11-12). Oxaliplatin has a broad spectrum of anticancer activity and a better safety profile than cisplatin. It also shows a lack of cross-resistance with cisplatin or carboplatin (another widely used platinum-based compound), which is thought to result from the chemical and steric characteristics of the DACH-platinum-DNA adducts. Observations, in contrast to cisplatin and carboplatin, oxaliplatin was active against several colon cancer cell lines in the National Cancer Institute's Anticancer Drug Screen Panel provided impetus for its clinical evaluation in this indication. In 2002, Oxaliplatin became the first platinum-based anticancer drug to be approved by US FDA for the treatment of colorectal cancer, a major cause of cancer deaths worldwide.

Antimetabolites are another class of extensively used chemotherapy for cancer treatment. Antimetabolite means a substance which is structurally similar to a critical natural metabolite in a biochemical pathway leading to DNA or RNA synthesis, but acts to inhibit the completion of said biochemical pathway. More specifically, antimetabilites typically function by (1) competing with metabolites for the catalytic or regulatory site of a key enzyme in DNA or RNA synthesis, or (2) substitute for a metabolite that is normally incorporated into DNA or RNA, and thereby producing a DNA or RNA that can't support replication. Major categories of antimetabolites include (1) folic acid analogs, which are inhibitors of dihydrofolate reductase (DHFR); (2) purine analogues, which mimic the natural purines (adenine or guanine) but are structurally different so they competitively or irreversibly inhibit nuclear processing of DNA or RNA; and (3) pyrimidine analogues, which mimic the natural pyrimidines (cytosine, thymidine, and uracil) but are structurally different so they competitively or irreversibly inhibit nuclear processing of DNA of RNA. Typical antimetabolite drugs include antifolate (such as Aminopterin, Methotrexate, Pemetrexed, and Raltitrexed), Purine analogues (such as Cladribine, Clofarabine, Fludarabine, Mercaptopurine, Pentostatin, and Thioguanine), and Pyrimidine analogues (such as Cytarabine, Decitabine, Fluorouracil, Capecitabine, Floxuridine, Gemcitabine, Enocitabine, and Sapacitabine). Some of these antimetabolites, for example, Methotrexate, Fluorouracil, and Gemcitabine, are the cornerstone of modern chemotherapy.

For example, Fluorouracil (5-FU) is an antimetabolite and has been in use as chemotherapy against cancer for about 40 years. As a pyrimidine analogue, it is transformed inside the cell into different cytotoxic metabolites which are then incorporated into DNA and RNA, finally inducing cell cycle arrest and apoptosis by inhibiting the cell's ability to synthesize DNA. Like many anti-cancer drugs, 5-FU's effects are felt system wide but fall most heavily upon rapidly dividing cells that make heavy use of their nucleotide synthesis machinery, such as cancer cells. Some of the principal use of 5-FU is in colorectal cancer and breast cancer, in which it has been the established form of chemotherapy for decades.

Gemcitabine is another well-known antimetabolite and chemically a nucleoside analog in which the hydrogen atoms on the 2' carbons of deoxycytidine are replaced by fluorine atoms. As with fluorouracil and other analogues of pyrimidines, the drug replaces one of the building blocks of nucleic acids during DNA replication. The process arrests tumor growth, as new nucleosides cannot be attached to the "faulty" nucleoside, resulting in apoptosis. Gemcitabine is used in various carcinomas: non-small cell lung cancer, pancreatic cancer, bladder cancer and breast cancer.

The following table shows some well known examples of DNA alkylating agents and antimetabolites drugs for cancer treatment. Although these conventional chemotherapeutic drugs have made a significant contribution to cancer treatment, the dose-limiting toxicities and drug resistance remain significant hurdles in the use of these drugs. Therefore, there is a strong need for continuous search in this field of art for the novel derivatives of these drugs with improved anti-cancer activities.

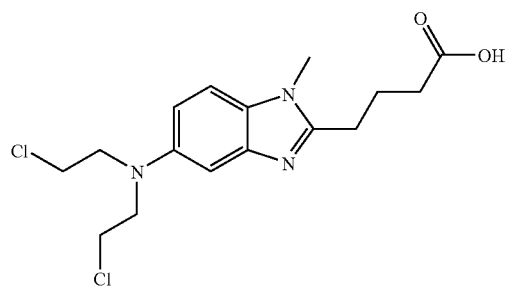

Bendamustine

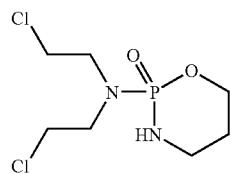

Cyclophosphamide

-continued

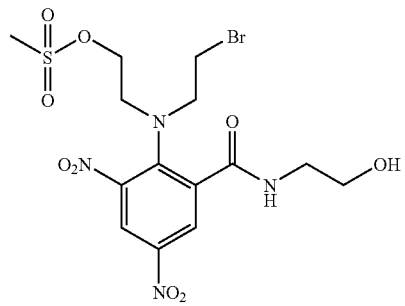

PR-104

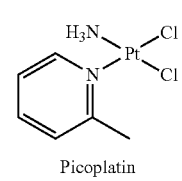

Picoplatin

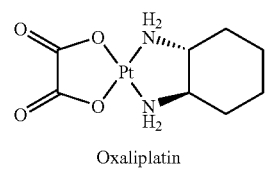

Oxaliplatin

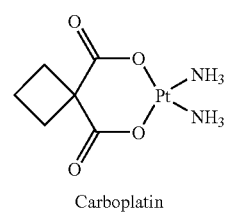

Carboplatin

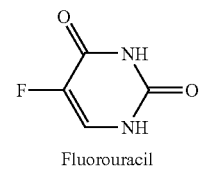

Fluorouracil

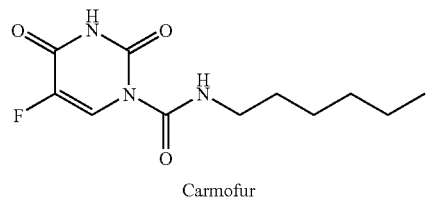 [SMILES: CCCCCCNC(=O)n1cc(F)c(=O)[nH]c1=O]

Carmofur

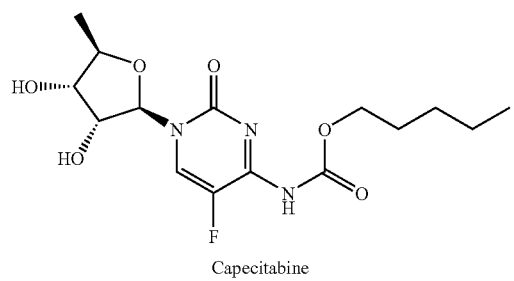 [SMILES: CCCCCOC(=O)Nc1nc(=O)n([C@@H]2O[C@H](C)[C@@H](O)[C@H]2O)cc1F]

Capecitabine

-continued

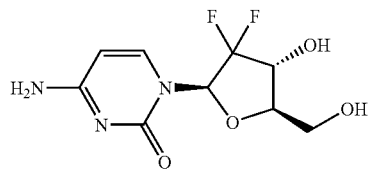
Gemcitabine

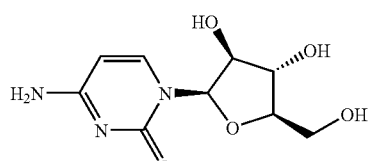
Cytarabine

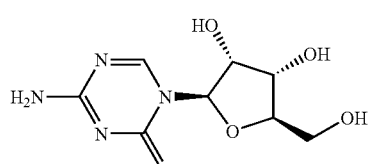
Azacitidine

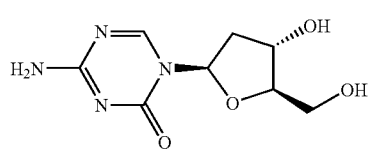
Decitabine

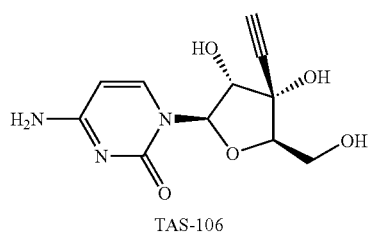 [SMILES: C#C[C@@]1(O)[C@@H](CO)O[C@@H](n2ccc(N)nc2=O)[C@@H]1O]
TAS-106

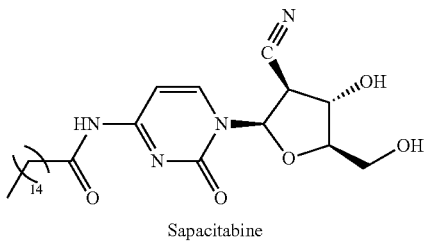
Sapacitabine

SUMMARY

The present invention relates to a novel class of hydroxamic acid derivatives of the conventional chemotherapeutical drugs such as DNA alkylating drugs and antimetabolites. This invention is based on the unexpected discovery that certain hydroxamic derivatives show enhanced antitumor activities when compared to the activities of the parental chemotherapeutical drug. Thus, the compounds of the present invention are useful in treating a patient having a tumor. The compounds of the invention may also useful in the prevention and treatment of an immune disease.

In one aspect, this invention relates to a hydroxamic compound of Formula I:

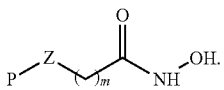

Formula I

In Formula I, Z is deleted, $C(R_aR_b)$, O, S, C(O), $N(R_a)$, $SO_2$, OC(O), C(O)O, $OSO_2$, $S(O_2)O$, C(O)S, SC(O), C(O)C(O), $C(O)N(R_a)$, $N(R_a)C(O)$, $S(O_2)N(R_a)$, $N(R_a)S(O_2)$, OC(O)N $(R_a)$, $N(R_a)C(O)O$, $N(R_a)C(O)S$, or $N(R_a)C(O)N(R_b)$, in which each of $R_a$ and $R_b$, independently, is H, alkyl, alkenyl, or alkynyl; m is 5, 6, 7, 8, 9, 10, 11, 12, 13, 14, 15, or 16; and P is a platinum-containing moiety,

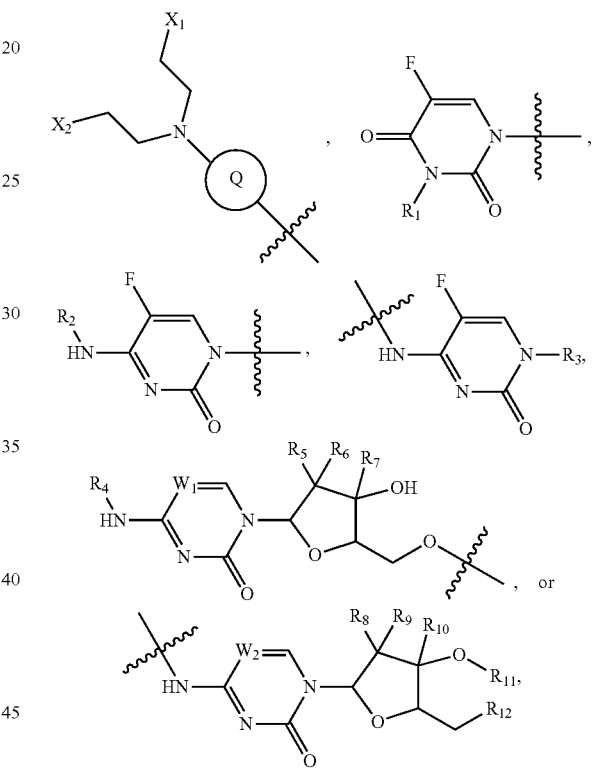

in which each of $X_1$ and $X_2$ independently, is halo or $OSO_2R_c$, in which $R_c$ is alkyl, alkenyl, or alkynyl; Q is a cycloalkyl, heterocycloalkyl, cycloalkenyl, heterocycloalkenyl, aryl, or heteroaryl, each of which, independently, is optionally substituted with alkyl, alkenyl, alkynyl, cycloalkyl, heterocycloalkyl, cycloalkenyl, heterocycloalkenyl, aryl, heteroaryl, halo, nitro, oxo, —C=NH, cyano, $OR_d$, $OC(O)R_d$, OC(O) $OR_d$, $OC(O)SR_d$, $SR_d$, $C(O)R_d$, $C(O)OR_d$, $C(O)SR_d$, C(O) $NR_eR_f$, $SOR_d$, $SO_2R_d$, $NR_eR_f$, or $N(R_e)C(O)R_f$, in which each of $R_d$, $R_e$, and $R_f$ independently, is H, alkyl, alkenyl, alkynyl, cycloalkyl, heterocycloalkyl, aryl, heteroaryl, halo, cyano, nitro, hydroxy, or alkoxy; each of $W_1$ and $W_2$ is $CR_g$ or N in which $R_g$ is H, halo, alkyl, alkenyl, or alkynyl; and each of $R_1$, $R_2$, $R_3$, $R_4$, $R_5$, $R_6$, $R_7$, $R_8$, $R_9$, $R_{10}$, $R_{11}$, and $R_{12}$, independently, is H, alkyl, alkenyl, alkynyl, cycloalkyl, heterocycloalkyl, cycloalkenyl, heterocycloalkenyl, aryl, heteroaryl, halo, cyano, nitro, oxo, —C=NH, $OR_d$, $OC(O)R_d$, OC(O) $OR_d$, $OC(O)SR_d$, $SR_d$, $C(O)R_d$, $C(O)OR_d$, $C(O)SR_d$, C(O) $NR_eR_f$, $SOR_d$, $SO_2R_d$, $NR_eR_f$ or $N(R_e)C(O)R_f$.

One subset of the above-described compounds includes those in which Z is deleted, $CH_2$, O, CO, NH, $SO_2$, OC(O), C(O)O, C(O)S, NHC(O), C(O)NH, OC(O)NH, NHC(O)O, or NHC(O)S; m is 5, 6, 7, or 8; In these compounds, P can be

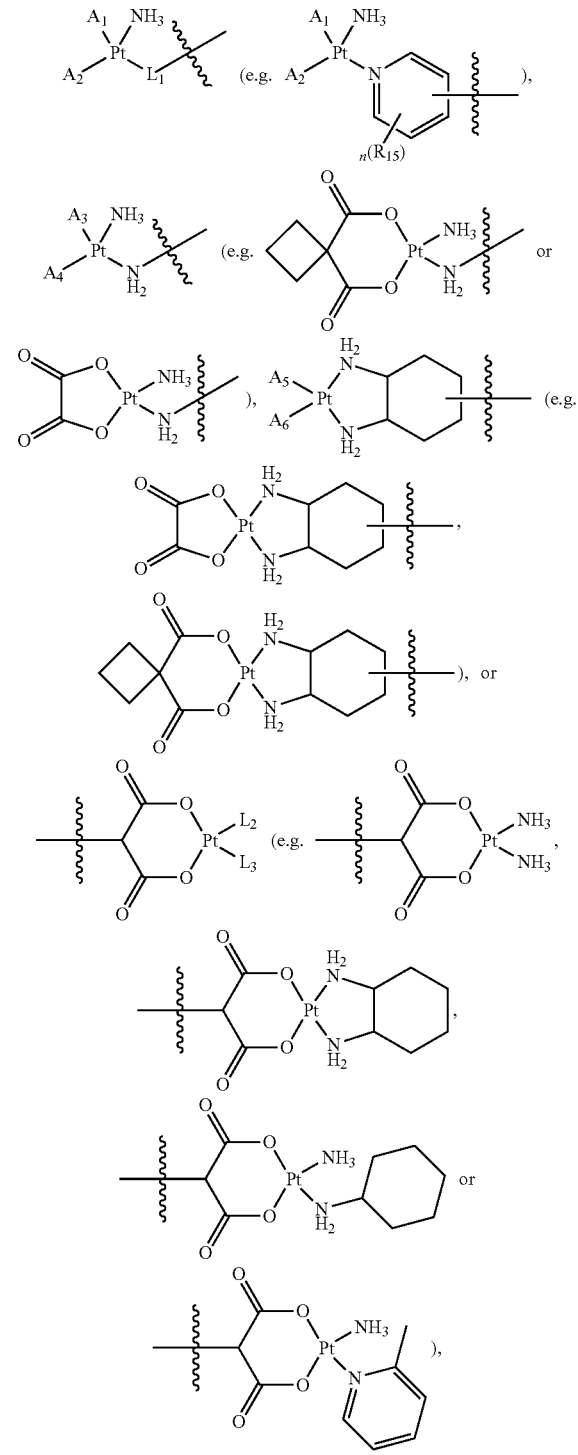

in which $L_1$ is a cyclic amine; each of $L_2$ and $L_3$ independently, is $NHR_{13}R_{14}$, $L_1$, or $L_2$ and $L_3$ together form a bidentate amine, in which each of $R_{13}$ and $R_{14}$, independently is H, alkyl, alkenyl, alkynyl, cycloalkyl, heterocycloalkyl, cycloalkenyl, heterocycloalkenyl, aryl, or heteroaryl, each of which, independently, is optionally substituted with alkyl, alkenyl, alkynyl, cycloalkyl, heterocycloalkyl, cycloalkenyl, heterocycloalkenyl, aryl, heteroaryl, halo, nitro, oxo, —C=NH, cyano, $OR_d$, $OC(O)R_d$, $OC(O)OR_d$, $OC(O)SR_d$, $SR_d$, $C(O)R_d$, $C(O)OR_d$, $C(O)SR_d$, $C(O)NR_eR_f$, $SOR_d$, $SO_2R_d$, $NR_eR_f$, or $N(R_e)C(O)R_f$; each $R_{15}$, independently, is H, alkyl, alkenyl, alkynyl, cycloalkyl, heterocycloalkyl, cycloalkenyl, heterocycloalkenyl, aryl, heteroaryl, halo, cyano, nitro, oxo, —C=NH, $OR_d$, $OC(O)R_d$, $OC(O)OR_d$, $OC(O)SR_d$, $SR_d$, $C(O)R_d$, $C(O)OR_d$, $C(O)SR_d$, $C(O)NR_eR_f$, $SOR_d$, $SO_2R_d$, $NR_eR_f$, or $N(R_e)C(O)R_f$; n is 0, 1, 2, or 3; and each of $A_1$, $A_2$, $A_3$, $A_4$, $A_5$, and $A_6$, independently, is halo, hydroxy, carboxylate, alkoxy, or $A_1$ and $A_2$, $A_3$ and $A_4$, or $A_5$ and $A_6$ together form a bidentate carboxylate, alkoxycarboxylate, phosphonocarboxylate, diphosphonate, or sulphate. In these compounds, P can also be

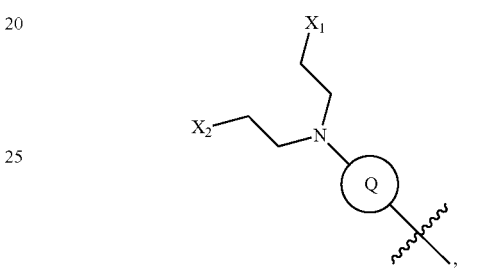

Q being an aryl or heteroaryl

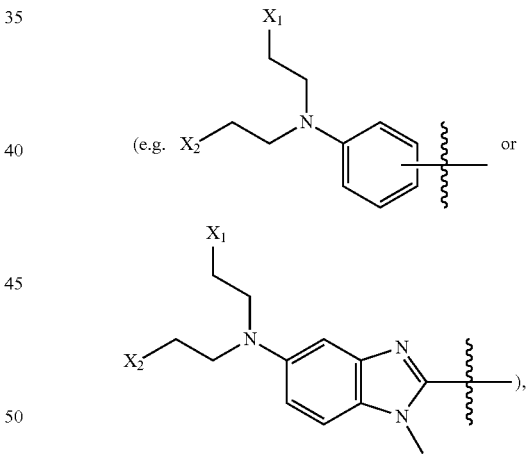

an aryl or heteroaryl substituted with at least one nitro group

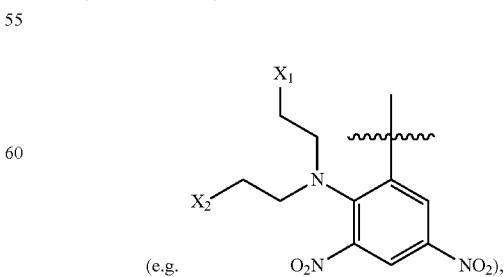

or a phosphorus-containing heterocycloalkyl

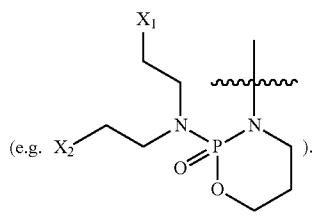

Alternatively, in these compounds, P can be

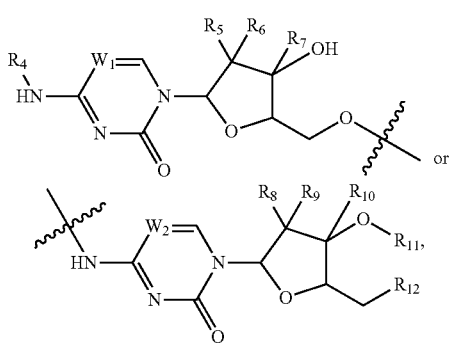

in which $W_1$ can be CH or N, and each of $R_4$, $R_5$, $R_6$, and $R_7$, independently, can be H, alkyl, alkenyl, alkynyl, $C(O)R_d$, $C(O)OR_d$, $C(O)SR_d$, halo, hydroxy, or cyano; $W_2$ can be CH, CF, or N, and each of $R_8$, $R_9$, $R_{10}$, $R_{11}$, and $R_{12}$, independently, can be H, alkyl, alkenyl, alkynyl, halo, hydroxy, cyano, $OR_d$, $OC(O)R_d$, $OC(O)OR_d$, $OC(O)SR_d$, $C(O)R_d$, $C(O)OR_d$, or $C(O)SR_d$.

The compounds described above include the compounds themselves, as well as their salts, their solvates, and their prodrugs, if applicable. A salt, for example, can be formed between an anion and a positively charged group (e.g., amino) on a hydroxamic compound of this invention. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a hydroxamic compound of this invention. Suitable cations include sodium ion, potassium ion, magnesium ion, calcium ion, and an ammonium cation such as tetramethylammonium ion. The hydroxamic compounds of this invention also include those salts containing quaternary nitrogen atoms. Examples of prodrugs include esters and other pharmaceutically acceptable derivatives, which, upon administration to a subject, are capable of providing active hydroxamic compounds described herein.

Compounds of the invention may contain one or more asymmetric carbon atoms. Accordingly, the compounds may exist as diastereomers, enantiomers or mixtures thereof. Each of the asymmetric carbon atoms may be in the R or S configuration and both of these configurations are within the scope of the invention.

Also within the scope of this invention is a pharmaceutical composition containing one or more of the above-described hydroxamic compounds for use in treating a neoplastic or immune disorder, as well as this therapeutic use and use of the compounds for the manufacture of a medicament for treating the disorder.

The invention encompasses any pharmaceutically acceptable salts of any one of the above-described hydroxamic compounds. A modified compound of any one of such hydroxamic compounds including a modification having an improved (e.g., enhanced, greater) pharmaceutical solubility, stability, and/or bioavailability as compared to the unmodified compound is also contemplated.

This invention also relates to a method of treating a neoplastic disorder (e.g., cancer, myelodysplastic syndrome, or myeloproliferative disease) by administering to a subject in need thereof an effective amount of one or more of the hydroxamic compounds, compositions, and/or salts and modifications thereof described above.

Furthermore, this invention relates to a method of treating an immune disease (e.g., rheumatoid arthritis and multiple sclerosis) by administering to a subject in need thereof an effective amount of one or more of the hydroxamic compounds, compositions, and/or salts and modifications thereof described above.

The details of one or more embodiments of the invention are set forth in the description below. Other features, objects, and advantages of the invention will be apparent from the description and from the claims.

DETAILED DESCRIPTION

Exemplary compounds described herein include, but are not limited to, the following:

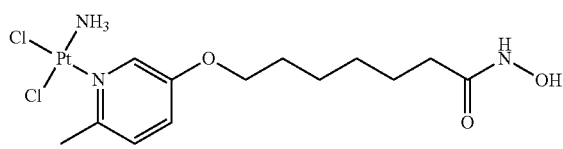

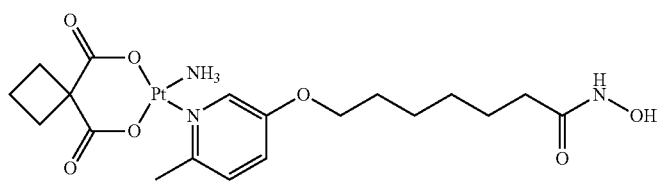

-continued
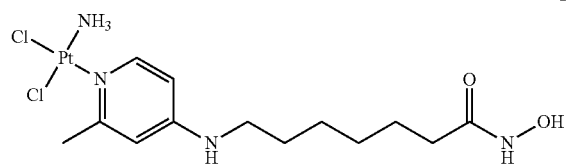
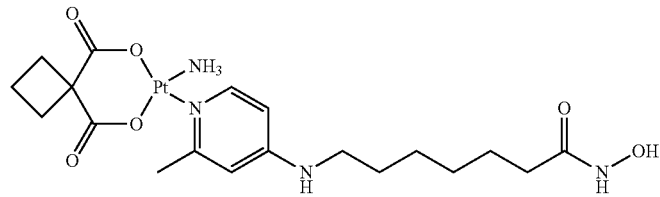
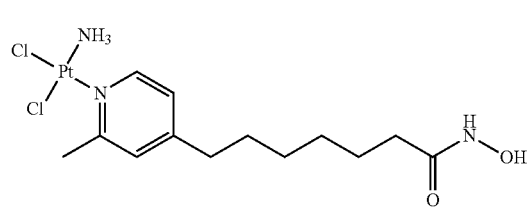
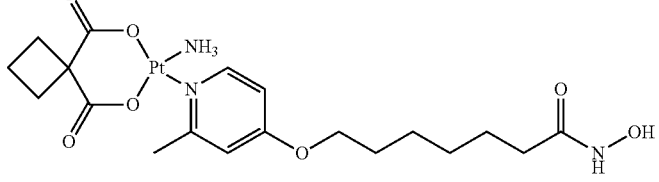
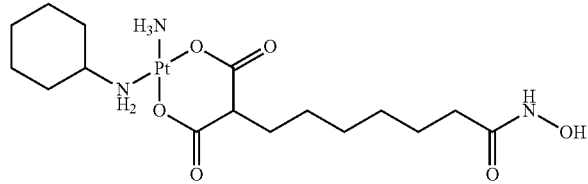
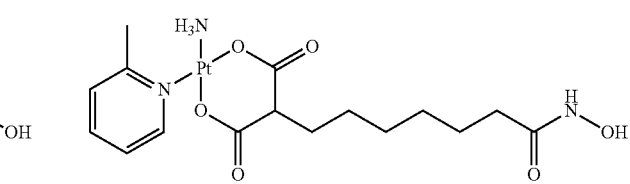
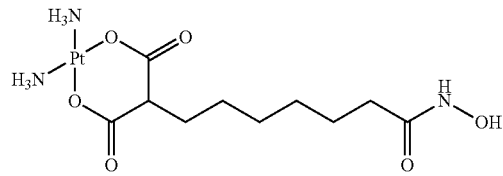
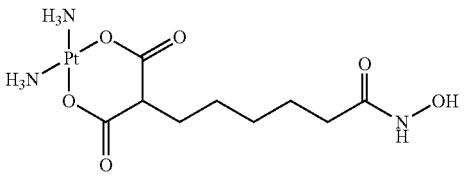
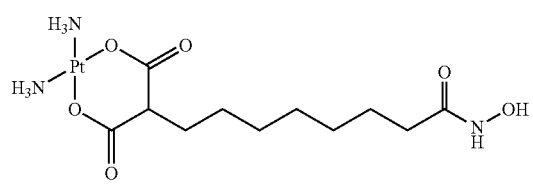
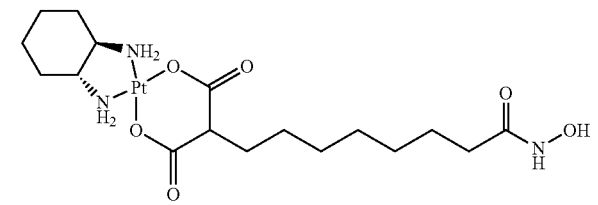
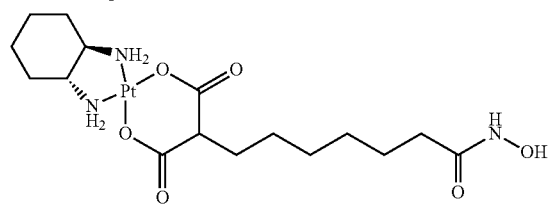
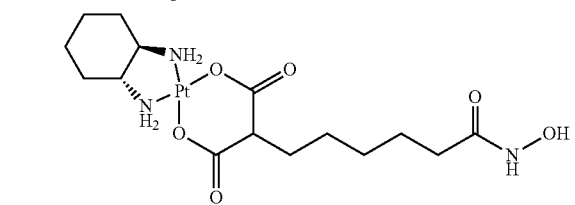
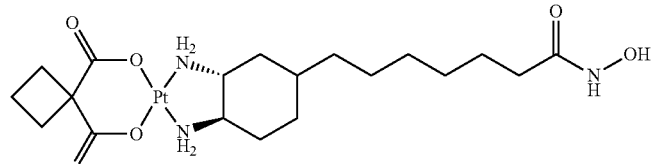
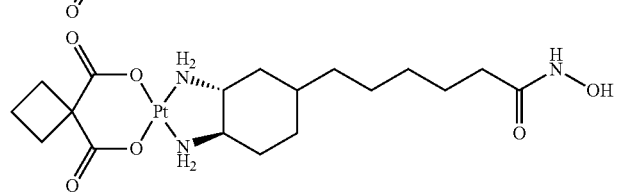

-continued
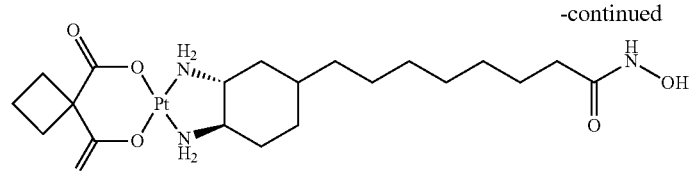
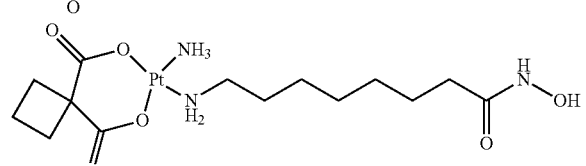
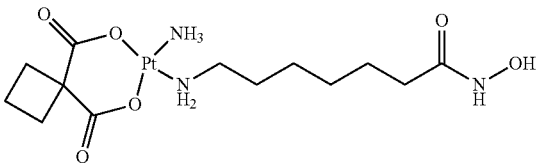
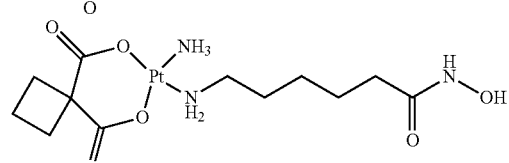
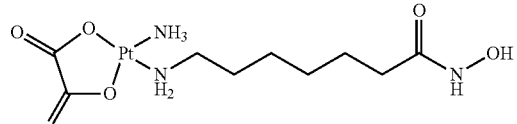
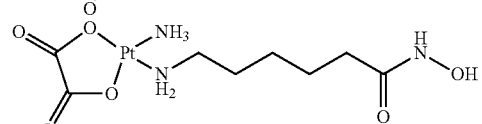
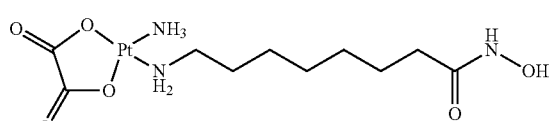
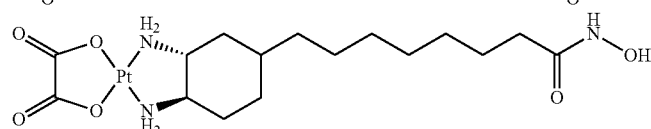
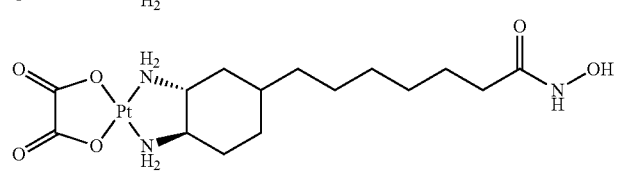
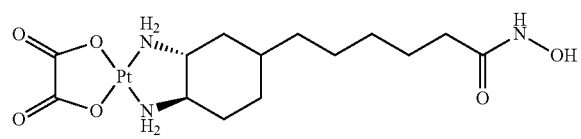
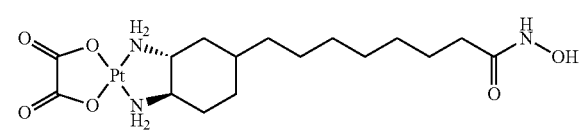
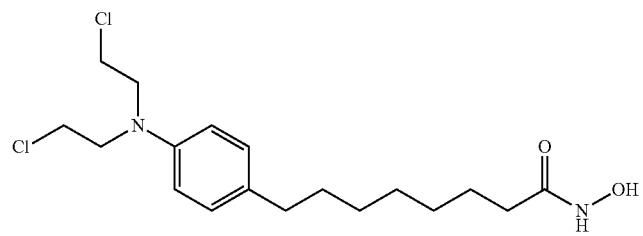
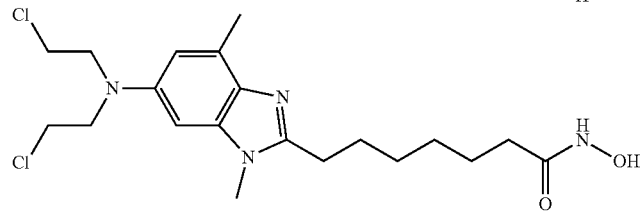

-continued
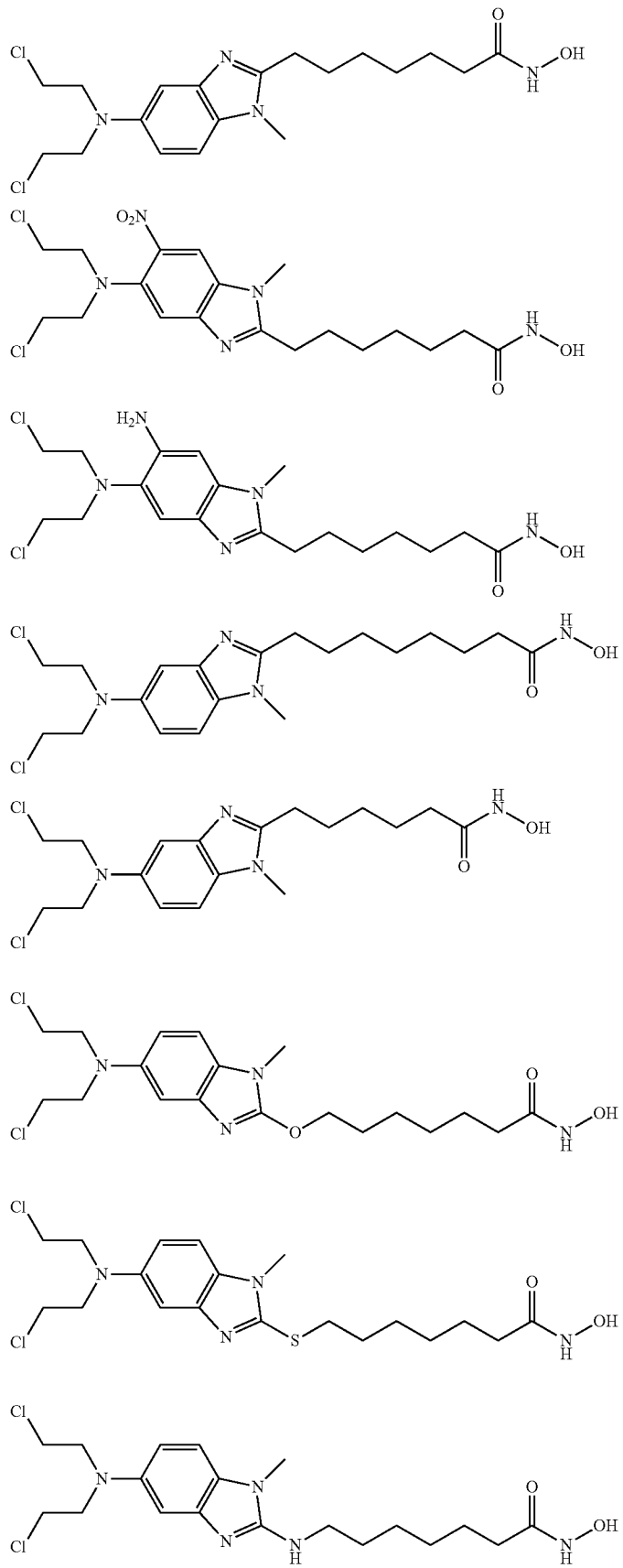

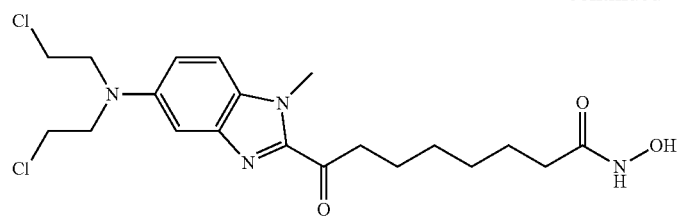
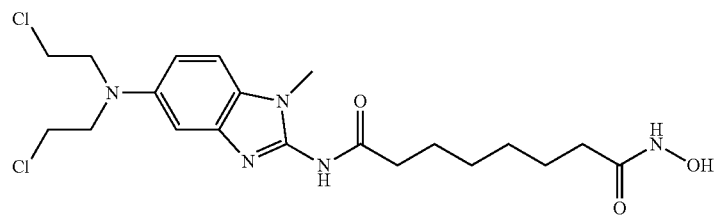
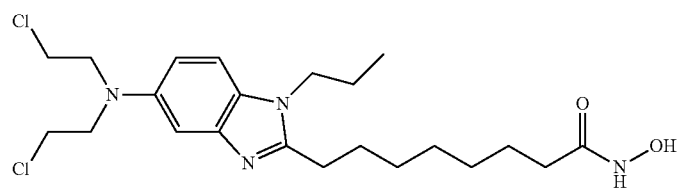
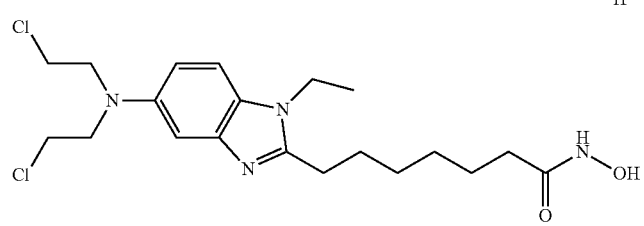
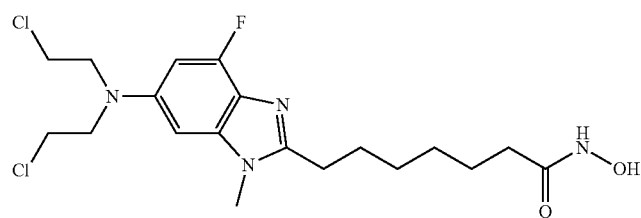
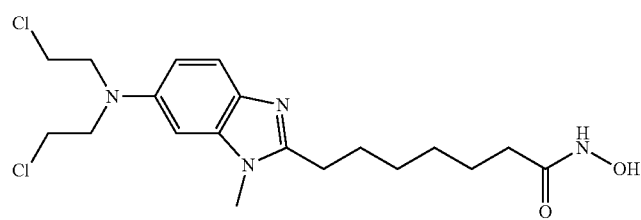
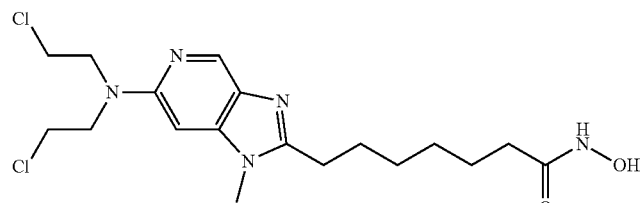
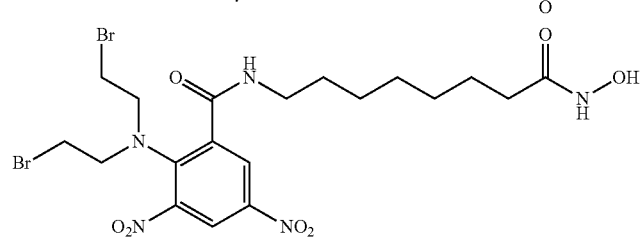

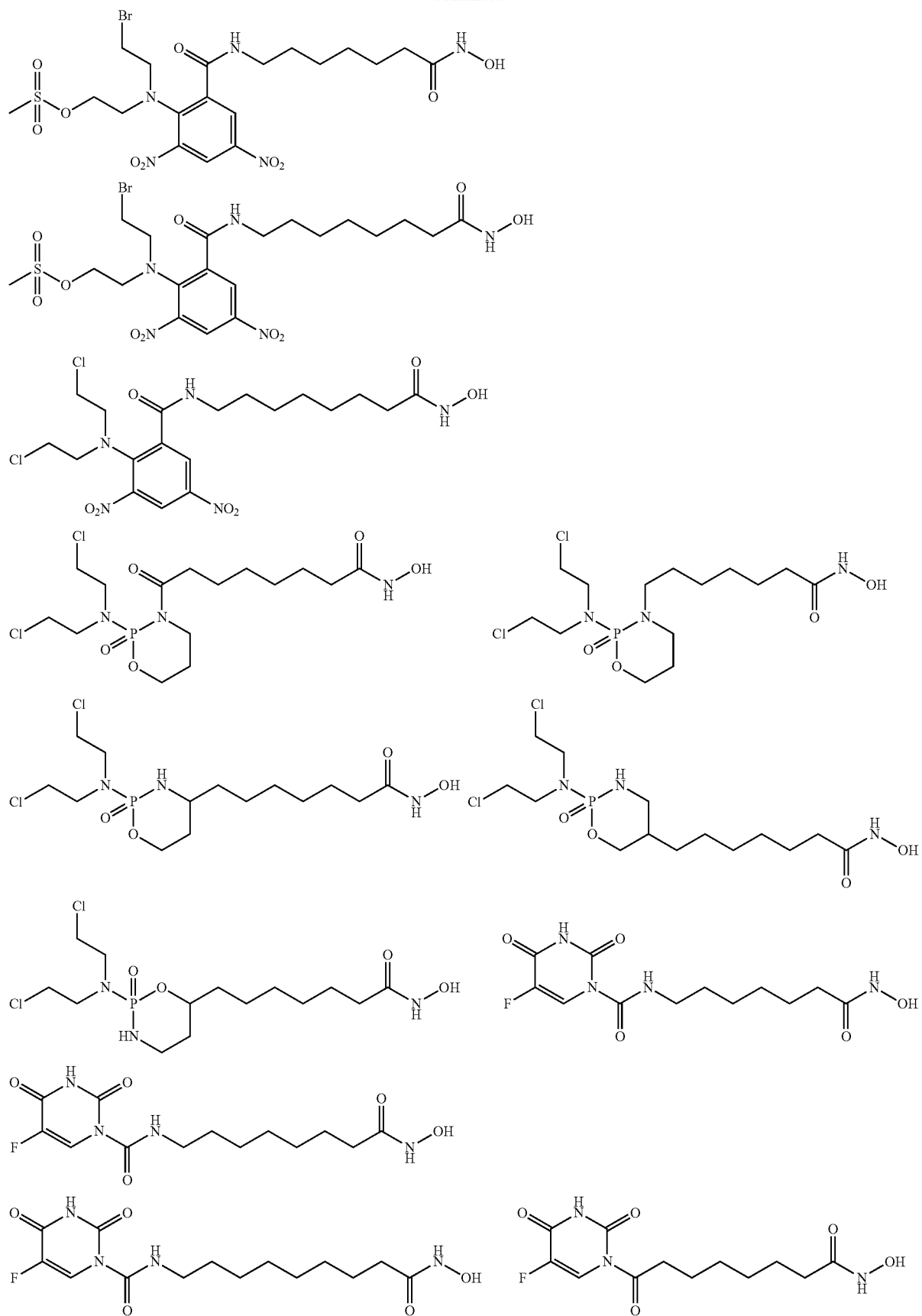

21
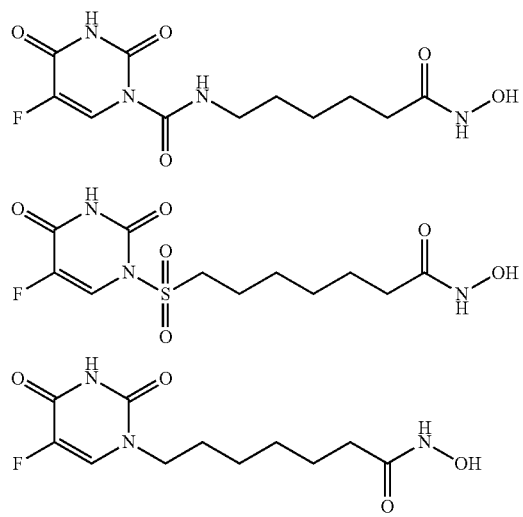
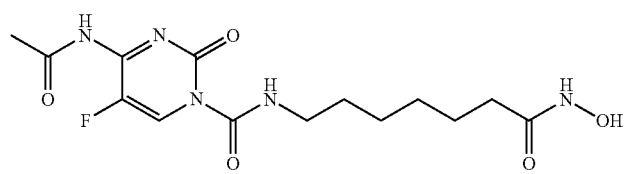
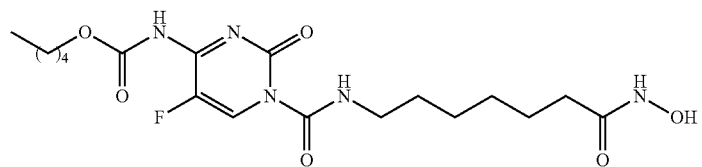
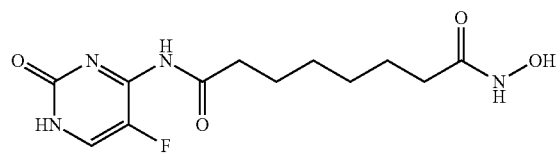
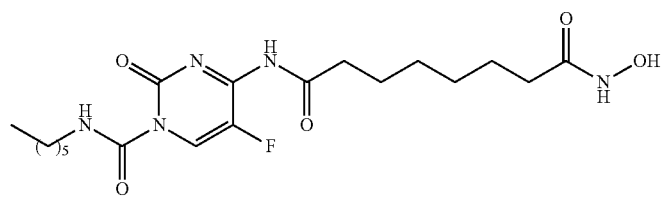
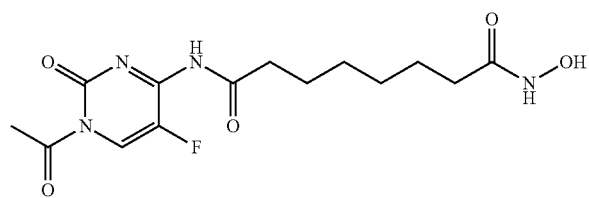
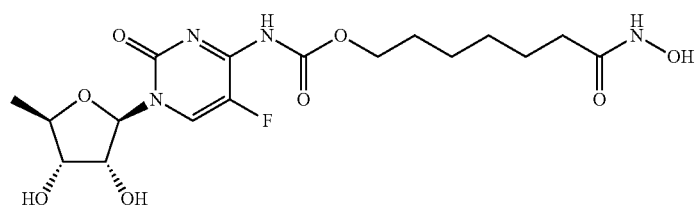
22
-continued
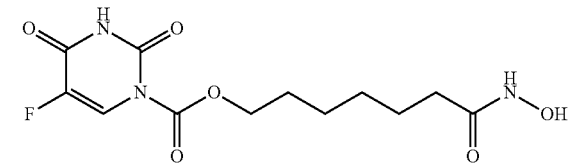
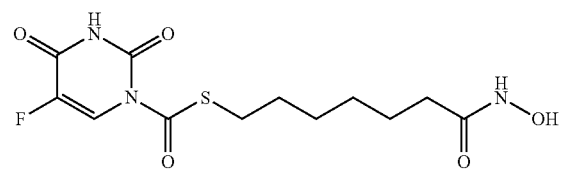
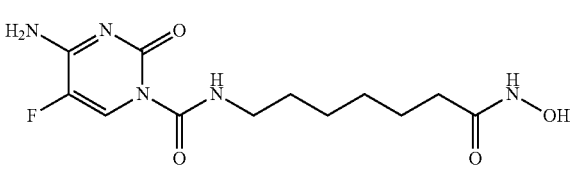

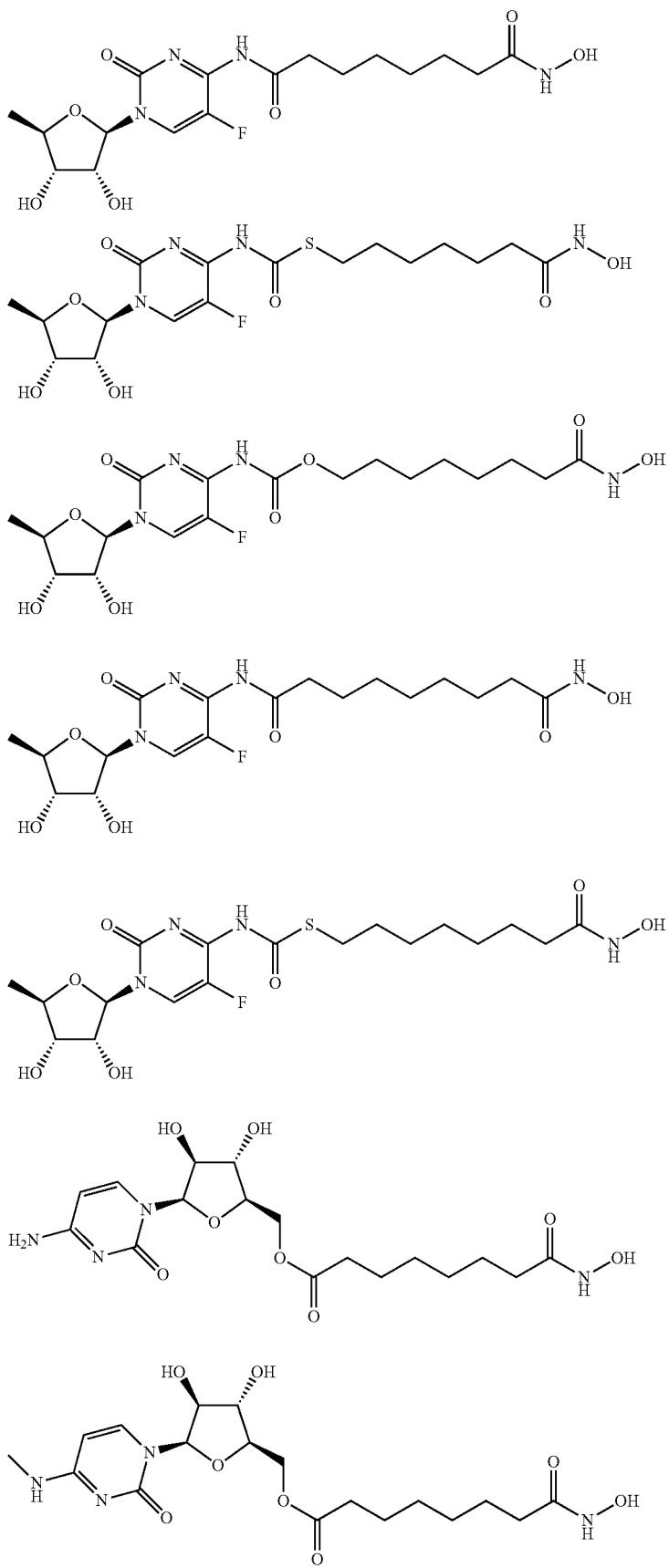

-continued
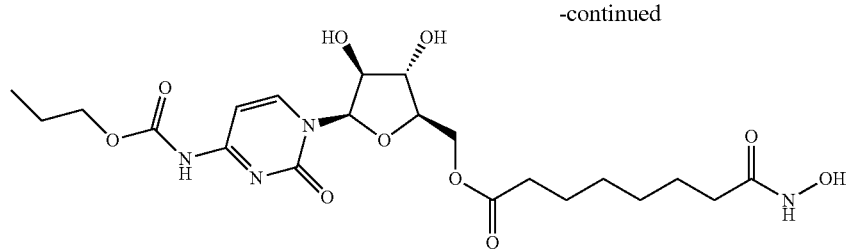
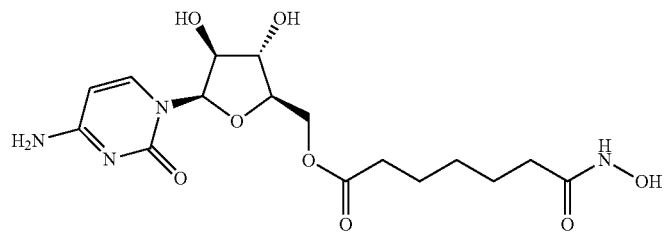
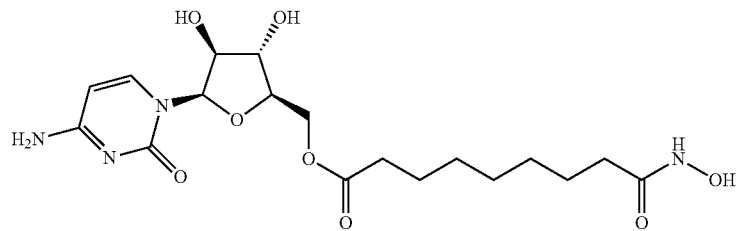
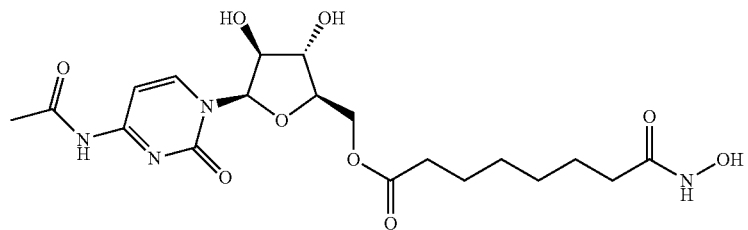
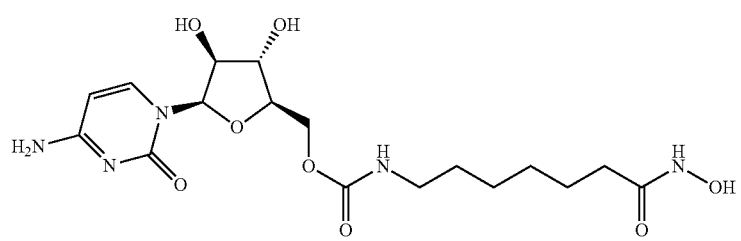
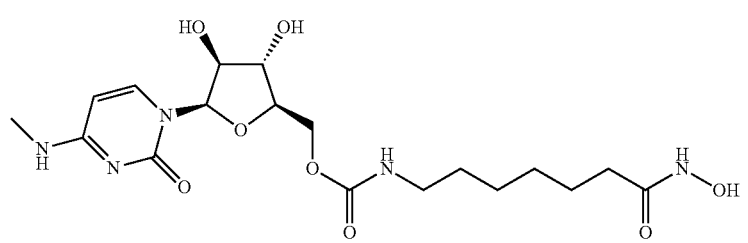
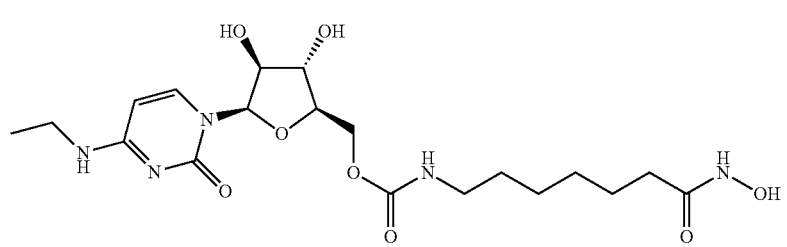

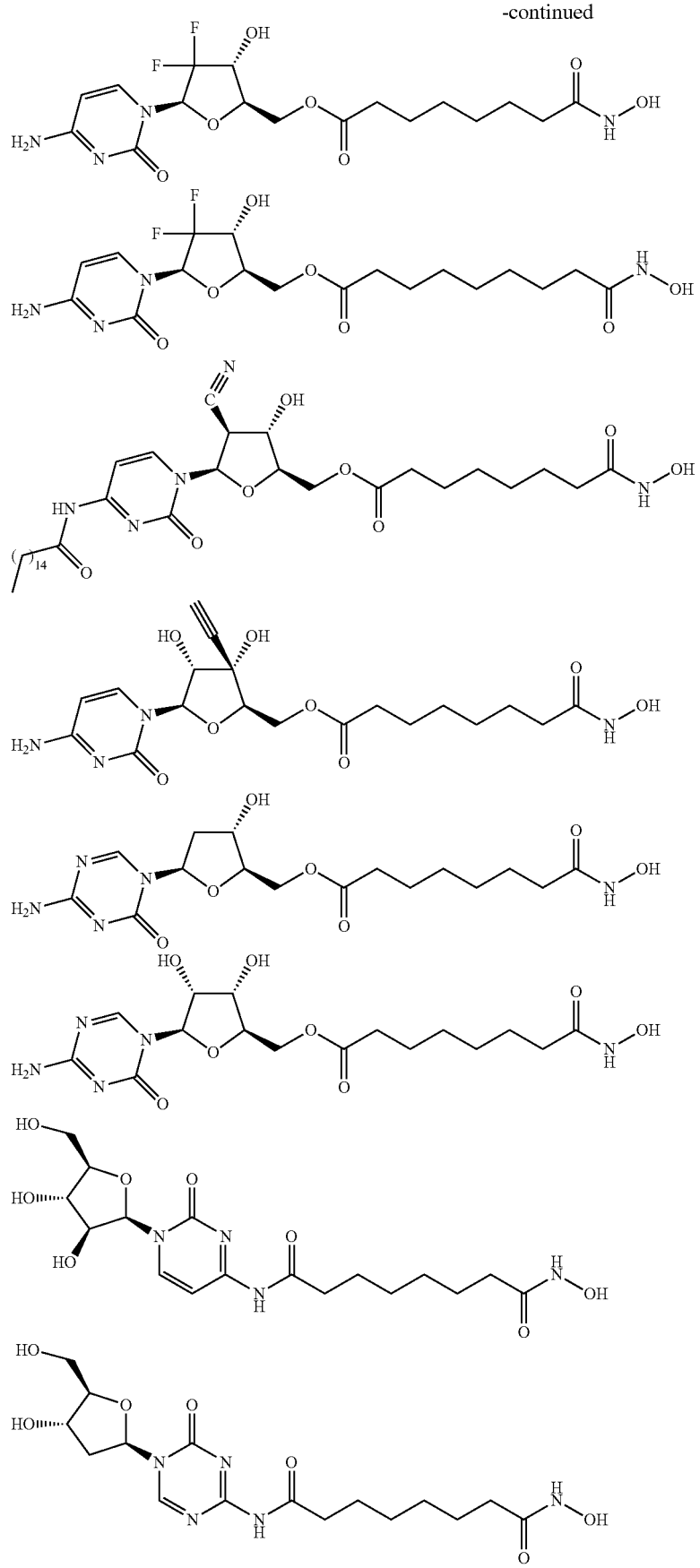

-continued

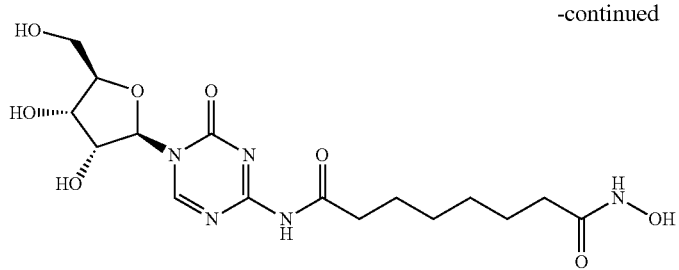

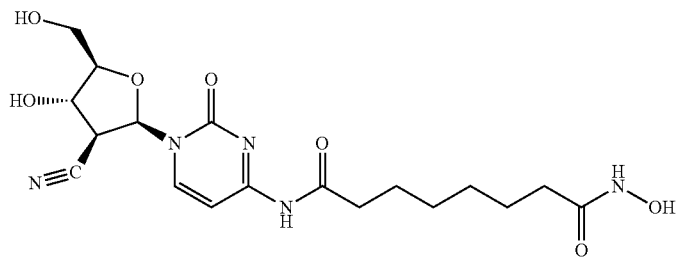

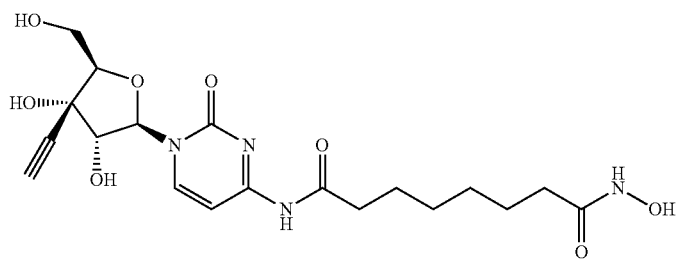

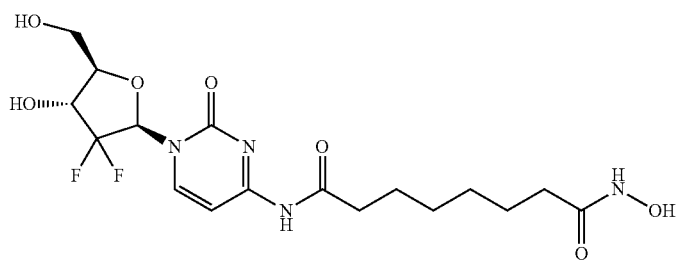

Compounds of the invention can be prepared using standard organic synthetic techniques from commercially available starting materials and reagents. It will be appreciated that synthetic procedures employed in the preparation of compounds of the invention will depend on the particular substituents present in a compound and that various protection and deprotection procedures may be required as is standard in organic synthesis.

As an example, compounds of Formula I in which P are

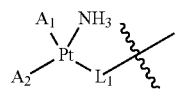

can be prepared according to general Scheme 1 below. $L_1$, $A_1$, $A_2$, m, and Z in general Scheme 1 are the same as those described in the Summary section above.

Scheme 1

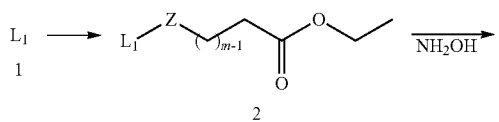

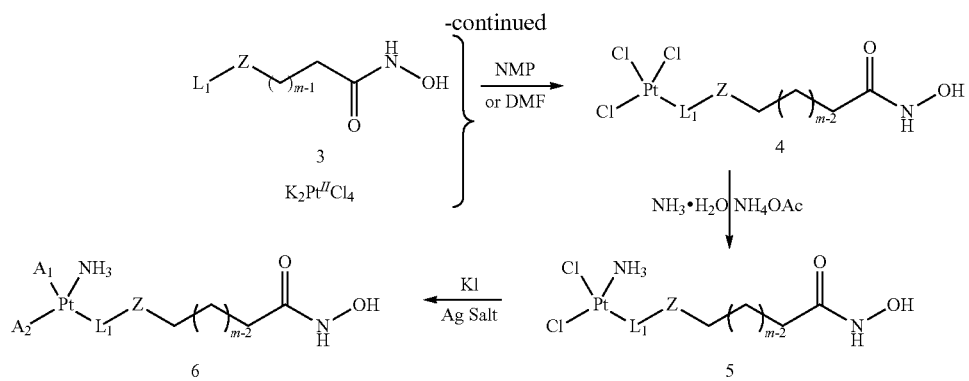

The cyclic amide $L_1$ (1) is coupled to appropriate ester to give intermediate (2) which will subsequently undergo a hydroxylamination reaction in $NH_2OH$ to afford hydroxamic acid ligand (3). The ligand (3) will react with $K_2PtCl_4$ in an aprotic solvent such as NMP or DMF to give intermediate (4). Intermediate (4) will be converted to intermediate (5) in ammonium hydroxide solution. Finally the intermediate (5) can react with an appropriate silver salt such as dicarboxylic acid salt to give the target product (6).

Similar compounds of Formula I in which P are

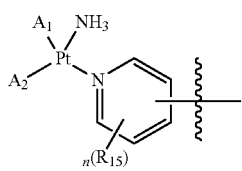

can be prepared according to general Scheme 2 below. $R_{15}$, n, $A_1$, $A_2$, m, and Z in general Scheme 2 are the same as those described in the Summary section above.

The cyclic amide (1) is coupled to appropriate ester to give intermediate (2) which will subsequently undergo a hydroxylamination reaction in $NH_2OH$ to afford hydroxamic acid ligand (3). The ligand (3) will react with $K_2PtCl_4$ in an aprotic solvent such as NMP or DMF to give intermediate (4). Intermediate (4) will be converted to intermediate (5) in ammonium hydroxide solution. Finally the intermediate (5) can react with an appropriate silver salt such as dicarboxylic acid salt to give the target product (6).

Compounds of Formula I in which P are

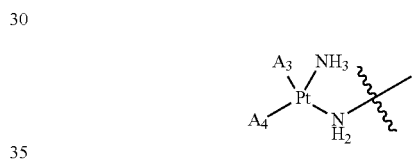

can be prepared according to general Scheme 3 below. $A_3$ and $A_4$, m, and Z in general Scheme 3 are the same as those described in the Summary section above.

Scheme 2

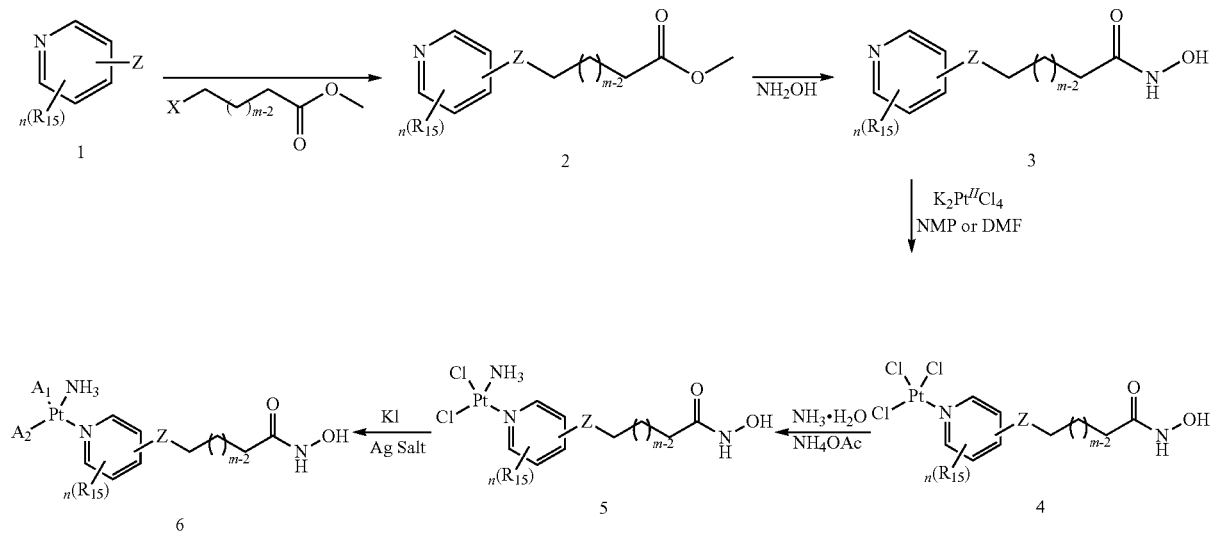

Scheme 3

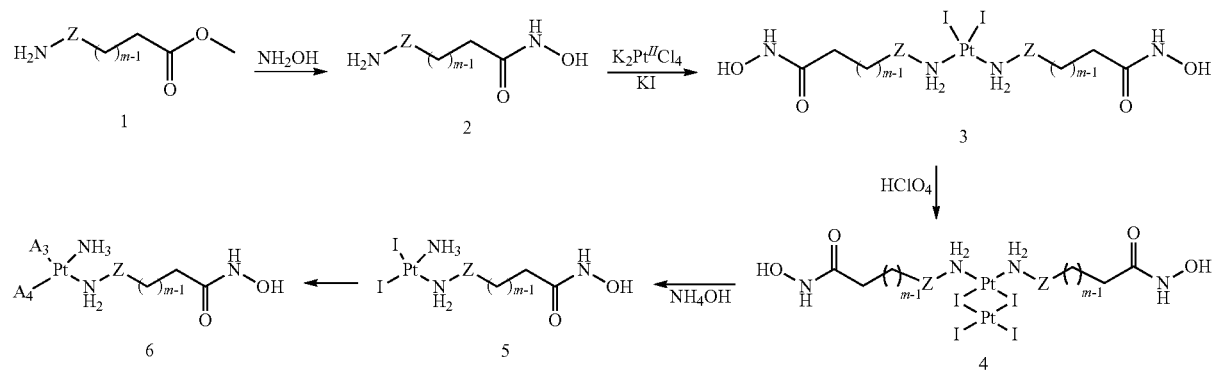

The starting material (1) undergoes a hydroxylamination reaction in NH$_2$OH to afford intermediate (2), which can react with K$_2$PtCl$_4$ and KI to give intermediate (3). The resulting intermediate (3) can react with HClO$_4$ to form oligomer (4) which subsequently reacts with NH$_4$OH to provide the intermediate (5). The intermediate (5) can react with an appropriate silver salt such as dicarboxylic acid salt to give final compound (6).

Compounds of Formula I in which P are

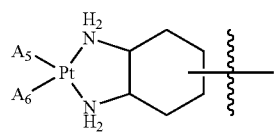

can be prepared according to general Scheme 4 below. A$_5$ and A$_6$, m, and Z in general Scheme 4 are the same as those described in the Summary section above.

The reagent (1) can be prepared by reacting K$_2$PtCl$_4$ and KI with trans-L-4-cyclohexene-1,2-diamine, which can be prepared according to the procedure similar to that described in *J. Mem. Chem.* 1987, vol. 30, 1327-1336. The starting material (1) can react with an appropriate silver salt such as dicarboxylic acid salt to give intermediate (2). Meanwhile, the reagent (4) can be prepared by a hydroxylamination reaction of an appropriate halo-substituted ester (3) in NH$_2$OH. The reaction of intermediate (2) and (4) will lead to final product (5).

Compounds of Formula I in which P are

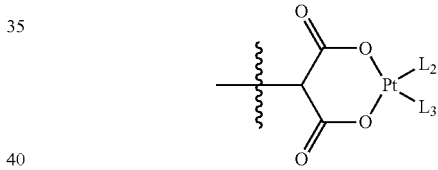

can be prepared according to general Scheme 5 below. L$_2$ and L$_3$, m, and Z in general Scheme 5 are the same as those described in the Summary section above.

Scheme 4

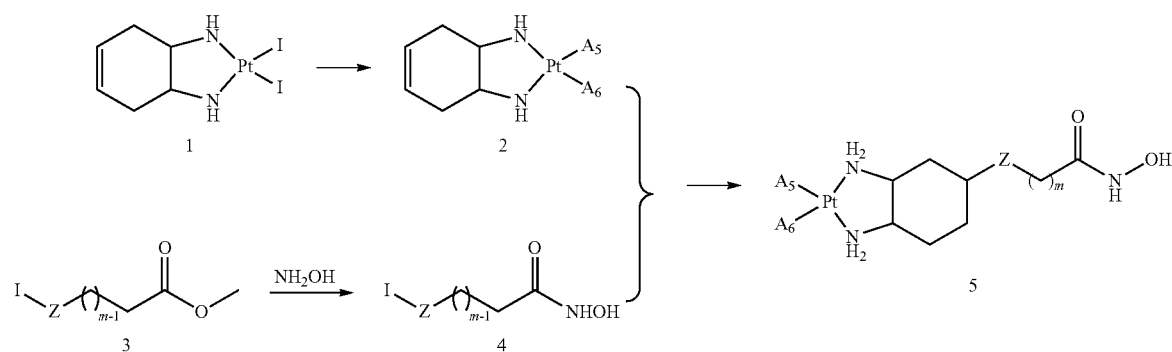

Scheme 5

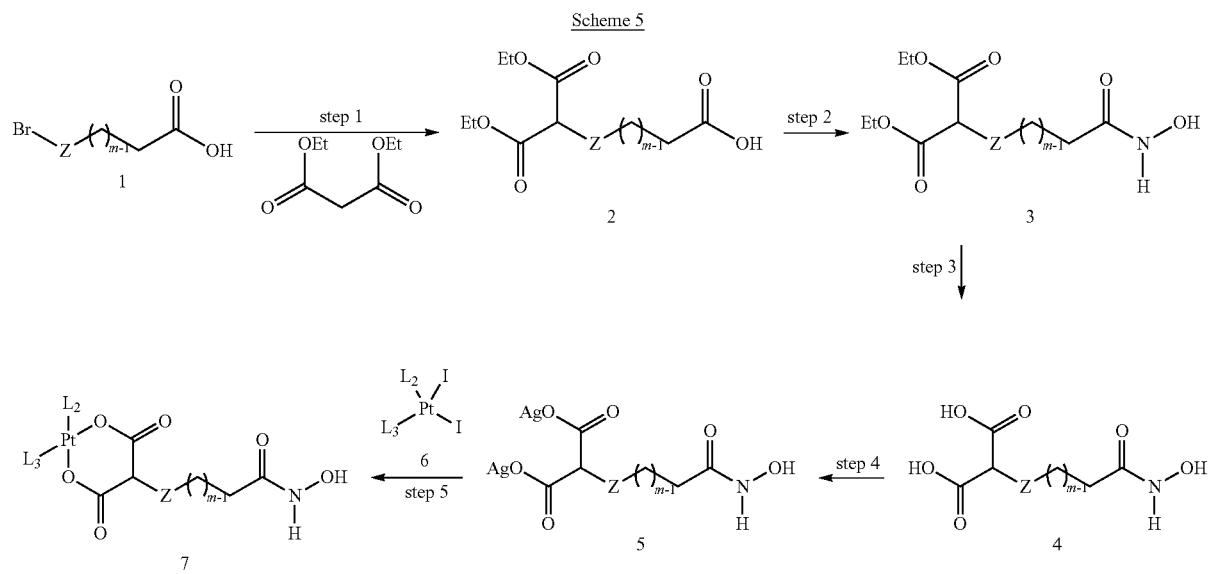

Specifically, the starting material (1), a halo-substituted carboxylic acid, can react with diethyl malonate to afford carboxylic acid intermediate (2), which can subsequently converted to a hydroxamic acid intermediate (3). Intermediate (3) can be hydrolyzed to intermediate (4) which can then be converted to a silver salt (5). The resulting silver salt (5) can react with an appropriate Pt(II) complex (6) to form the final compounds (7).

The Pt(II) complex (6) can be prepared by reacting the $K_2PtCl_4$ with KI and appropriate amine $L_2$ and $L_3$.

Compounds of Formula I in which P are

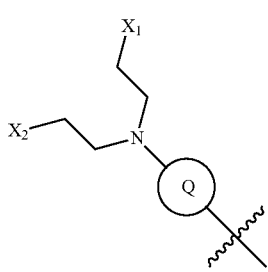

(wherein Q is an aryl or heteroaryl, e.g. 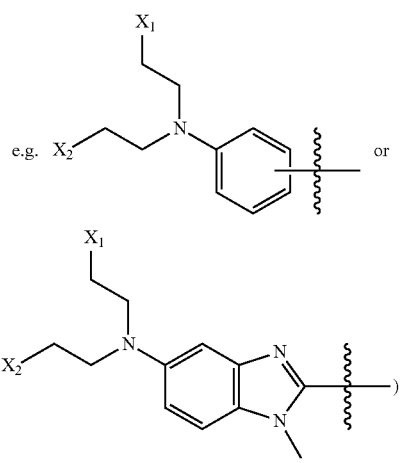 or can be prepared according to general Scheme 6 below. $X_1$, $X_2$, Z, and m in general Scheme 6 are the same as those described in the Summary section above.

Scheme 6

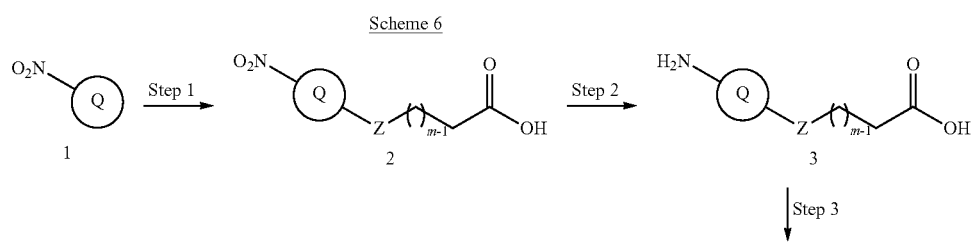

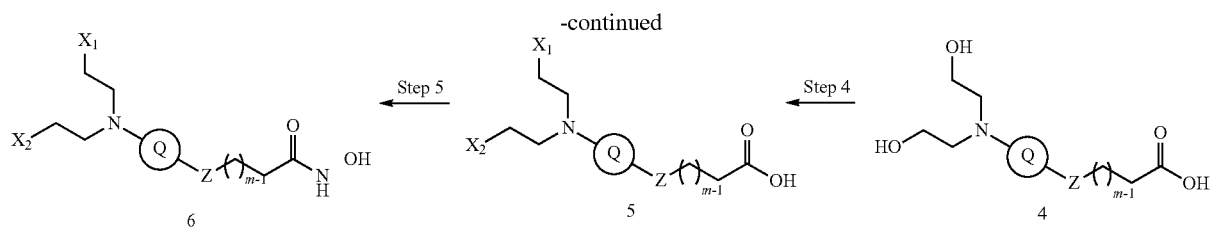

The starting material (1), a nitro-substituted 5-10 membered ring, can couple with an appropriate carboxylic acid to give intermediate (2), which can be subsequently reduced, for example with $H_2$, Pd/C, to an amino-substituted intermediate (3). The resulting intermediate (3) can be easily converted to intermediate (4) and then intermediate (5) by standard organic synthesis techniques with high yield. The hydroxylamination of intermediate (5) in $NH_2OH$ can afford the final compound (6).

Compounds of Formula I in which P are

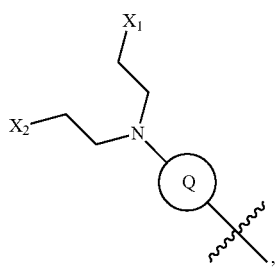

(wherein Q being a aryl or heteroaryl substituted with at least one nitro group,

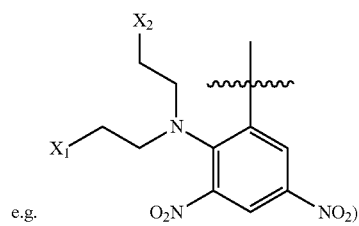

can be prepared according to general Scheme 7 below. $X_1$, $X_2$, Z, and m in general Scheme 8 are the same as those described in the Summary section above.

Scheme 7

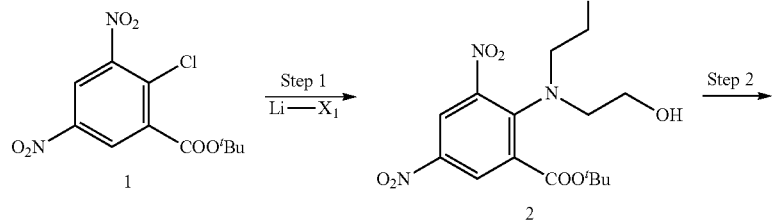

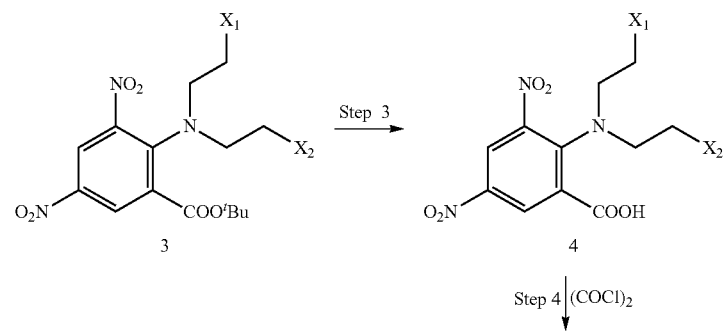

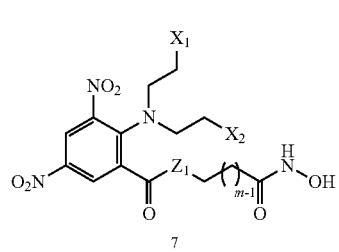 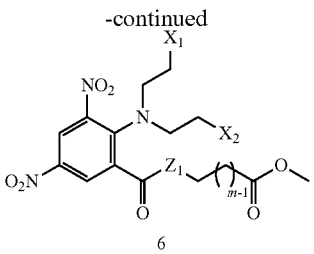 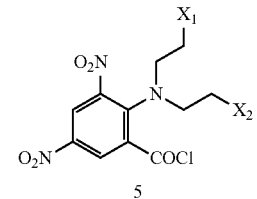

The starting material (1) can react with $L_1$-$X_1$ (e.g $X_1$ is Br) and 1-aziridineethanol leading to intermediate (2), which can be subsequently converted to intermediate (3) (for example, $X_2$ is —$OSO_2CH_3$). After that, the intermediate (3) can be hydrolysized to an appropriate carboxylic acid (4) which will react with $(COCl)_2$ to afford the carboxylic acid chloride intermediate (5). The intermediate (5) will couple with appropriate ester leading to intermediate (6), which will undergone hydroxylamination reaction to afford final product (7).

Compounds of Formula I in which P are

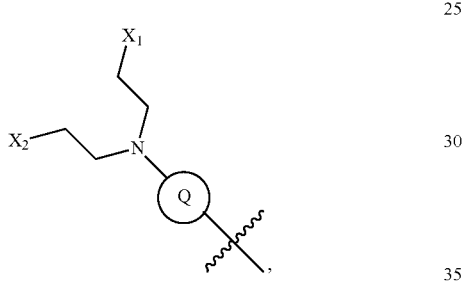

(wherein Q being a phosphorus-containing heterocycloalkyl,

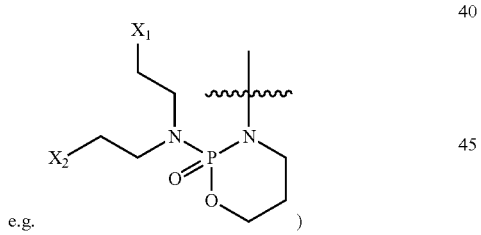

e.g. )

can be prepared according to general Scheme 8 below. $X_1$, $X_2$, Z, and m in general Scheme 7 are the same as those described in the Summary section above.

Scheme 8

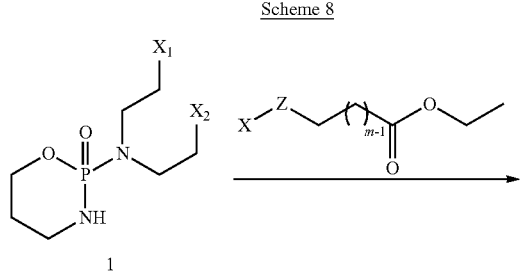

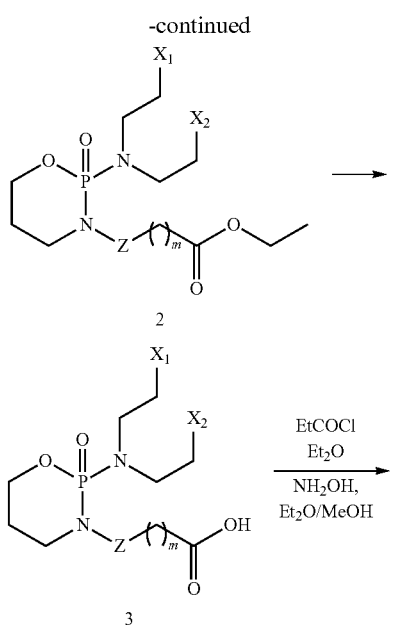

The starting material (1) can react with halide X—Z—$(CH_2)_m COOCH_3$ to give intermediate (2), in which Z could be $CH_2$, C(O), C(O)O, C(O)S, or $SO_2$. The intermediate (2) can be hydrolysized to carboxylic acid intermediate (3) which can be converted to the final product (4).

As another example, compounds of Formula I in which P are

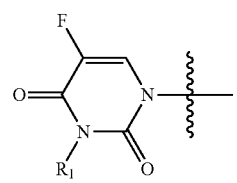

can be prepared according to general Scheme 9. m and Z in general Scheme 9 are the same as those described in the Summary section above.

Scheme 9

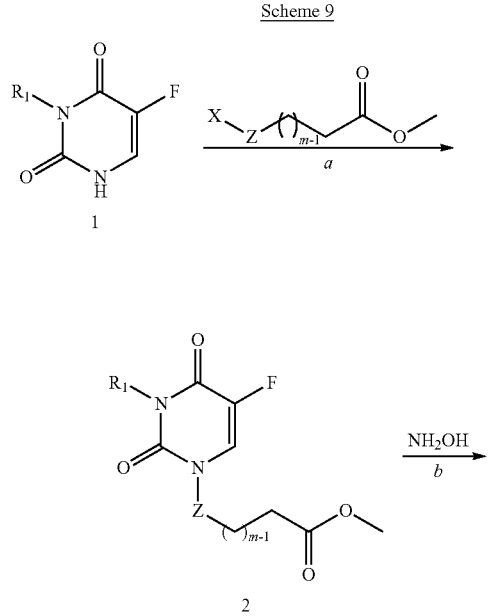

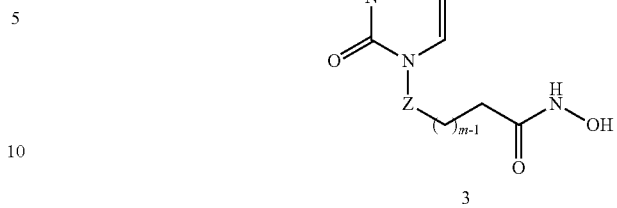

The starting material (1) can react with halide X—Z—$(CH_2)_m COOCH_3$ to give intermediate (2), in which Z could be $CH_2$, C(O), C(O)O, C(O)S, or $SO_2$, The hydroxylamination of intermediate (2) in $NH_2OH$ leads to the final compound (3).

Compounds of Formula I in which P are

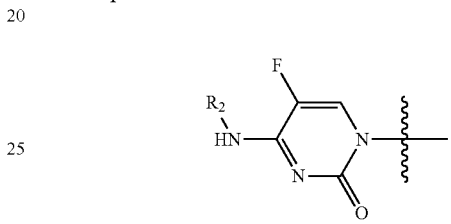

can be prepared according to general Scheme 10 below. Z and m in general Scheme 10 are the same as those described in the Summary section above.

Scheme 10

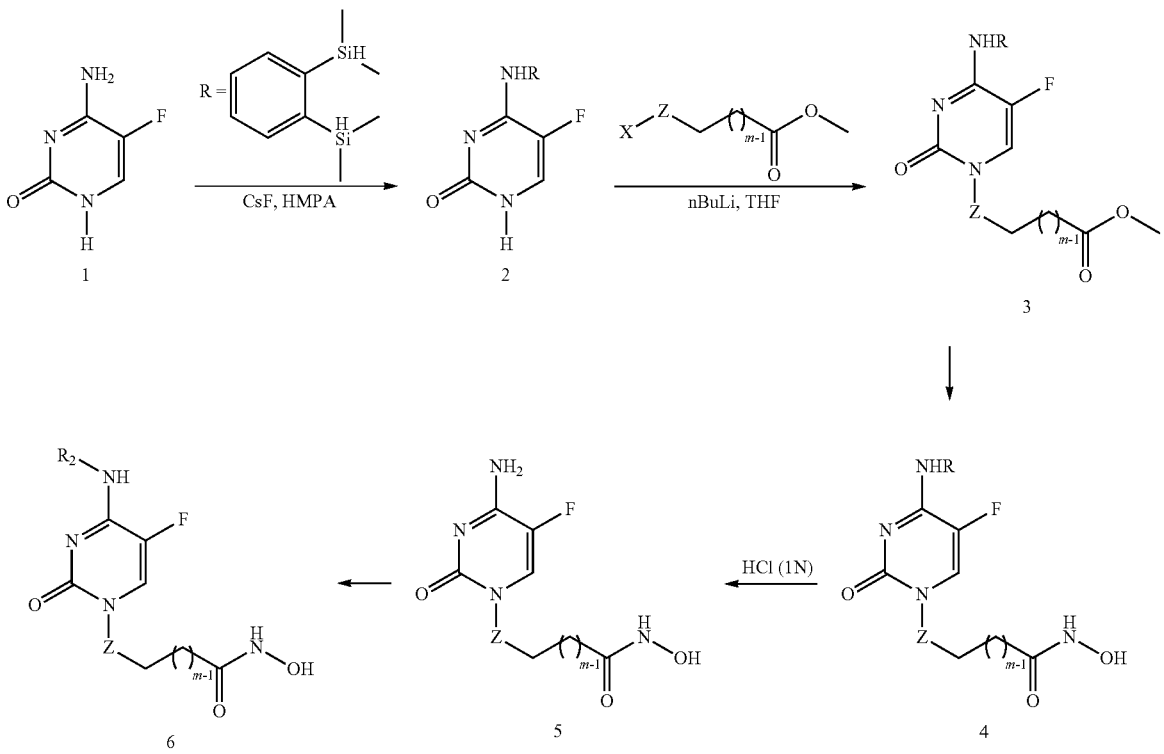

The NH$_2$ group of starting material (1) can be protected by reacting with silane, resulting the intermediate (2) which can couple with appropriate ester to produce the intermediate (3). The hydroxylamination of intermediate (3) in NH$_2$OH can afford the intermediate (4). The deprotection of NH$_2$ in HCl leads to intermediate (5), which will subsequently converted to final product (6).

Compounds of Formula I in which P are

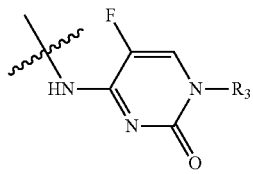

(for example R$_3$=H) can be prepared according to general Scheme 11 below. Z and m in general Scheme 11 are the same as those described in the Summary section above.

Scheme 11

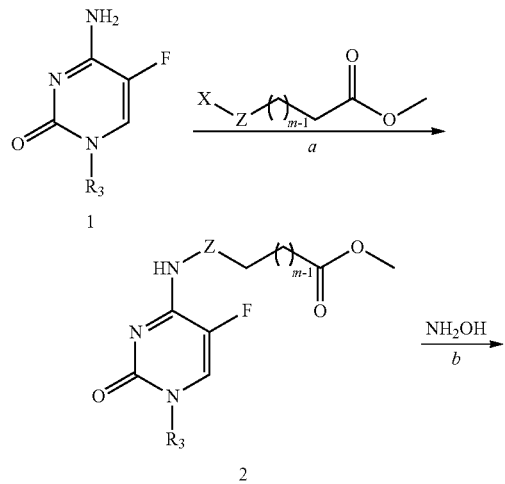

-continued

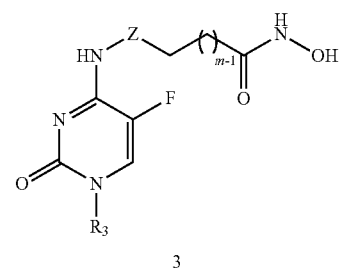

The starting material (1) can react an appropriate ester to form intermediate (2), which will undergo the hydroxylamination in NH$_2$OH can afford the final compound (3).

Compounds of Formula I in which P are

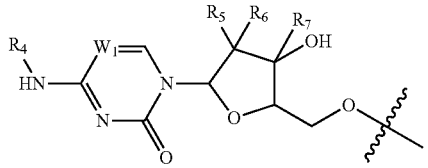

can be prepared according to general Scheme 12. W$_1$, R$_4$, R$_5$, R$_6$, R$_7$, Z and m in general Scheme 12 are the same as those described in the Summary section above.

Scheme 12

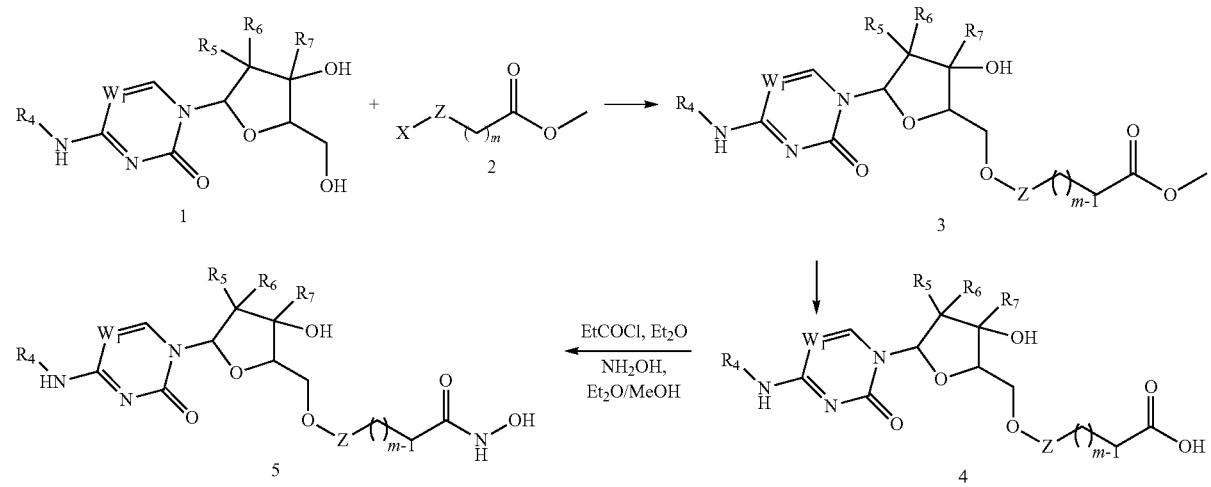

The starting material (1) within this invention is typically a commercially available drug, such as Gemcitabine, Decitabine, Azacitidine (aza-C), TAS-106, Cytarabine, Enocitabine, or Sapacitabine. The starting material (1) can couple with an appropriate halide X—Z—(CH$_2$)$_m$COOCH$_3$ (2) to afford intermediate (3), in which Z could be CO, C(O)NH, C(O)S, SO$_2$, or CH$_2$. Intermediate (3) can be then hydrolyzed to carboxylic acid intermediate (4), which can be subsequently one-step converted to hydroxamic acid under neutral pH condition.

Compounds of Formula I in which P are

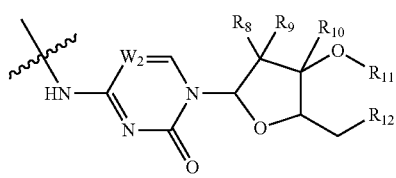

can be prepared according to general Scheme 13. W$_2$, R$_8$, R$_9$, R$_{10}$, R$_{11}$, R$_{12}$, Z and m in general Scheme 13 are the same as those described in the Summary section above.

The starting material (1) within this invention is typically a commercially available drug, such as Gemcitabine, Decitabine, Azacitidine (aza-C), TAS-106, Cytarabine, Enocitabine, or Sapacitabine. The starting material (1) can couple with an appropriate ester (2) to afford intermediate (3), in which Z can be C(O), C(O)O, or C(O)S. The resulting intermediate (3) can be then hydrolyzed to carboxylic acid intermediate (4), which can be subsequently one-step converted to hydroxamic acid under neutral pH condition.

More specifically, compounds of Formula I in which P are

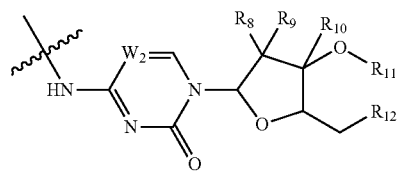

wherein W$_2$ is CF, R$_8$, R$_{10}$, and R$_{12}$ are H, can be prepared according to general Scheme 14 below. R$_9$, R$_{11}$, Z and m in general Scheme 14 are the same as those described in the Summary section above.

Scheme 13

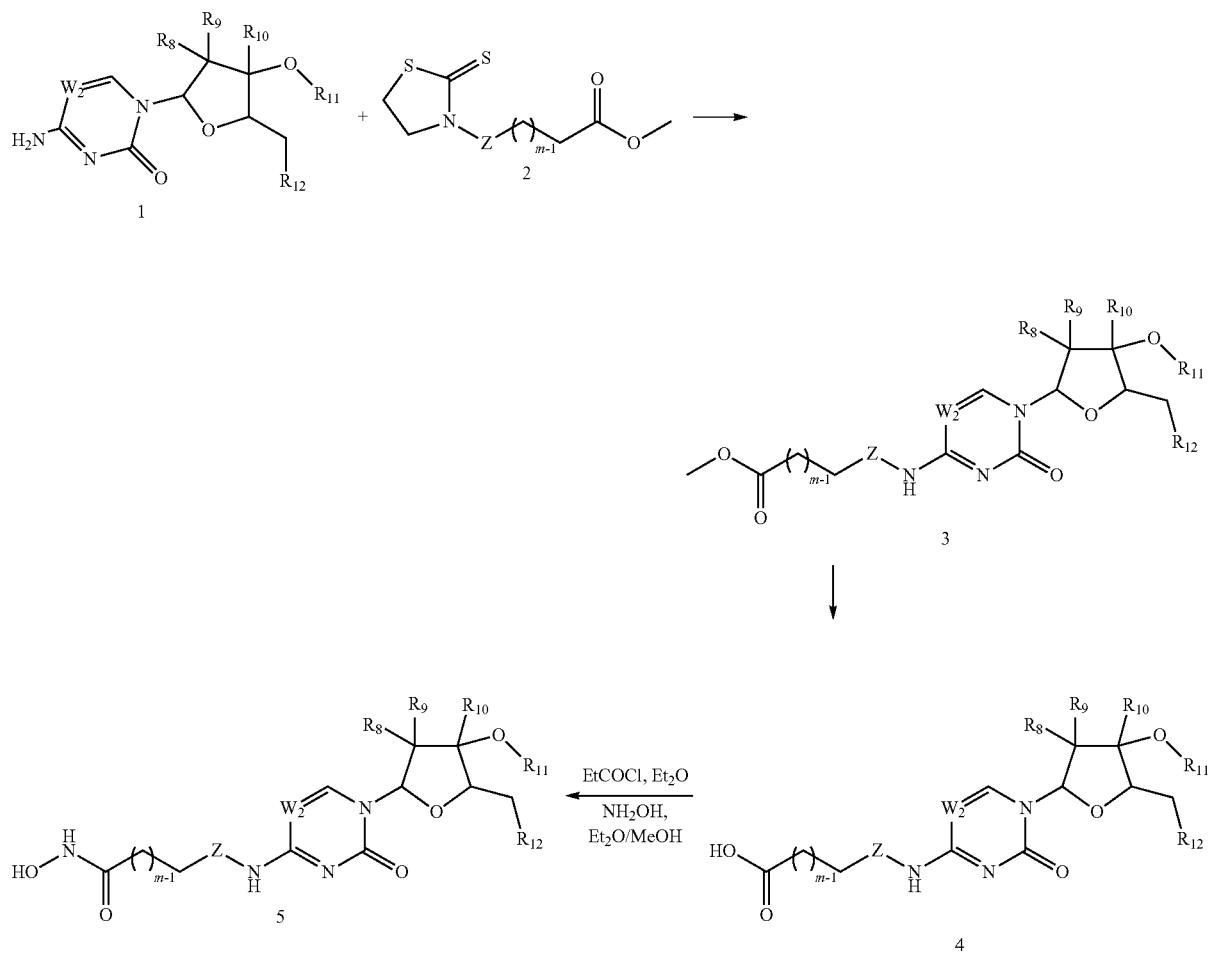

Scheme 14

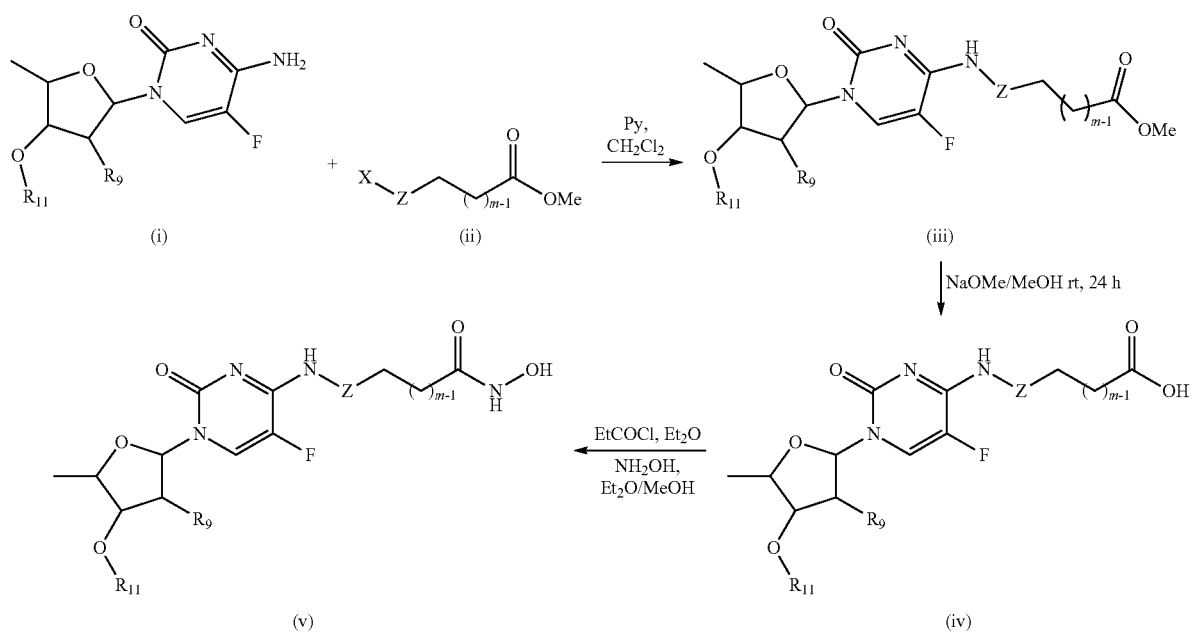

The starting material (i) can couple with an appropriate ester (ii) to afford intermediate (iii), in which Z could be CO, C(O)S, C(O)O, C(O)NH, or SO$_2$, or CH$_2$. Intermediate (iv) can be then hydrolyzed to carboxylic acid intermediate (v), which can be subsequently one-step converted to hydroxamic acid under neutral pH condition.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

The invention further relates to a pharmaceutical composition for the treatment of a neoplastic disorder in a mammal which comprises a therapeutically-effective amount of the compound represented by Formula I, or a pharmaceutically acceptable salt, a hydrate, a solvate, a prodrug, an antive metabolite, a corresponding enantiomer, a corresponding racemate, or a corresponding diastereomer thereof.

In a preferred embodiment, wherein said neoplastic disease is selected from the group consisting of lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome and myeloproliferative disease.

It is well known that immunosuppression is one of major side-effect of a chemotherapeutial agent. At low dose, chemotherapeutial agent can be used to treat immune diseases such as multiple sclerosis, rheumatoid arthritis and the suppression of transplant rejections. For example, Methotrexate, a well known chemotherapeutical agent recently has come into use as a treatment for some autoimmune diseases, including ankylosing spondylitis, Crohn's disease, psoriasis, psoriatic arthritis, rheumatoid arthritis, and scleroderma. Another well-known drug Mitoxantrone is used to treat multiple sclerosis, most notably the subset known as secondary progressive multiple sclerosis. For a third example, the DNA alkylating agent Cyclophosphamide has been used in various non-neoplastic autoimmune diseases such as systemic lupus erythematosus (SLE), minimal change disease, severe rheumatoid arthritis, Wegener's granulomatosis (with trade name Cytoxan), and multiple sclerosis (with trade name Revimmune). Therefore it is not difficult to imagine that a compound represented by Formula I could be used for treatment of an immune disease. The invention further relates to a pharmaceutical composition for the treatment of an immune disease in a mammal which comprises a therapeutically-effective amount of the compound of Formula I, or a pharmaceutically acceptable salt, a hydrate, a solvate, a prodrug, an antive metabolite, a corresponding enantiomer, a corresponding racemate, or a corresponding diastereomer thereof.

In a preferred embodiment, the immune disease is selected from the group consisting of the rejection of transplanted organs and tissues, a graft-versus-host disease, a non-autoimmune inflammatory disease, and an autoimmune disease, wherein said autoimmune disease is selected from the group consisting of acute disseminated encephalomyelitis, addison's disease, ankylosing spondylitis, antiphospholipid antibody syndrome, autoimmune hemolytic anemia, autoimmune hepatitis, autoimmune inner ear disease, bullous pemphigoid, coeliac disease, chagas disease, chronic obstructive pulmonary disease, churg-strauss syndrome, dermatomyositis, Crohn's disease, diabetes mellitus type 1, endometriosis, goodpasture's syndrome, graves' disease, guillain-barré syndrome, hashimoto's disease, hidradenitis suppurativa, idiopathic thrombocytopenic purpura, interstitial cystitis, lupus erythematosus, morphea, multiple sclerosis, myasthenia gravis, narcolepsy, neuromyotonia, pemphigus vulgaris, pernicious anaemia, polymyositis, primary biliary cirrhosis, psoriasis, psoriatic arthritis, rheumatoid arthritis, schizophrenia, scleroderma, temporal arteritis, vasculitis, vitiligo, and wegener's granulomatosis.

DEFINITIONS

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl. "Alkoxy" means an oxygen moiety having a further alkyl substituent. "Alkoxycarbonyl" means an alkoxy group attached to a carbonyl group. "Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a nonaromatic 5-8 membered monocyclic, 8-12 membered bicyclic, or 11-14 membered tricyclic ring system having one or more heteroatoms (such as O, N, S, P, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_1$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

The term "bidentate ligand" refers to a ligand having two coordination sites that can simultaneous binding to a metal atom such as Platinum. Some typical bidentate ligands are bidentate amine, bidentate carboxylate, bidentate thiocarboxylate, bidentate diphosphine, bidentate mercaptopyrimidine, and bidentate dithiocarboxylate.

The term "cyclic amine" refers to a hydrocarbon ring wherein one carbon atom of the ring has been replaced by a nitrogen atom. Cyclic amine may contain one or more heteroatoms (such as O, N, S, P, or Se). The cyclic amine can be unsaturated, partially saturated, or fully saturated. The cyclic amine can also be bicyclic, tricyclic, and polycyclic. The cylic amine can be substituted or unsubstituted. Examples of cyclic amines include pyridine, pyridazine, pyrimidine, pyrazine, imidazole, pyrazole, pyrrole, oxazole, isoxazole, thiazole, thiadiazole, thiatriazole, indole, 1H-pyrrolo[2,3-c]pyridine, isoquinoline, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)NRaRb where Ra and Rb are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH=O.

"Formimino" means the radical —HC=NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture".

"Nitro" means the radical —NO$_2$.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, Protecting Groups in Organic Synthesis, 3rd edition, John Wiley & Sons, 1999.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, for example phenylsulfide; aralkylsulfide, for example benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., dogs, cats, rabbits, cattle, horses, sheep, goats, swine, deer, and the like) and non-mammals (e.g., birds, and the like).

"Disease" specifically includes any unhealthy condition of an animal or part thereof and includes an unhealthy condition that may be caused by, or incident to, medical or veterinary therapy applied to that animal, i.e., the "side effects" of such therapy.

"DNA alkylating agents" are capable of forming DNA adducts or crosslinks between DNA strands conditions present in cells. Example of DNA alkylating agents include (1) Nitrogen mustards such as Cyclophosphamide, Mechlorethamine, Uramustine, Melphalan, Chlorambucil, and Ifosfamide; (2) Platinum-based chemotherapeutic drug such as Cisplatin, Carboplatin, Oxaliplatin, and Satraplatin. Platinum-based chemotherapeutic drug is frequently designated as an alkylating agent, but it has no alkyl group and cannot carry out alkylating reactions. It is correctly classified as alkylating-like.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases.

"Prodrug" means a compound that is convertible in vivo metabolically into an inhibitor according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

As used herein, the term "treating" refers to administering a hydroxamic compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents. A "subject" refers to a human and a non-human animal Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

Utility

It should be recognized that the compounds of the present invention may be present and optionally administered in the form of salts, solvates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compound according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

A wide variety of compositions may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, or one or more other pharmaceutically active agents.

Furthermore, the compositions of the present invention may be in the form of controlled release or immediate release formulations.

A wide variety of administration methods may be used in conjunction with the compounds of the present invention. Compositions comprising the compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms. Compositions may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

The hydroxamic acid derivative according to the present invention may be synthesized according to a variety of reaction schemes. Some illustrative schemes are provided herein in the example. Other reaction schemes could be readily devised by those skilled in the art.

It should be understood that the invention is not limited to the particular embodiments shown and described herein, but that various changes and modifications may be made without departing from the spirit and scope of the invention as defined by the claims.

EXAMPLES

Where NMR data are presented, $^1$H spectra were obtained on either a Varian VXR-200 (200 MHz, $^1$H), Varian Gemini-300 (300 MHz) or XL400 (400 MHz) and are reported as ppm down field from Me$_4$Si with number of protons, multiplicities, and coupling constants in Hertz indicated parenthetically. Where HPLC data are presented, analyses were performed using an Agilent 1100 system. Where LC/MS data are presented, analyses were performed using an Agilent 6210 TOF LC/MS or an Applied Biosystems API-100 mass spectrometer and Shimadzu SCL-10A LC column. Altech platinum C18, 3 micron, 33 mm×7 mm ID; Samples were eluted using a linear gradient of 0-100% acetonitrile/pH4.50, 200 mM NH$_4$ acetate over 10 minutes with a flow rate of 3.0 mL/min. Chromatograms were generated over the range 240-400 nm using a diode array detector.

Example 1

The hydroxamic acid derivatives with P represented by

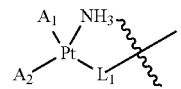

were synthesized according to the synthetic scheme below.

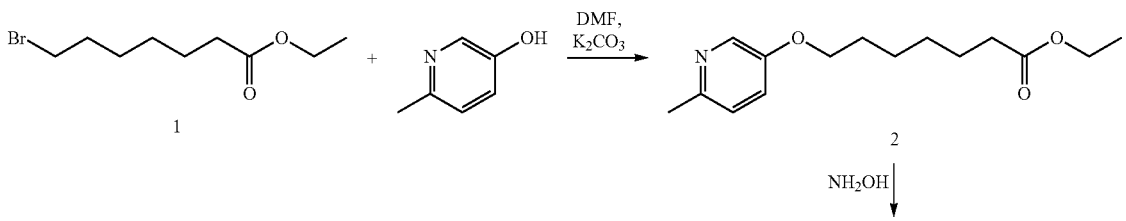

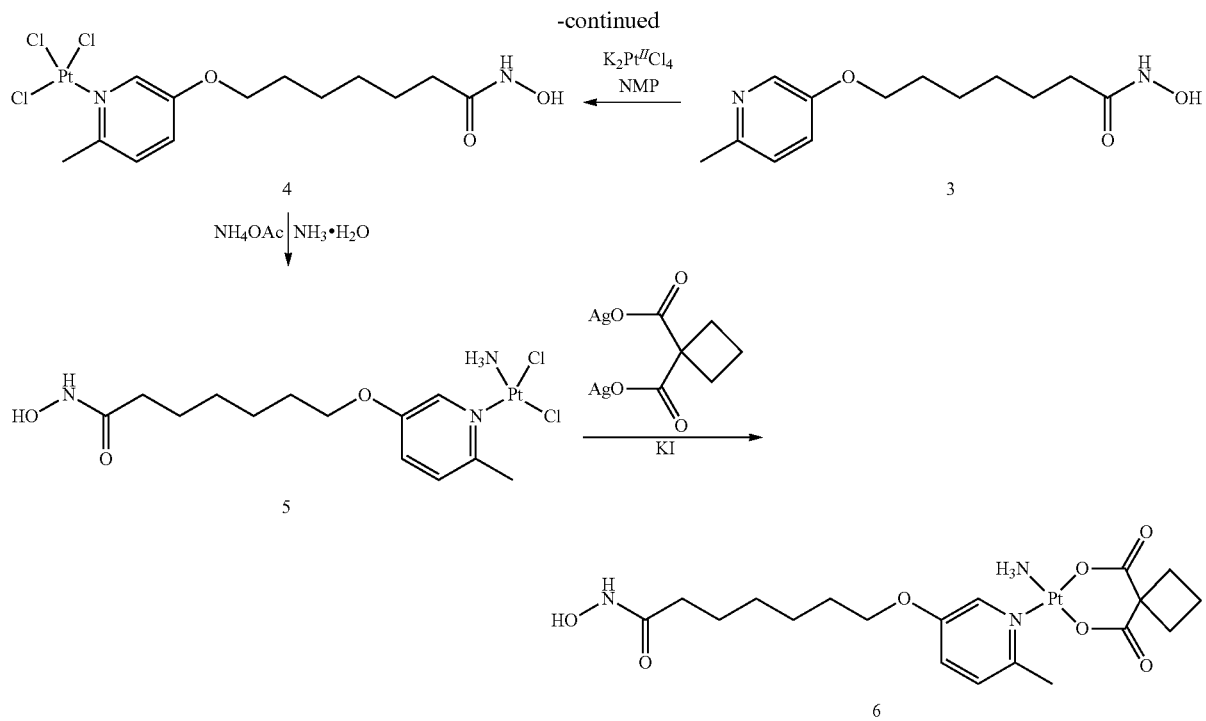

Step 1: A mixture of starting material 6-methylpyridin-3-ol (30 mmol), ethyl 7-bromoheptanoate (30 mmol) and potassium carbonate (100 mmol) in DMF (80 mL) was stirred at 60° C. for 3 hours. After reaction the mixture was filtrated. The filtrate was concentrated in vacuo and the residue was dissolved in dichloromethane and washed with brine twice. The organic phase was dried over sodium sulfate, filtered and concentrated to give (2).

Step 2: The freshly prepared hydroxylamine solution (60 mL, 220 mmol) was placed in 100 mL flask. Compound (2) (20 mmol) was added to this solution and stirred at 25° C. for 24 hours. After reaction the mixture was neutralized with acetic acid, and the resulting precipitate was isolated, washed with water, and dried to give the title intermediate (3).

Step 3: $K_2PtCl_4$ was ground into a very fine powder with a mortar and pestle 8.4 mmole of $K_2PtCl_4$ was placed in a 25 mL round bottom flask and 6-7 mL of dry NMP was added. 10 mmoles of intermediate (3) was placed in 3-4 mL of NMP and divided in 5 equal portions. The first portion of intermediate (3) was added to the Pt mixture. The mixture was completely immersed in a 60 degree C. oil bath and stirred at 1200 rpm. Subsequent portions of intermediate (3) were added at 30-35 minutes intervals. The rate of intermediate (3) addition was 20% every 30-35 minutes. After the addition of the last portion, the reaction was allowed to proceed for another 50 to 60 minutes. The reaction solution was orange in color at the end of the reaction. The reaction solution was allowed to cool to ambient temperature. 100 mL of methylene chloride was added to the reaction at ambient temperature. The addition of methylene chloride caused the precipitation of compound 4 and KCl. The precipitate was collected by vacum filtration using a glass frit and washed with methylene chloride (3×5 mL), followed diethyl ether (3×5 mL). The precipitate was dried under vacuum at ambient temperature for 16-24 hours to afford intermediate (4).

Step 4: 6 g (10 mmoles) of intermediate (4) was placed in a 25 mL round bottom flask and 10 mL of 2.5 N KCl solution added. 60 mmoles of ammonium acetate trihydrate was dissolved in 25 mL of 2.5 N ammonium hydroxide solution and added to the stirring Pt mixture. The total volume of the reaction was about 35 mL. The mixture was immersed in a 45 degree C. oil bath and was stirred for 1 hour in the dark at >1000 rpm. The yellow precipitate was collected by vacuum filtration using a glass frit and washed with water (2×5 mL) and acetone (3×5 mL). The precipitate was dried under vacuum at ambient temperature for 16-24 hours to afford intermediate 5.

Step 5: Intermediate 5 (4 mmol) was mixed with $Ag_2CBDCA$ (5 mmol) in 200 ml of $H_2O$ for overnight in the dark. After removal of AgI by filtration through celite, the solution was evaporated to about 2 ml under reduced pressure. The precipitate was filtered, washed with water and acetone, and dried in vacuum to afford the final product (6).

The following compounds were prepared by a slightly modified scheme of Example 1:

| Structure |
| --- |
| 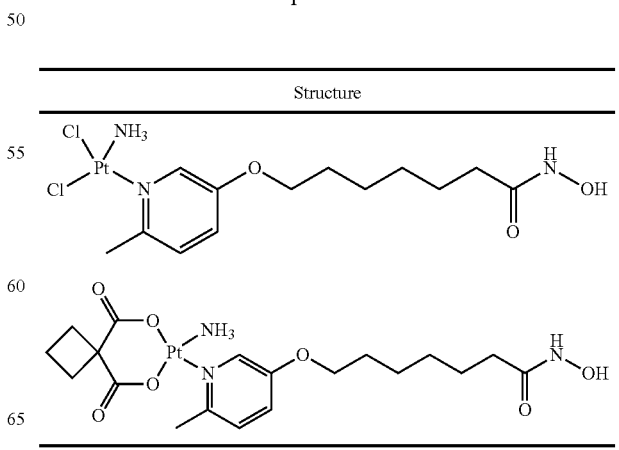 |

Example 2

The hydroxamic acid derivatives with P represented by

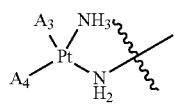

were synthesized according to the synthetic scheme below.

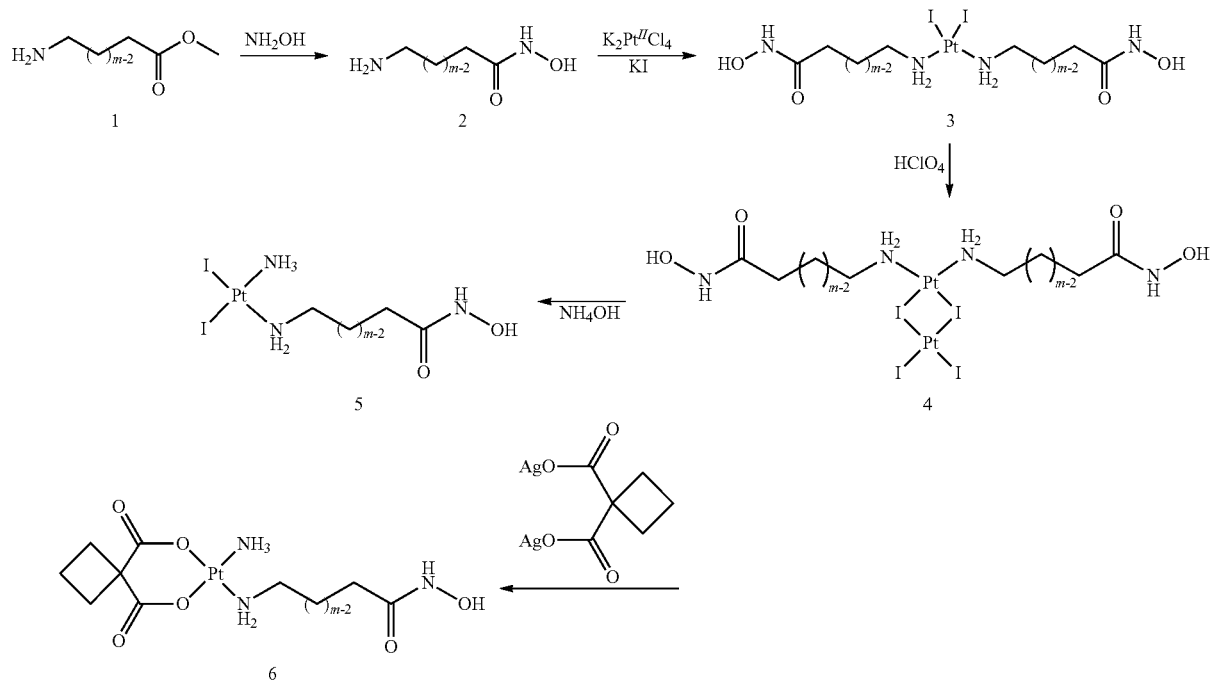

Step 1: To a solution of the starting material (1) (20 mmol) in diethylether (60 mL) at 0° C. ethylchloroformate (24 mmol) and N-methylmorpholine (26 mmol) were added and the mixture was stirred for 10 min. The solid was filtered off and the filtrate was added to freshly prepared hydroxylamine (30 mmol) in methanol. The reaction mixture was stirred at room temperature for 15 min. The solvent was evaporated to obtain the final product with a purity of at least 99% area by HPLC.

Step 2: An aqueous solution of $K_2PtCl_4$, (20 mmol) was treated with KI (200 mmol) and stirred for 10 min at room temperature. Two equivalents of intermediate (2) was added dropwise to the resulting $K_2PtI_4$, solution. Upon stirring for 30 min, the yellow precipitate was filtered and washed extensively with water. The precipitate was recrystallized from the DMF/$H_2O$ mixture. After washing with water, methanol, and diethyl ether, the intermediate (3) was dried in vacuum.

Step 3: To a suspension of intermediate (3), (10 mmol) in 50 ml of $H_2O$ containing 10 ml of 68-70% $HClO_4$ was added 150 ml of ethanol. In the course of the reaction samples were taken for Pt NMR spectroscopic analysis. At the end of four days of stirring at room temperature the brown precipitate was filtered, washed with water, and dried in vacuum to afford intermediate (4).

Step 4: The intermediate (4) (5 mmol) was mixed with 5 ml of 1.5 M $NH_4OH$ in 25 ml of $H_2O$. The mixture was stirred at room temperature overnight. Again the completeness of the reaction was monitored by Pt NMR spectroscopy. The yellow precipitate was filtered, washed with water, and dried in vacuo to afford intermediate (5).

Step 5: The intermediate (5) (4 mmol) was mixed with $Ag_2CBDCA$ (5 mmol) in 200 ml of $H_2O$ for overnight in the dark. After removal of AgI by filtration through celite, the solution was evaporated to about 2 ml under reduced pressure. The precipitate was filtered, washed with water and acetone, and dried in vacuum to afford the final intermediate.

The following compounds were prepared by a slightly modified scheme of Example 2:

| Structure |
|---|
| 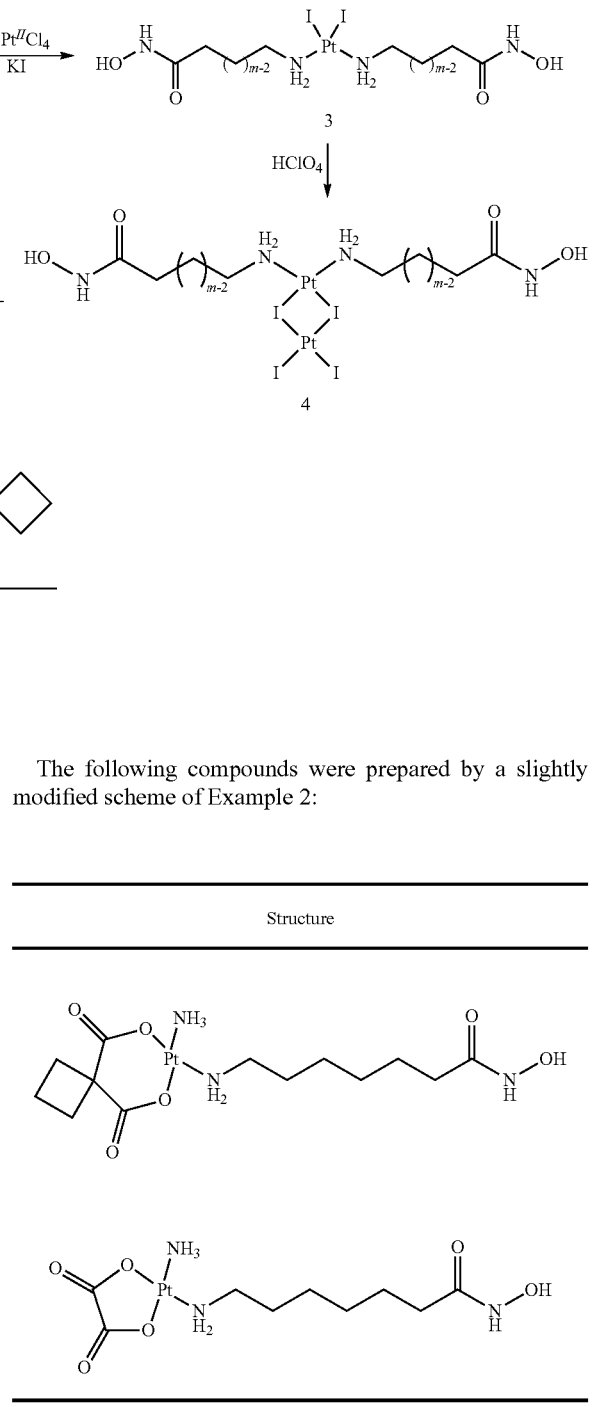 |

Example 3

The hydroxamic acid derivatives with P represented by

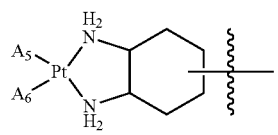

were synthesized according to the synthetic scheme below.

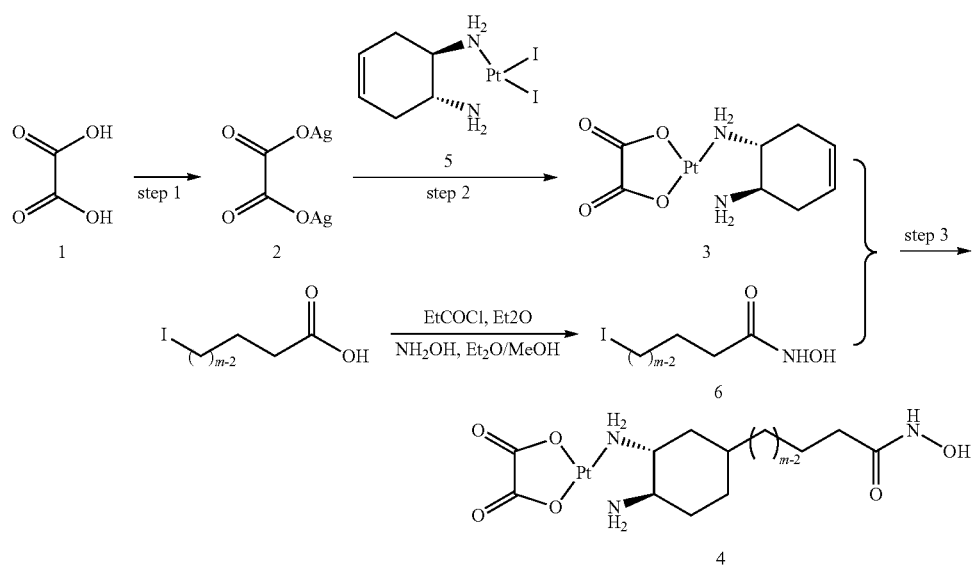

Step 1. (Synthesis of 2) Aqueous NaOH (20 mmol) was added to 10 mmol of the 1 dissolved in a small quantity of water. 20 mmol of AgNO$_3$ was then added to the sodium dicarboxylate solution in the dark. A white precipitate formed immediately. The mixture was stirred for 15-30 min and the silver compound 2 was filtered, washed with water, dried in air and finally in a dessicator.

Step 2. (Synthesis of 3) Compound 2 and 5 were mixed together in water in a 1:1 proportion. The mixture was stirred in the dark during 2~3 days until the formation of AgI was complete. The yellow precipitate was filtered out and the filtrate was evaporated to dryness.

Step 3. (Synthesis of 4) To a sonicated solution of 3 (1 equiv.) and iodide 6 (2 equiv.) in aqueous EtOH (70% v/v) was added CuI (2 equiv.) and Zn (6 equiv.). After a few minutes, more aqueous EtOH (70% v/v) was added and sonication was continued for 45-90 min. The mixture was diluted with Et$_2$O, sonicated for 10 min, and filtered through a short pad of Celite, washing the solids with EtOAc 3 times. The combined organic phases were washed with brine, dried (MgSO$_4$), filtered, and concentrated under reduced pressure.

Step 4. (Synthesis of 5) 34.4 g of potassium tetrachloroplatinate were dissolved in 275 ml of water. A solution of 80.1 g of KI in 140 ml of water was prepared. Both solutions were mixed for 15 min to obtain a mixed solution, which was then added to an aqueous solution previously prepared with 10 g of trans-L-4-cyclohexene-1,2-diamine having an optical purity of at least 99.9% area by HPLC in 30 ml of water. The reaction solution was stirred at rt for 10 h to form crude cis-diiodo-(trans-L-4-cyclohexene-1,2-diamine) Pt (II) complex, which was filtered off from the reaction solution as a precipitate and washed 3 times with 55 ml of water. The precipitate was then re-suspended in 220 ml of water for 15 min and filtered off from the suspension, and washed with water until halogen ions were not detected. The washed precipitate was suspended in 45 ml of a solution previously prepared with 50% of dimethylformamide and 50% of water for 15 min. The suspended precipitate was filtered off from the suspension, washed 3 times with 10 ml of the solution 50% from the dimethylformamide/water, then washed 3 times with 30 ml of water and finally washed 3 times with 20 ml of acetone to obtain 5, which was dried under vacuum at 25~30° C. for 12 h to obtain pure 5.

The following compounds were prepared by a slightly modified scheme of Example 3.

| Structure |
|---|
| 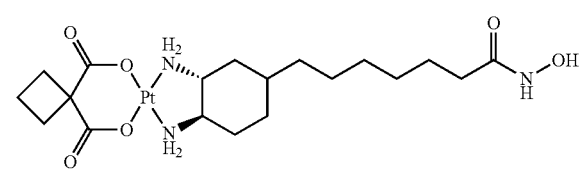 |
| 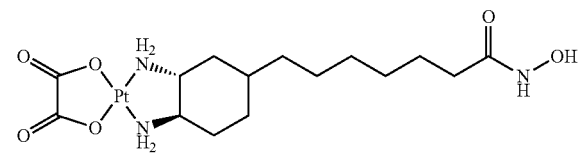 |

Example 4

The hydroxamic acid derivatives with P represented by

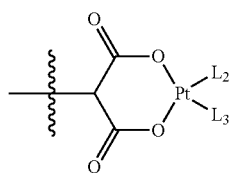

were synthesized according to the synthetic scheme below.

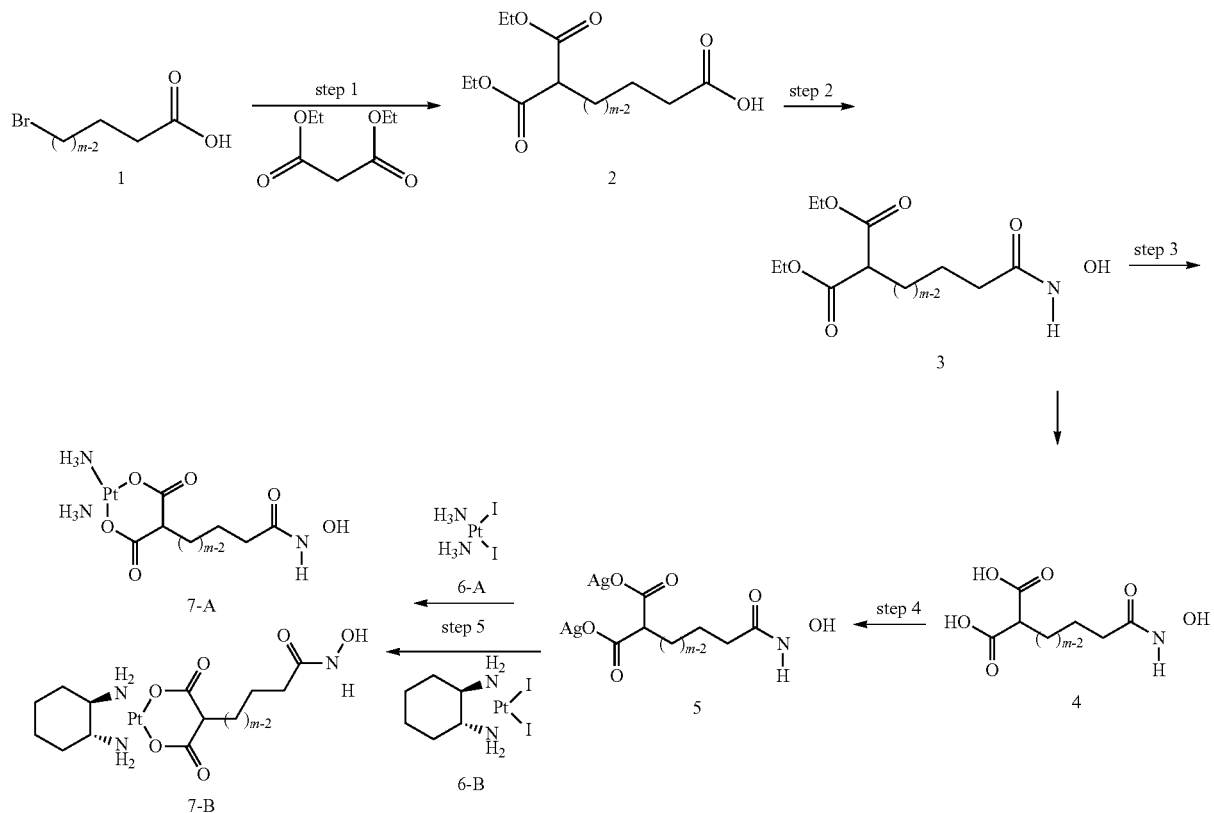

Step 1. (Synthesis of 2) Sodium ethoxide (solution in ethanol) (200 mmol) was cooled to 0° C. Diethyl malonate (11.5 ml, 100 mmol) was slowly added and stirring was continued for 30 min at 0° C. 1 (100 mmol) was then added slowly. The mixture was allowed to warm to rt and then heated to reflux for another 3 h. After the solvent was evaporated under reduced pressure, the residue was treated with 200 ml of 1N HCl. The white precipitate was filtered, washed with water and dried.

Step 2. (Synthesis of 3) To a solution of the acid 2 (80 mmol) in ether (200 ml) at 0° C., ethylchloroformate (10.4 g, 96 mmol) and N-methylmorpholine (10.4 g, 10.4 mmol) were added and the mixture was stirred for 10 min. The solid was filtered off and the filtrate was added to freshly prepared hydroxylamine (4.0 g, 120 mmol) in methanol. The reaction mixture was stirred at rt for 15 min. The solvent was evaporated and the residue was purified by silica gel column chromatography to obtain 3.

Step 3. (Synthesis of 4) A solution of 3 (15 mmol) in MeOH (200 ml) was added NaOMe (2.5 g, 45 mmol). The reaction solution was stirred at rt for 24 h. Then the mixture was added with HCl solution (1.4 mol/L) to pH 6.5 and evaporated. The residue was recrysallized from ethyl acetate to provide 4.

Step 4. (Synthesis of 5) Aqueous NaOH (20 mmol) was added to 10 mmol of the 4 dissolved in a small quantity of water. 20 mmol of $AgNO_3$ was then added to the sodium dicarboxylate solution in the dark. A white precipitate formed immediately. The mixture was stirred for 15-30 min and the silver compound 5 was filtered, washed with water, dried in air and finally in a dessicator.

Step 5. (Synthesis of 7-A and 7-B): Compound 5 and 6-A (or 6-B) were mixed together in water in a 1:1 proportion. The mixture was stirred in the dark during 2~3 days until the formation of AgI was complete. The yellow precipitate was filtered out and the filtrate was evaporated to dry.

Step 6. (Synthesis of 6-B) 34.4 g of potassium tetrachloroplatinate were dissolved in 275 ml of water. A solution of 80.1 g of KI in 140 ml of water was prepared. Both solutions were mixed for 15 min to obtain a mixed solution, which was then added to an aqueous solution previously prepared with 10 g of trans-L-1,2-cyclohexanediamine having an optical purity of at least 99.9% area by HPLC in 30 ml of water. The reaction solution was stirred at rt for 10 h to form crude cis-diiodo-(trans-L-1,2 cyclohexanediamine) Pt (II) complex, which was filtered off from the reaction solution as a precipitate and washed 3 times with 55 ml of water. The precipitate was then re-suspended in 220 ml of water for 15 min and filtered off from the suspension, and washed with water until halogen ions were not detected. The washed precipitate was suspended in 45 ml of a solution previously prepared with 50% of dimethylformamide and 50% of water for 15 min. The suspended precipitate was filtered off from the suspension, washed 3 times with 10 ml of the solution 50% from the simethylformamide/water, then washed 3 times with 30 ml of water and finally washed 3 times with 20 ml of acetone to obtain 6-B, which was dried under vacuum at 25~30° C. for 12 h to obtain pure 6-B. The pure 6-B complex obtained had a m.p. between 275~300° C., an optical purity of at least 99.5% area by HPLC, and a weight of 37.0 g.

The following compounds were prepared by a slightly modified scheme of Example 4.

| Structure |
|---|
| 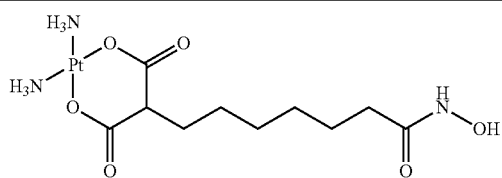 |
| 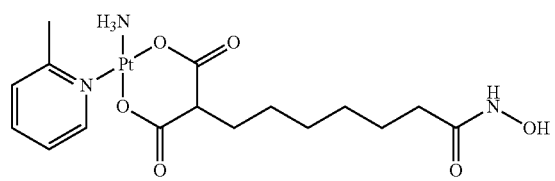 |
| 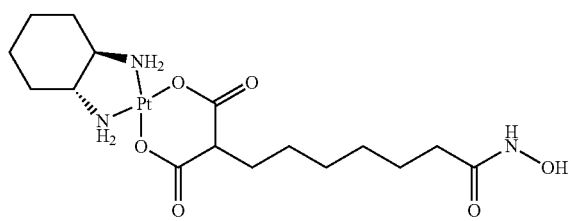 |

| -continued |
|---|
| Structure |
| 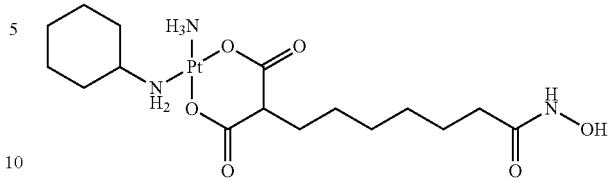 |

Example 5

The hydroxamic acid derivatives with P represented by

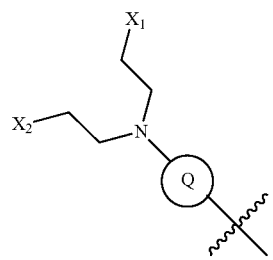

were synthesized according to the synthetic scheme below. In this example, Q is an aryl or heteroaryl (e.g. 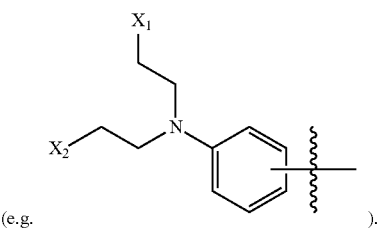).

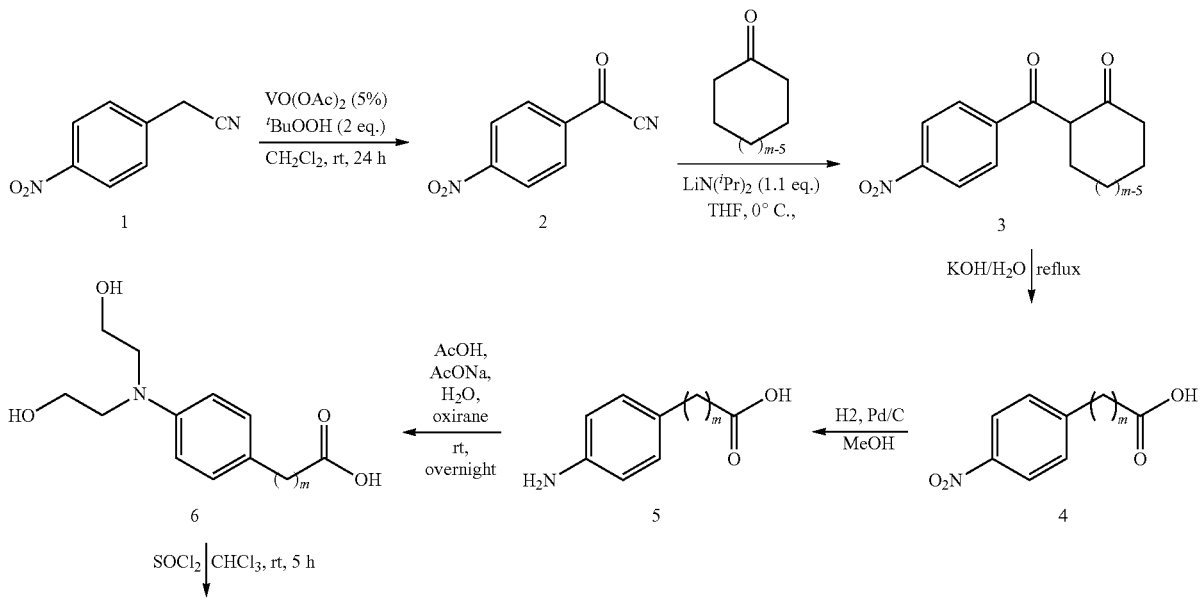

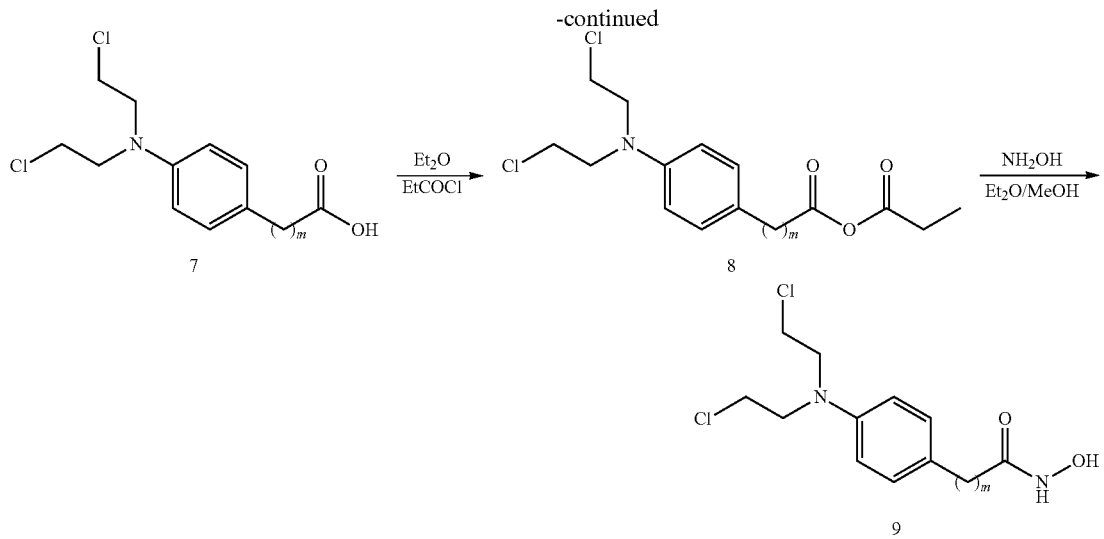

1 to 2: A two neck round bottomed flask was charged with vanadyl acetate (5%) and compound 1 in dry dichloromethane under $N_2$ atmosphere and two equivalents of t-BuOOH were then added to the reaction mixture and allowed to stir further at room temperature for 24 h. After the completion of reaction, the reaction mixture was then washed with distilled water and extracted with dichloromethane. The combined extracts were then concentrated and subjected to column chromatography to get pure aroyl cyanides.

2 to 3: The Ketone enolates (10 mmol) were formed using lithium diisopropylamide (1.1 equivalents) as base to react with Ketone. Under the conditions used (0° C., THF solution) 1.1 equivalents of acyl cyanide 2 in THF added in one portion to the enolate solution, acylation of the enolate was rapid, and no complications arose from competing acylation of diisopropylamine.

3 to 4: Compound 3 was suspended in water (50 mL) containing KOH (1.56 g) and heated under reflux until homogeneous (ca. 15 min) and for a further 1 h. The cooled mixture was acidified with dilute HCl and extracted with EtOAc (3×50 mL). The combined organic layers were worked up, and the residue was chromatographed on silica gel to afford the desired acid 4.

4 to 5: A solution of 4 (5.0 mmol) in MeOH (50 mL) and Pd/C (0.5 mmol) were stirred under $H_2$ for 4 h at room temperature. MeOH was removed under reduced pressure and the residue extracted with $CH_2Cl_2$. The organic layer was washed with NaCl solution, distilled $H_2O$ and dried with $Na_2SO_4$. The solvent was evaporated and the residue was purified by flash chromatography.

5 to 6: 5 (4.2 mmol) and AcOH (25 mL) was added in $H_2O$ (25 mL). The mixture was added dropwise oxirane slowly and stirred for 3 h at 10° C. Then the solution was stirred for overnight at room temperature. The mixture was poured into ice-cold $H_2O$ and distilled $H_2O$ and dried with $Na_2SO_4$. The solvent was evaporated and the residue was purified by flash chromatography.

6 to 7: A solution of 6 (3.5 mmol) in $CHCl_3$ (30 mL) was added dropwise $SOCl_2$ (4.5 mmol) for 1 h while ice-cooling. This reaction solution was stirred at room temperature for 4 h. The reaction mixture was washed with $H_2O$. The organic phase was dried over $MgSO_4$. The solvent was evaporated and the residue was purified by flash chromatography.

7 to 8: To a solution of the acid 6 (10 mmol) in diethylether (30 mL) at 0 degree C. ethylchloroformate (1.3 g, 12 mmol) and N-methylmorpholine (1.3 g, 13 mmol) were added and the mixture was stirred for 10 min. The solid was filtered off and the filtrate was used in the next step.

8 to 9: the filtrate was added to freshly prepared hydroxylamine (0.5 g, 15 mmol) in methanol. The reaction mixture was stirred at room temperature for 15 min. The solvent was evaporated and the residue was purified by silica gel column chromatography to obtain the final product 9.

The following compounds were prepared by a slightly modified scheme of Example 5.

| Structure | m/z [M + 1]+ |
|---|---|
| 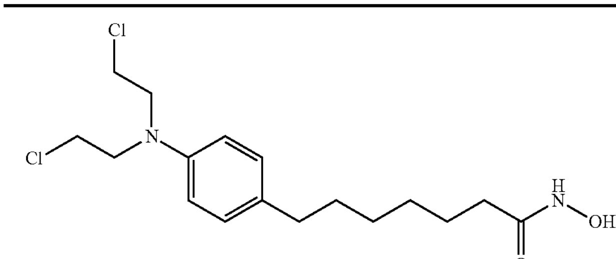 | 361 |

-continued
| Structure | m/z [M + 1]+ |
|---|---|
| 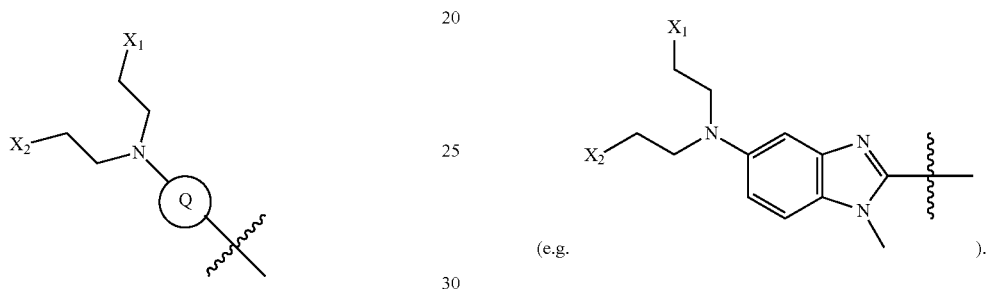 | 375 |
Example 6
The hydroxamic acid derivatives with P represented by
were synthesized according to the synthetic scheme below. In this example, Q is an aryl or heteroaryl
(e.g.          ).
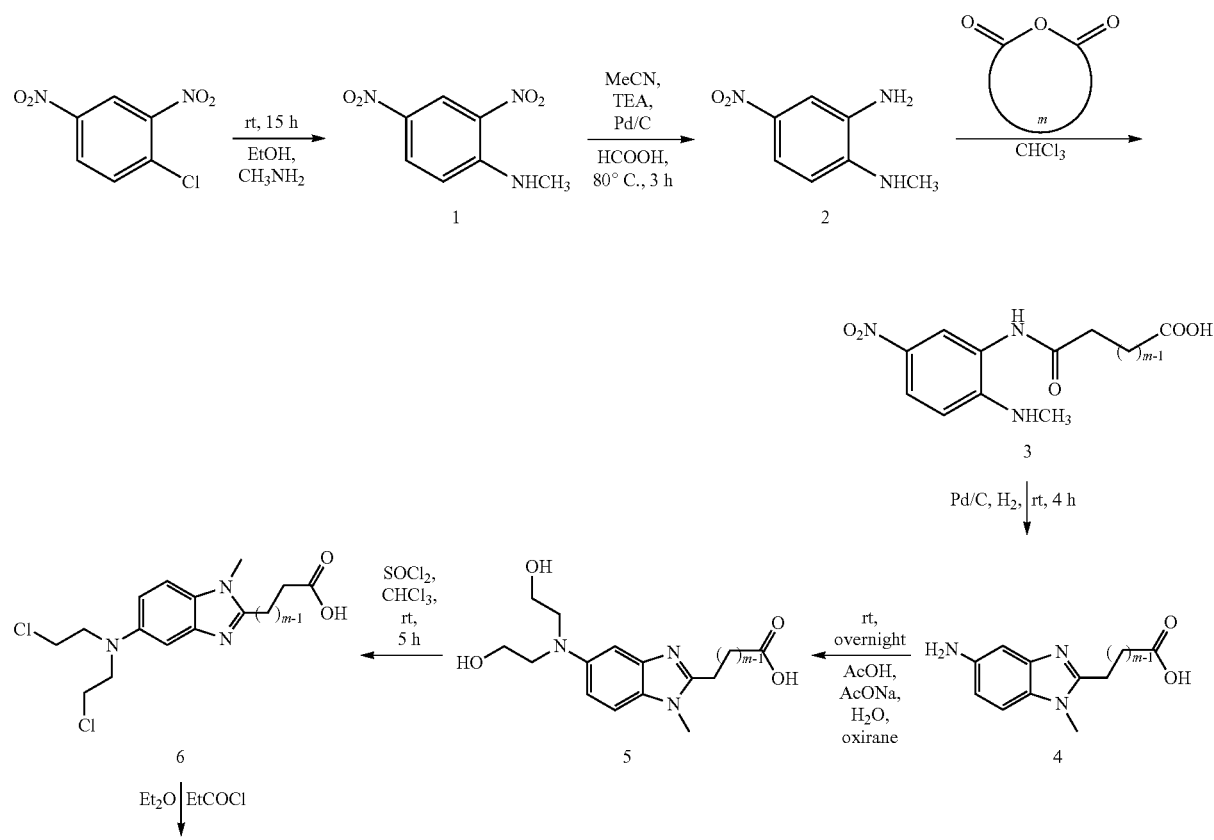

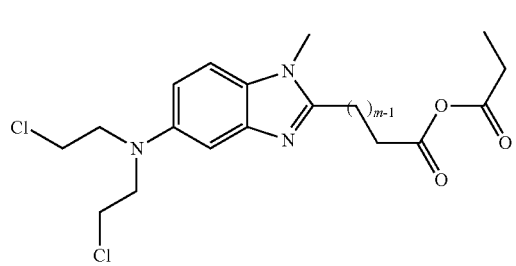
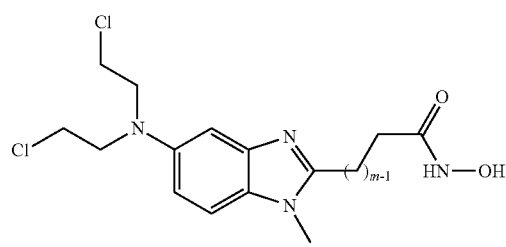

Step 1: Methylamine (40% w/w solution; 34 mL) was added to a solution of 1-chloro-2,4-dinitrobenzene (12.3 g, 61 mmol) in ethanol (120 mL), at 0° C. The mixture was stirred at room temperature for 15 h. The solvent was evaporated under reduced pressure and the brown oil residue was treated with hot water. The precipitate was filtered and dried to yield over 95% yield of 1.

Step 2: Pd/C (10%) was added to a solution of (2,4-dinitrophenyl)methylamine 1 (12.14 g, 60.9 mmol) in acetonitrile (35 mL) and triethylamine (36.4 mL). The mixture was cooled to −15° C. and then formic acid (11.1 mL) in acetonitrile (35 mL) was added. The mixture was refluxed for 3 h and then filtered. The solvent was evaporated under reduced pressure to yield the products 2 as red liquid in over 95% yield.

Step 3: Mix product 2 (1.0 eq.) and desired anhydride (1.1 eq.) in chloroform and stir for overnight. The solvent was removed under reduced pressure to yield the crude product 3 in over 95% yield.

Step 4: A solution of 3 (5.0 mmol) in EtOH (50 mL) and Pd/C (0.5 mmol) were stirred under H2 for 4 h at room temperature. EtOH was removed under reduced pressure and the residue extracted with $CH_2Cl_2$. The organic layer was washed with NaCl solution, distilled $H_2O$ and dried with $Na_2SO_4$. The solvent was evaporated and the residue was purified by flash chromatography.

Step 5: 4 (4.2 mmol) and AcOH (25 mL) was added in $H_2O$ (25 mL). The mixture was added dropwise oxirane slowly and stirred for 3 h at 10° C. Then the solution was stirred for overnight at room temperature. The mixture was poured into ice-cold $H_2O$ and distilled $H_2O$ and dried with $Na_2SO_4$. The solvent was evaporated and the residue was purified by flash chromatography.

Step 6: A solution of 5 (3.5 mmol) in $CHCl_3$ (30 mL) was added dropwise $SOCl_2$ (4.5 mmol) for 1 h while ice-cooling. This reaction solution was stirred at room temperature for 4 h. The reaction mixture was washed with $H_2O$ and the saturated $NaHCO_3$ solution. The organic phase was dried over $MgSO_4$. The solvent was evaporated and the residue was purified by flash chromatography.

Step 7: To a solution of the acid 6 (10 mmol) in diethylether (30 mL) at 0° C. ethylchloroformate (1.3 g, 12 mmol) and N-methylmorpholine (1.3 g, 13 mmol) were added and the mixture was stirred for 10 min. The solid was filtered off and the filtrate was used in the next step.

Step 8: the filtrate was added to freshly prepared hydroxylamine (0.5 g, 15 mmol) in methanol. The reaction mixture was stirred at room temperature for 15 min. The solvent was evaporated and the residue was purified by silica gel column chromatography to obtain the final product 8.

The following compounds were prepared by a slightly modified scheme of Example 6.

| Structure | m/z [M + 1]+ |
|---|---|
| 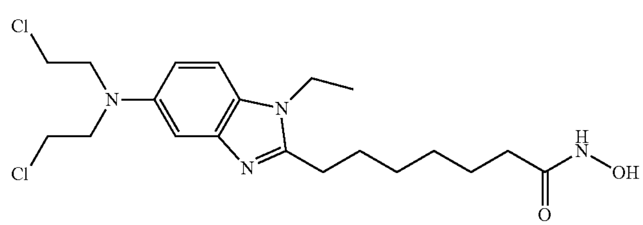 [SMILES: CCn1c(CCCCCCC(=O)NO)nc2cc(N(CCCl)CCCl)ccc21] | 429 |
| 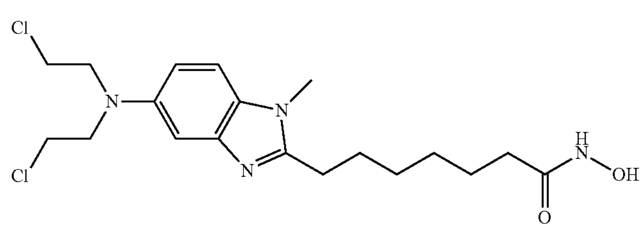 [SMILES: Cn1c(CCCCCCC(=O)NO)nc2cc(N(CCCl)CCCl)ccc21] | 415 |

Example 7

The hydroxamic acid derivatives with P represented by

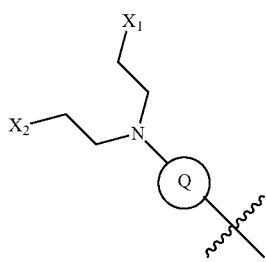

were synthesized according to the synthetic scheme below. In this example, Q is an aryl or heteroaryl substituted with at least one nitro group (e.g. 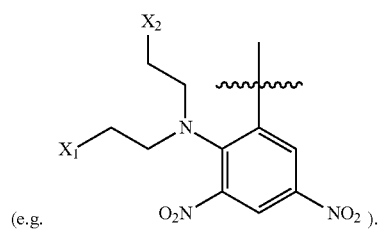 ).

diluted with saturated aqueous NaCl (40 mL) and refrigerated. The collected precipitate was purified by chromatography on silica gel, followed by recrystallization to provide 2 (yield, ~60%).

Step 2: A stirred solution of 2 (1.64 mmol) in $CH_2Cl_2$ (10 mL) containing pyridine (0.34 mL, 4.28 mmol) was treated dropwise at 0° C. with a solution of $(MsO)_2O$ (372 mg, 2.14 mmol) in $CH_2Cl_2$ (15 mL). The reaction mixture was allowed to warm temperature for 1 h, then treated with saturated aqueous $NaHCO_3$ (10 mL) and stirred for a further 0.5 h. The organic phase was washed with 1N aqueous AcOH and water, then dried and evaporated under reduced pressure. Chromatography on silia gel, followed by recrystallization to gave 3 (yield, ~70%).

Step 3: A solution of 3 (1.38 mmol) in TFA (3 mL) was stirred at room temperature for 2 h, then concentrated to small volume (not to dryness) under reduced pressure. It was then partitioned between EtOAc and water, and the organic phase was dried and evaporated under reduced pressure. Trituration of the residue with $iPr_2O$ and by recrystallization of the resulting solid from EtOAc/hexane gave 4 as a yellow solid (yield, ~88%).

Step 4,5: A suspension of 4 (0.73 mmol) in $CH_2Cl_2$ (5 mL) was treated with oxalyl chloride (0.12 mL, 1.40 mmol) and DMF (one drop), and stirred at room temperature for 1.5 h. Evaporation of the volatiles under reduced pressure below 30° C., followed by azeotroping with benzene, gave the crude acid chloride. A solution of this in DMF (1 mL) was added dropwise to a stirred solution of hydroxamic acid 5 (1.10 mmol) and DIPEA (14.2 mg, 1.10 mmol) in dioxane/THF (1:1) (2 mL) at −5° C. The mixture was stirred at 0° C. for a further 5 min, then poured into 0.12 N aqueous MsOH (15 mL) and extracted with EtAc (2*10 mL). The combined organic phase was washed with water, dried, and evaporated

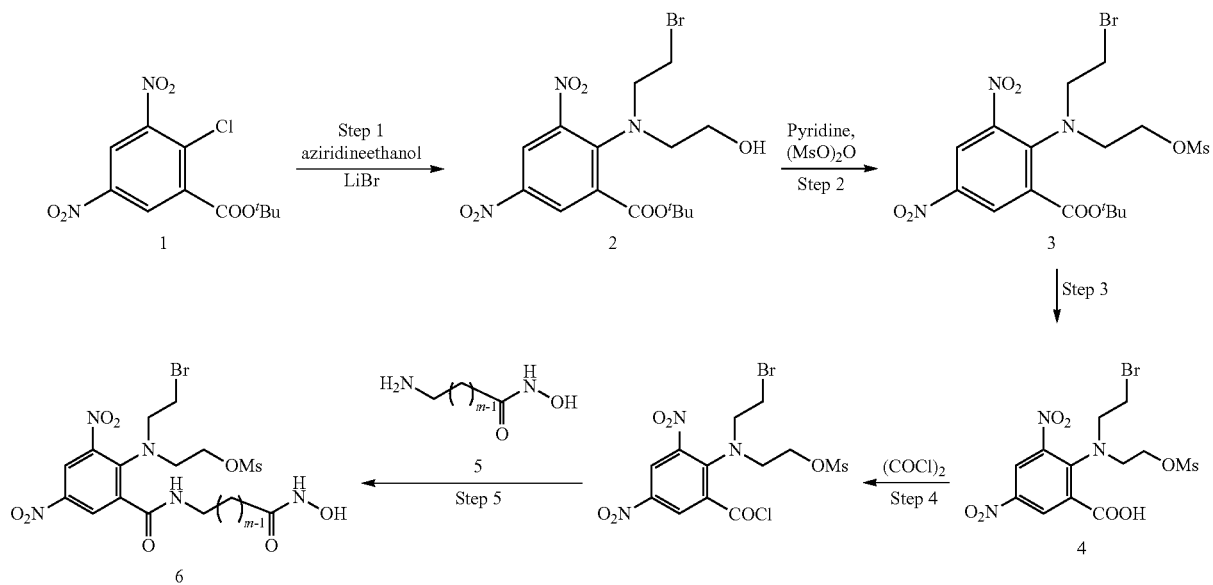

Step 1: A stirred solution of 1 (500 mg, 1.65 mmol) in DMF (1 mL) at 0° C. was treated with LiBr (1.65 mmol), followed dropwise by 1-aziridineethanol (0.33 mL, 4.12 mmol). The mixture was warmed to room temperature for 16 h, then under reduced pressure. Chromatography on siliga gel, followed by recrystallization gave the final product 6.

The following compounds were prepared by a slightly modified scheme of Example 7.

| Structure | m/z [M + 1]+ |
|---|---|
| 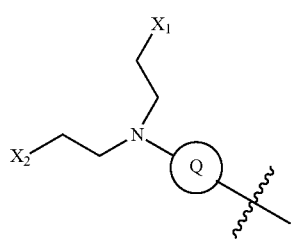 | 598 |
| 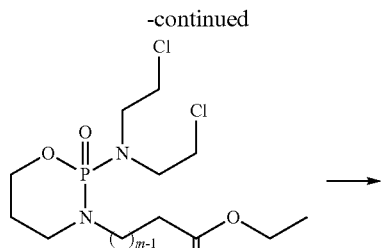 | 612 |

Example 8

The hydroxamic acid derivatives with P represented by

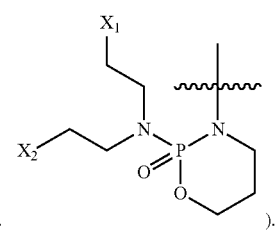

were synthesized according to the synthetic scheme below. In this example, Q is a phosphorus-containing heterocycloalkyl

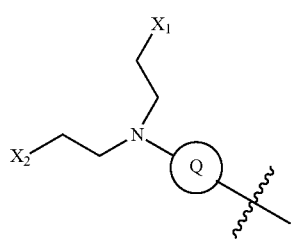

(e.g. ).

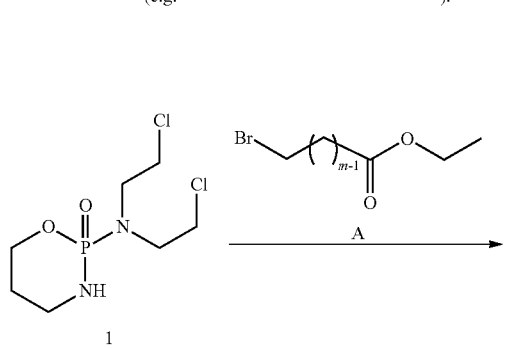

-continued

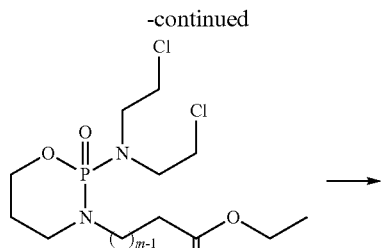

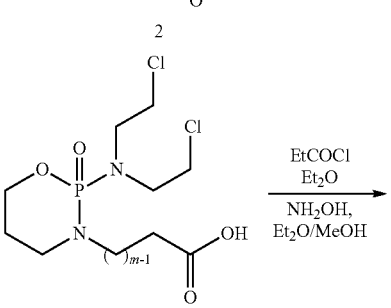

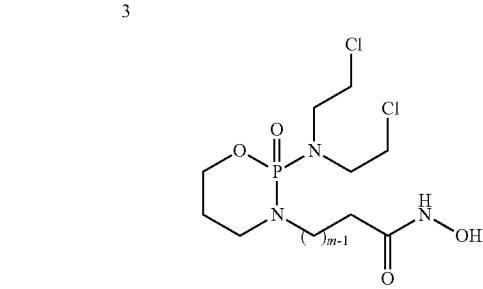

Step 1: Solid 1 (0.02 mol) was dissolved in dry DMA (48 mL). To the resulting solution were then added reagent A (0.03 mol) and BaO (3.13 g, 0.02 mol), and the mixture was stirred at 55° C. for 24 h. After being cooled to room temperature, the mixture was poured into $CH_2Cl_2$ (500 mL) and MeOH (15 mL). The solid was collected, resuspended in H₂O, filtered again, washed with MeOH, and dried in vacuo at 100° C. to obtain solid, followed by recrystallization to afford compound 2.

Step 2. A solution of 2 (15 mmol) in MeOH (200 mL) was added NaOMe (2.5 g, 45 mmol). The reaction solution was stirred at room temperature for 24 h. Then the mixture was added with the HCl solution (1.4 mol/L) to pH 6.5 and evaporated. The residue was recrystallized from ethyl acetate to afford 3.

Step 3. To a solution of the acid 3 (10 mmol) in diethylether (30 mL) at 0° C. ethylchloroformate (1.3 g, 12 mmol) and N-methylmorpholine (1.3 g, 13 mmol) were added and the mixture was stirred for 10 min. The solid was filtered off and the filtrate was added to freshly prepared hydroxylamine (0.5 g, 15 mmol) in methanol. The reaction mixture was stirred at room temperature for 15 min. The solvent was evaporated and the residue was purified by silica gel column chromatography to obtain the final product 4.

The following compounds were prepared by a slightly modified scheme of Example 8.

| Structure | m/z [M + 1]⁺ |
|---|---|
| 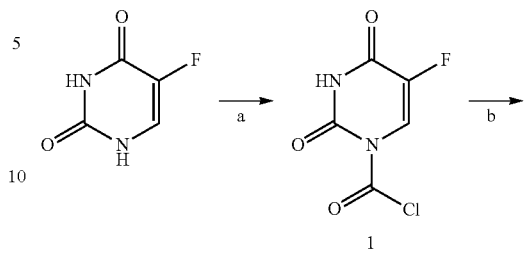 | 404 |
| 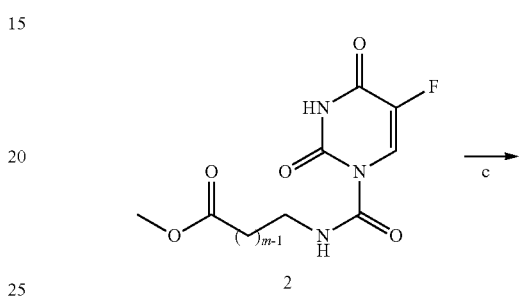 | 432 |

Example 9

The hydroxamic acid derivatives with P represented by

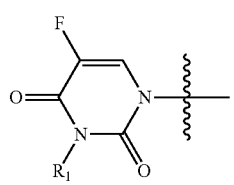

were synthesized according to the synthetic scheme below:

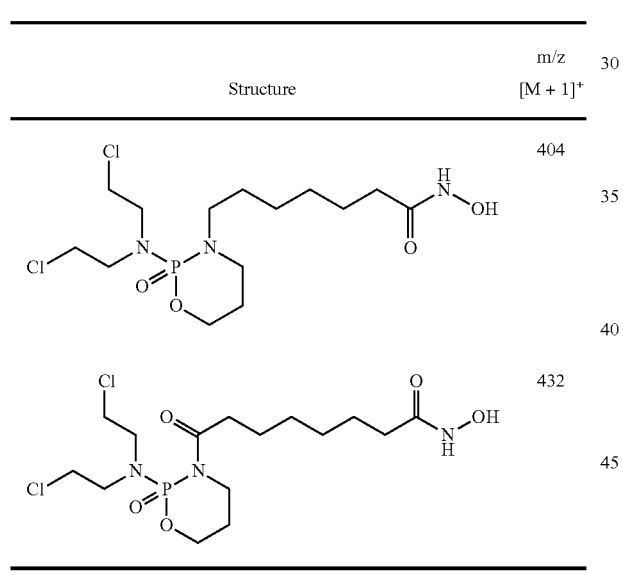

a) COCl₂, b) NH₂—(CH₂)ₙ—COOCH₃, c) NH₂OH

Step a: Into a cold (5° C.) solution containing 5-Fluorouracil (1.30 g, 0.01 mol) in 40 mL of pyridine, phosgene (2.97 g, 0.03 mol) was bubbled over a 1 hour period at 10° C. Nitrogen gas was passed through to expel the excess phosgene.

Step b: NH₂—(CH₂)ₙ—COOCH₃ (1.01 g, 0.01 mol) was then added, and the mixture was stirred for 1 h. The resulting pyridine hydrochloride was filtered off and the resulting mixture was evaporated to dryness. The residue, taken up in 50 mL of chloroform, was washed with hydrochloric acid solution. The chloroform solution was then dried (Na₂SO₄) and evaporated to afford the target.

Step c: A mixture of solution of 2 and a solution of 1.76 M NH₂OH—HCl in MeOH was stirred at room temperature overnight. The reaction mixture was neutralized by adding 1 N HCl aqueous solution (pH 7) at 0° C. The solid precipitated was collected by filtration, washed with H₂O and Et₂O, dried under vacuum, and crystallized from MeOH/CH₂Cl₂ to afford to target compound.

The following compounds were prepared by a slightly modified scheme of Example 9:

| Structure | m/z [M + 1]+ |
|---|---|
| 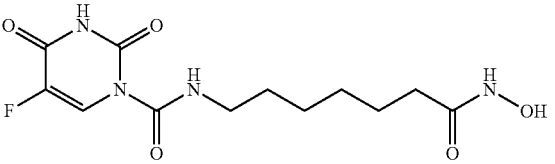 | 317 |
| 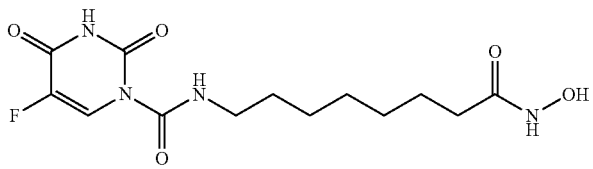 [SMILES: O=C(CCCCCCCNC(=O)n1cc(F)c(=O)[nH]c1=O)NO] | 331 |
| 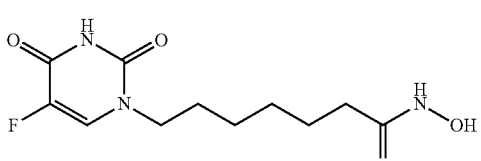 | 274 |
| 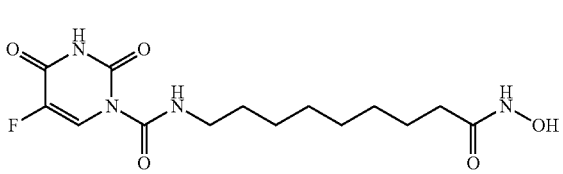 [SMILES: O=C(CCCCCCCCNC(=O)n1cc(F)c(=O)[nH]c1=O)NO] | 345 |
| 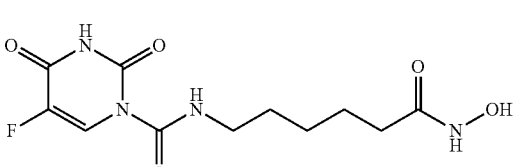 | 303 |
| 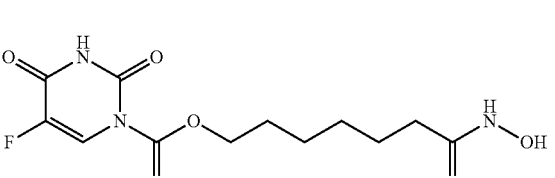 | 318 |
| 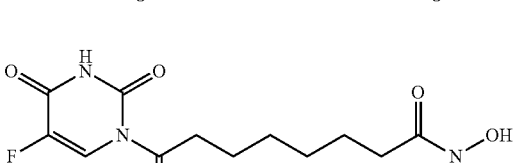 | 302 |
| 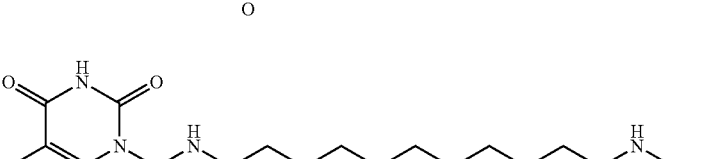 | 373 |

Example 10

The hydroxamic acid derivatives with P represented by

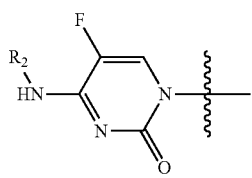

were synthesized according to the synthetic scheme below:

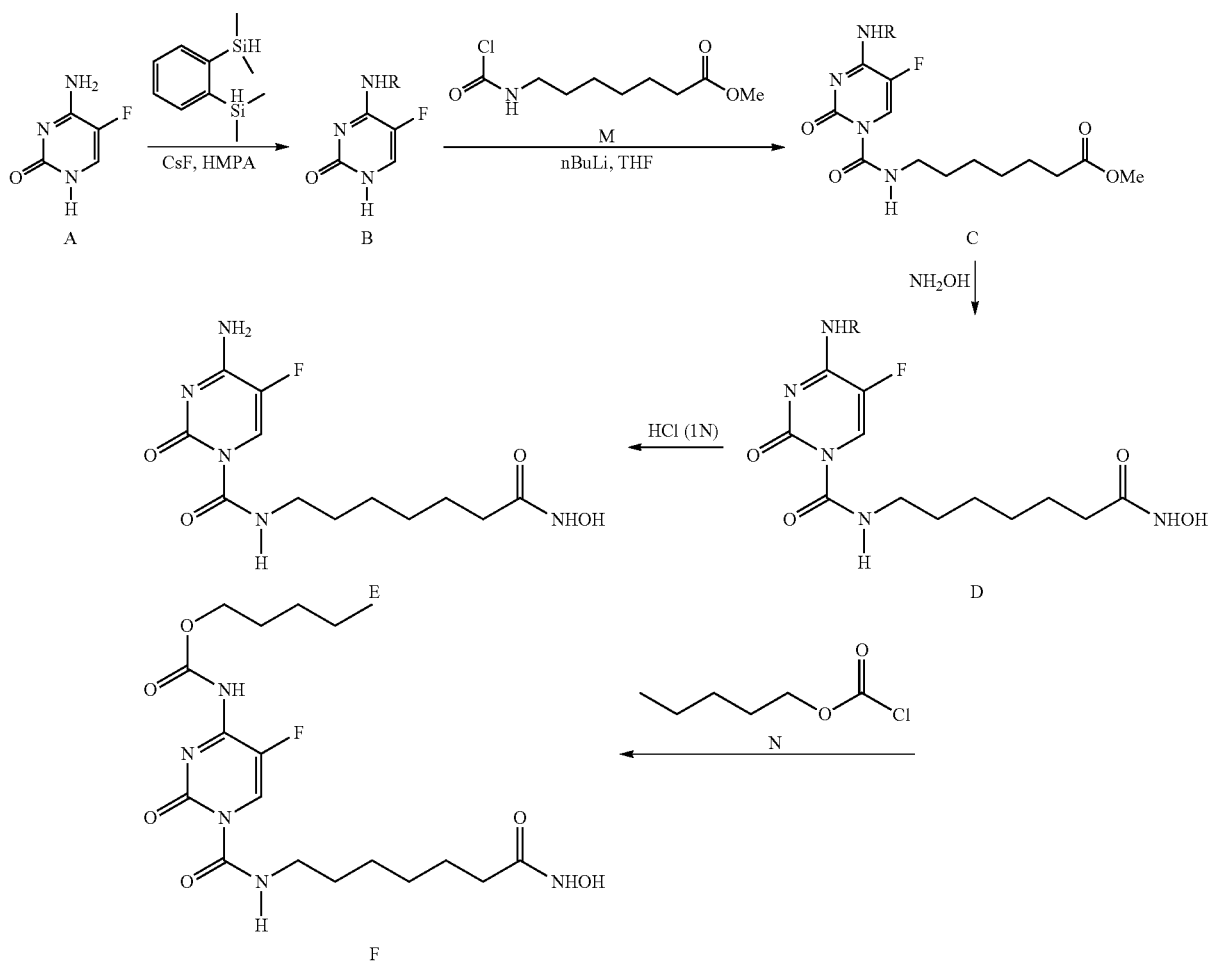

To the aniline A (30 mmol) and silane (38 mmol) in dry HMPA (10 ml) solution was added anhydrous CsF (30 mmol) and the suspension stirred at 120° C. under Ar. After cooling, the mixture is dissolved in hexane/ether (1:1, 200 ml), washed with pH 7 phosphate buffer (0.4M, 2×40 ml), and dried. Evaporation of solvent followed by recrystallization gives the product B.

B (13.5 mmol) was dissolved in THF (50 mL) and cooled to −78° C. n-BuLi (5.7 mL, 1.1 equiv. 2.5 M solution in hexanes) was added drop wise. The mixture was stirred for 30 min, then reagent M (1.05 equiv.) was added, and the mixture was allowed to warm to rt. Water was added, and the organic layer was extracted with EtOAc. The combined organic layers were dried and concentrated to give C.

To a solution of C (10 mol) in MeOH cooled in icy water were added hydroxylamine hydrochloride (55 mol) and 85% KOH (60 mol). This reaction mixture was stirred at rt for 36 h. The solvent was removed under reduced pressure, and the white residue was suspended in water. The aqueous mixture was carefully adjusted pH to 7 with 1 N HCl and extracted with CHCl₃. The organic phase was concentrated and purified by silica gel chromatography to afford product D.

D (5 mmol) was dissolved in THF (10 ml), 1 N HCl (10 mL) was added slowly. The mixture was stirred overnight. Then the aqueous mixture was carefully adjusted pH to 7 with 1 N NaOH and extracted with CHCl₃. The organic phase was concentrated and purified by silica gel chromatography to afford product E.

The mixture of compound E (1.5 mmol) in dichloromethane (75 mL) and pyridine (6 mL) was cooled to 0° C. and compound N (1.7 mmol) was added to the mixture. The mixture was stirred at 0° C. for 1 h. After evaporation, the crude product was purified by flash column chromatography to give F.

The following compounds were prepared by a slightly modified scheme of Example 10:

| Structure | m/z [M + 1]+ |
|---|---|
| 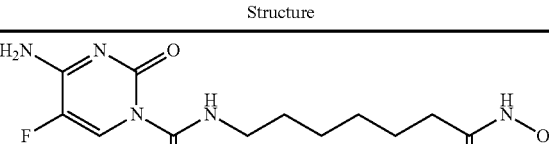 | 316 |
| 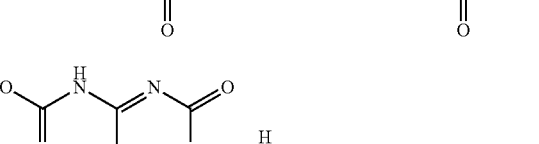 | 430 |
Example 11
The hydroxamic acid derivatives with P represented by
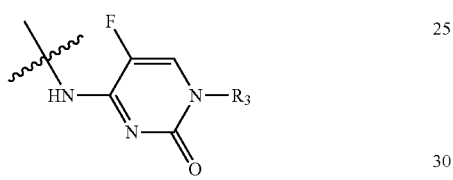
were synthesized according to the synthetic scheme below:
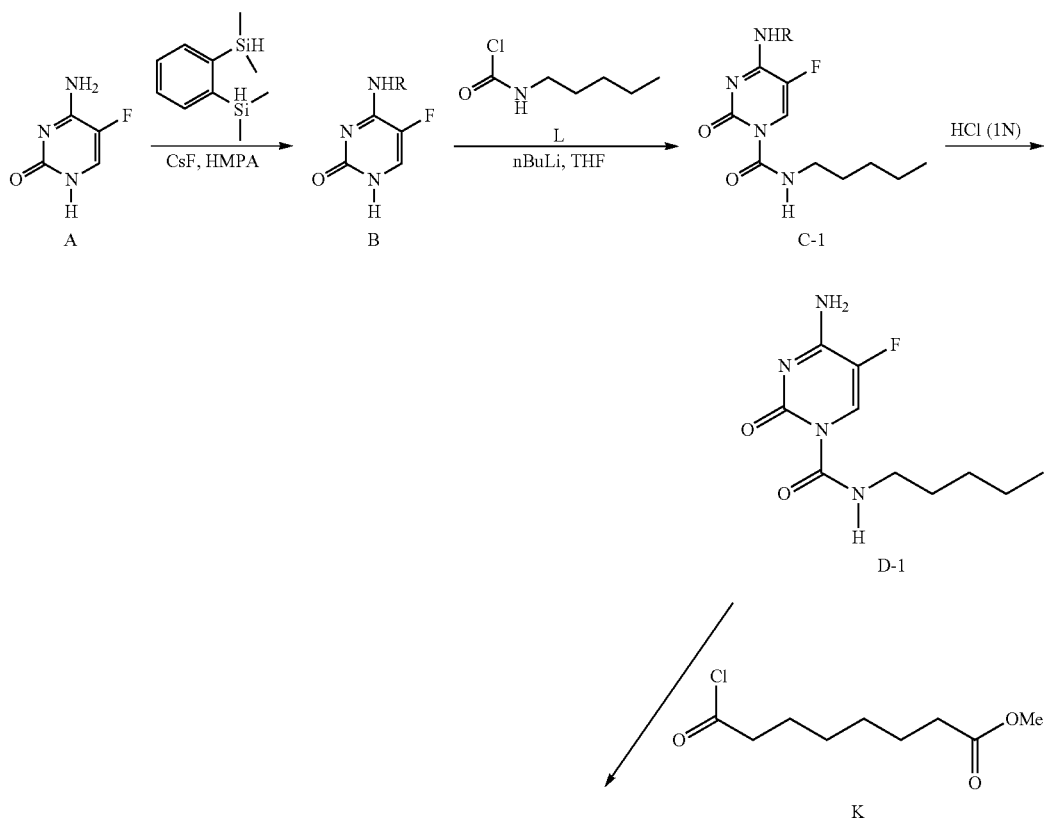

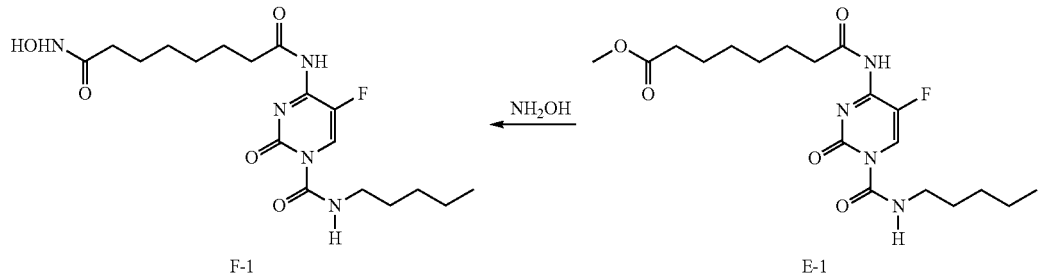

To the aniline A (30 mmol) and silane (38 mmol) in dry HMPA (10 ml) solution was added to anhydrous CsF (30 mmol) and the suspension stirred at 120° C. under Ar. After cooling, the mixture is dissolved in hexane/ether (1:1, 200 ml), washed with pH 7 phosphate buffer (0.4M, 2×40 mL), and dried. Evaporation of solvent followed by recrystallization gives the product B.

B (13.5 mmol) was dissolved in THF (50 mL) and cooled to −78° C. n-BuLi (5.7 mL, 1.1 equiv. 2.5 M solution in hexanes) was added dropwise. The mixture was stirred for 30 min, then reagent L (1.05 equiv.) was added, and the mixture was allowed to warm to rt. Water was added, and the organic layer was extracted with EtOAc. The combined organic layers were dried and concentrated to give C-1.

C-1 (5 mmol) was dissolved in THF (10 ml), 1 N HCl (10 mL) was added slowly. The mixture was stirred overnight. Then the aqueous mixture was carefully adjusted pH to 7 with 1 N NaOH and extracted with CHCl$_3$. The organic phase was concentrated and purified by silica gel chromatography to afford product D-1.

The mixture of compound D-1 (1.5 mmol) in dichloromethane (75 mL) and pyridine (6 mL) was cooled to 0° C. and compound K (1.7 mmol) was added to the mixture. The mixture was stirred at 0° C. for 1 h. After evaporation, the crude product was purified by flash column chromatography to give E-1.

To a solution of E-1 (1.0 mmol) in MeOH cooled in icy water were added hydroxylamine hydrochloride (5.5 mol) and 85% KOH (6.0 mol). This reaction mixture was stirred at rt for 36 h. The solvent was removed under reduced pressure, and the white residue was suspended in water. The aqueous mixture was carefully adjusted pH to 7 with 1 N HCl and extracted with CHCl$_3$. The organic phase was concentrated and purified by silica gel chromatography to afford product F-1.

The following compounds were prepared by a slightly modified scheme of Example 11:

| Structure | m/z [M + 1]$^+$ |
|---|---|
| 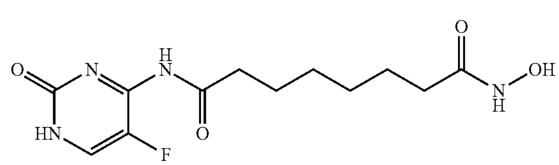 [SMILES: O=C(CCCCCCC(=O)Nc1nc(=O)[nH]cc1F)NO] | 301 |
| 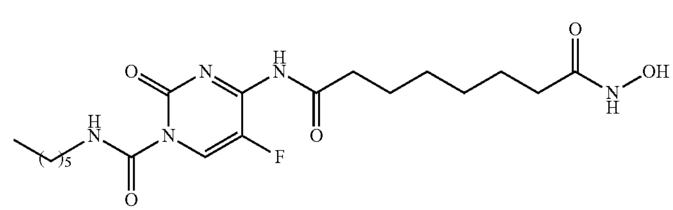 | 428 |

Example 12

The hydroxamic acid derivatives with P represented by

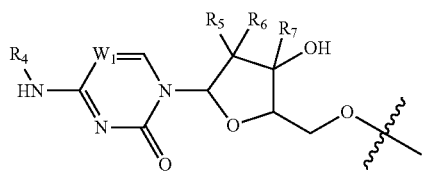

were synthesized according to the synthetic scheme below:

stirred at room temperature for 24 h. Then the mixture was added with the HCl solution (1.4 mol/L) to pH 6.5 and evaporated. The residue was recrystallized from ethyl acetate.

4 to 5: To a solution of the acid 4 (10 mmol) in diethylether (30 mL) at 0° C. ethylchloroformate (1.3 g, 12 mmol) and N-methylmorpholine (1.3 g, 13 mmol) were added and the mixture was stirred for 10 min. The solid was filtered off and the filtrate was added to freshly prepared hydroxylamine (0.5 g, 15 mmol) in methanol. The reaction mixture was stirred at room temperature for 15 min. The solvent was evaporated and the residue was purified by silica gel column chromatography to obtain the final product 5.

The following compounds were prepared by a slightly modified scheme of Example 12.

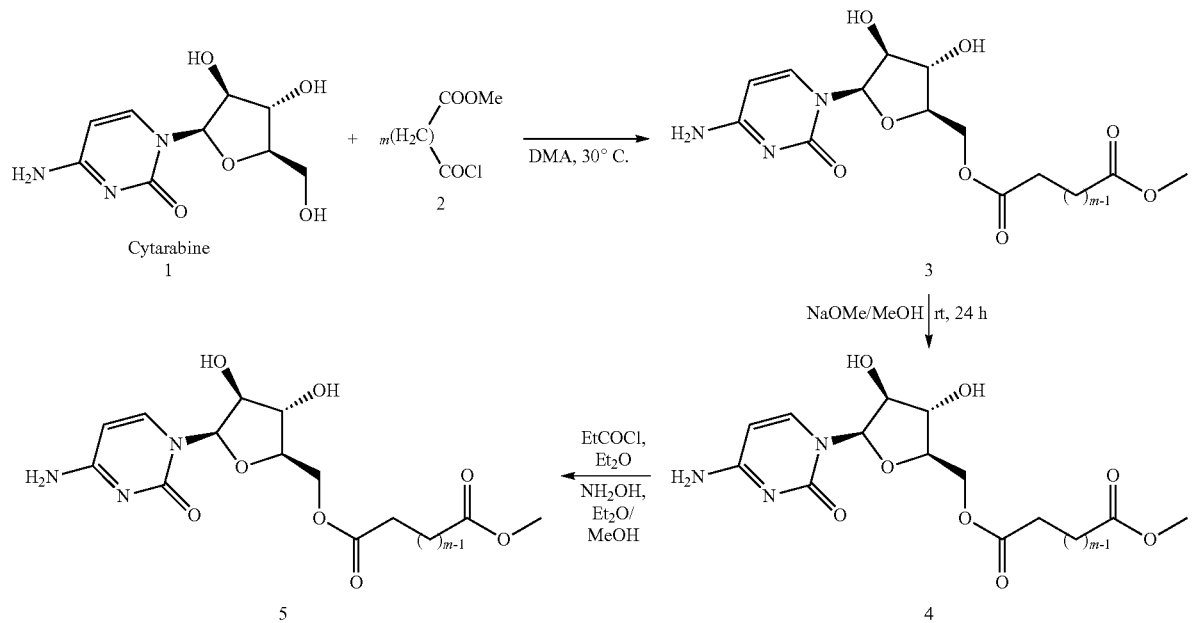

1 to 3: To a solution of Cytarabine (36 mmol) in 150 mL dimethylacetamide (DMA) was added a solution of compound 2 (42 mmol) in 50 mL DMA, and the mixture was stirred at 30 degree C. for 22 h. The solvent was evaporated at high vacuum and the residue was treated with hot ethyl acetate and filtered. The crude product was treated with 2 M NaHCO$_3$ solution, filtered off and purified by silica gel column t afford compound 3.

3 to 4: A solution of 3 (15 mmol) in MeOH (200 mL) was added NaOMe (2.5 g, 45 mmol). The reaction solution was

| Structure | m/z [M + 1]$^+$ |
|---|---|
| 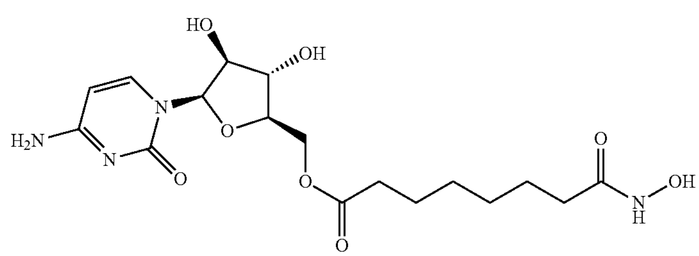 [SMILES: Nc1ccn([C@@H]2O[C@H](COC(=O)CCCCCCC(=O)NO)[C@@H](O)[C@@H]2O)c(=O)n1] | 415 |

| Structure | m/z [M + 1]+ |
|---|---|
| 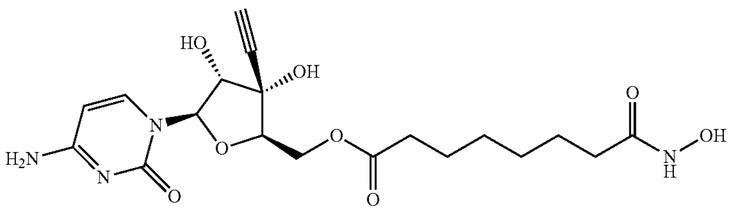 [SMILES: C#C[C@@]1(O)[C@@H](COC(=O)CCCCCCC(=O)NO)O[C@@H](n2ccc(N)nc2=O)[C@@H]1O] | 439 |
| 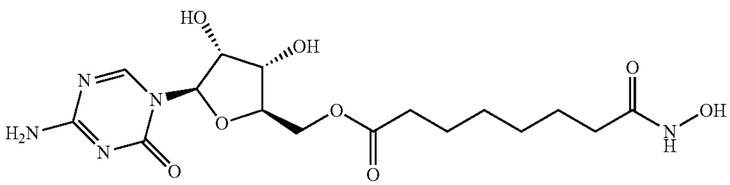 [SMILES: Nc1ncn([C@@H]2O[C@H](COC(=O)CCCCCCC(=O)NO)[C@@H](O)[C@H]2O)c(=O)n1] | 416 |
| 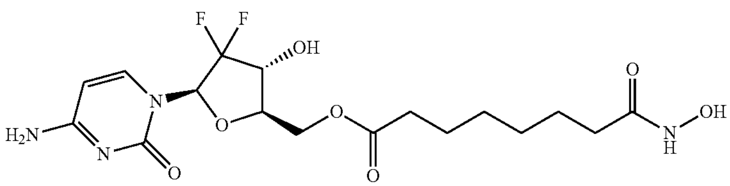 [SMILES: Nc1ccn([C@@H]2O[C@H](COC(=O)CCCCCCC(=O)NO)[C@@H](O)C2(F)F)c(=O)n1] | 435 |
| 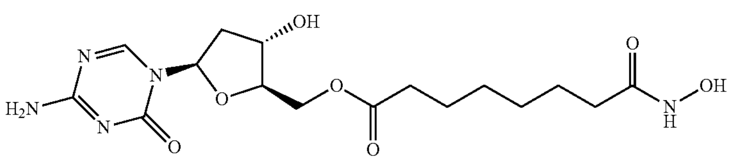 [SMILES: Nc1ncn([C@H]2C[C@H](O)[C@@H](COC(=O)CCCCCCC(=O)NO)O2)c(=O)n1] | 400 |
| 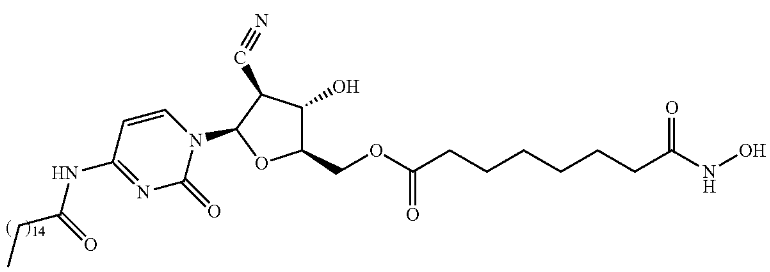 | 662 |
Example 13
The hydroxamic acid derivatives with P represented by
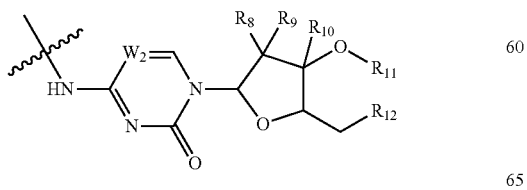
were synthesized according to the synthetic scheme below:

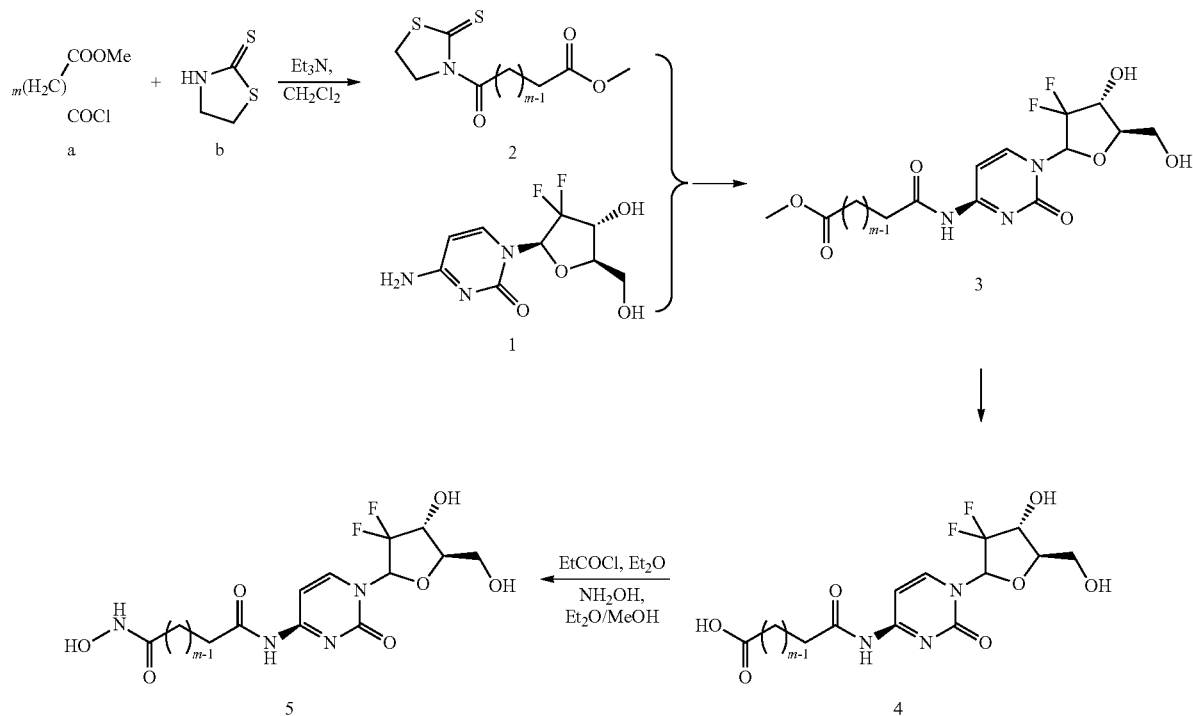

a+b to 2: To a solution of b (1 eq) in CH₂Cl₂ added 1.1 eq. Et₃N at room temperature. To the mixture cooled to 0° C., compound a was added slowly. After stirring for 10 h at room temperature, the reaction was quenched with water. After evaporation, the crude product was purified by flash column chromatography to give the desired compound 2.

1 to 3: To a solution of Gemcitabine (36 mmol) in 150 mL pyridine was added compound 2 (12 g, 40 mmol) and the reaction mixture was stirred at ambient temperature for 2.5 hours. The solvent was evaporated at high vacuum and the crude product was purified on a column of silica gel with 15% methanol in chloroform as the eluent system. Product containing fractions were evaporated, and the residue was treated with ether/hexan in an ultra-sound bath. The crystalline material was dried to give compound 3.

3 to 4: A solution of 3 (15 mmol) in MeOH (200 mL) was added NaOMe (2.5 g, 45 mmol). The reaction solution was stirred at rt for 24 h. Then the mixture was added with the HCl solution (1.4 mol/L) to pH 6.5 and evaporated. The residue was recrystallized from ethyl acetate.

4 to 5: To a solution of the acid 4 (10 mmol) in diethylether (30 mL) at 0° C. ethylchloroformate (1.3 g, 12 mmol) and N-methylmorpholine (1.3 g, 13 mmol) were added and the mixture was stirred for 10 min. The solid was filtered off and the filtrate was added to freshly prepared hydroxylamine (0.5 g, 15 mmol) in methanol. The reaction mixture was stirred at room temperature for 15 min. The solvent was evaporated and the residue was purified by silica gel column chromatography to obtain the final product 5.

The following compounds were prepared by a slightly modified scheme of Example 13:

| Structure | m/z [M + 1]⁺ |
|---|---|
| 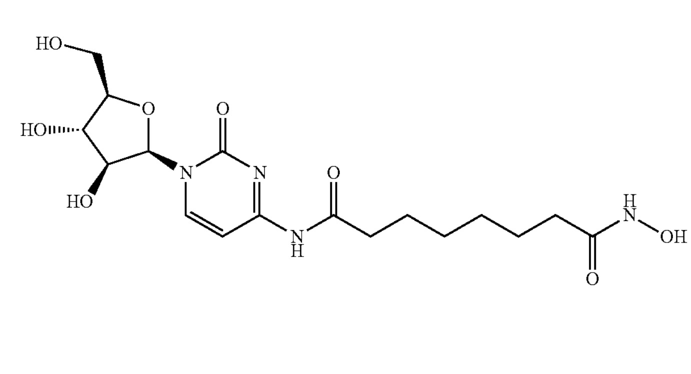 [SMILES: O=C(CCCCCCC(=O)Nc1ccn([C@@H]2O[C@H](CO)[C@@H](O)[C@@H]2O)c(=O)n1)NO] | 415 |

-continued
| Structure | m/z [M + 1]+ |
|---|---|
| 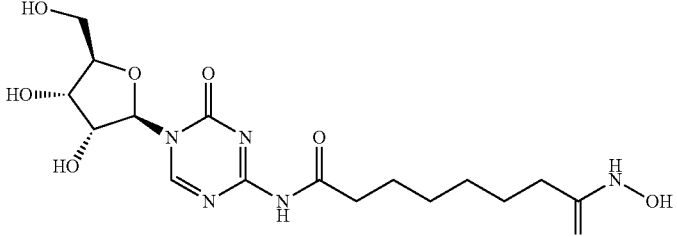 | 416 |
| 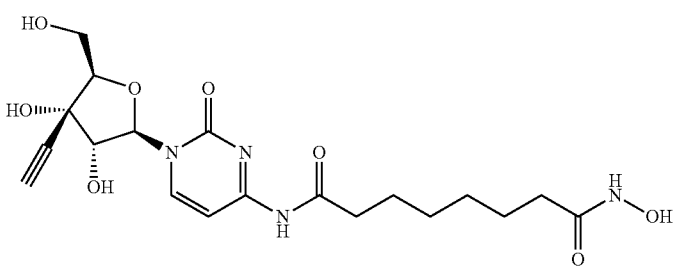 [SMILES: C#C[C@@]1(O)[C@@H](CO)O[C@@H](n2ccc(NC(=O)CCCCCCC(=O)NO)nc2=O)[C@@H]1O] | 439 |
| 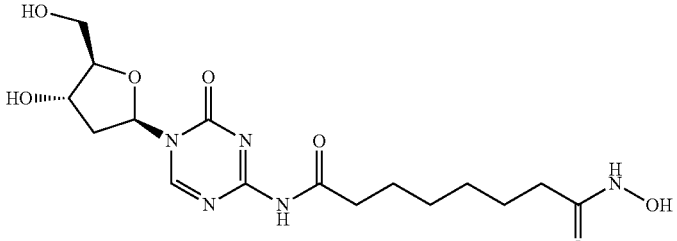 | 400 |
| 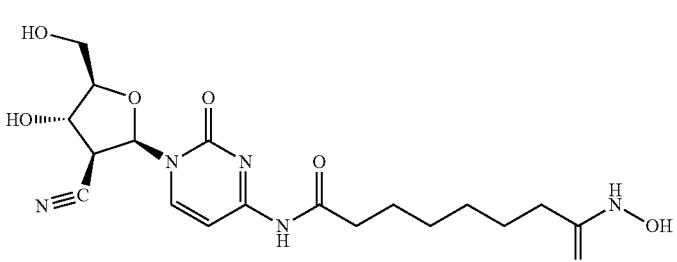 | 424 |
| 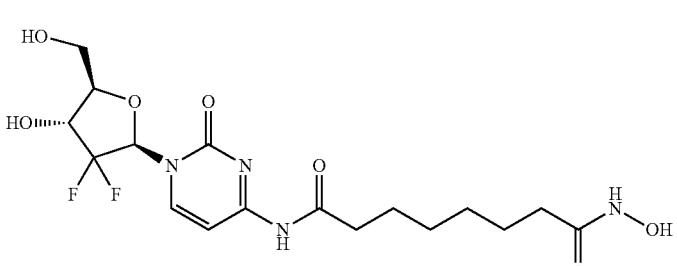 | 435 |

Example 14

The hydroxamic acid derivatives with P represented by

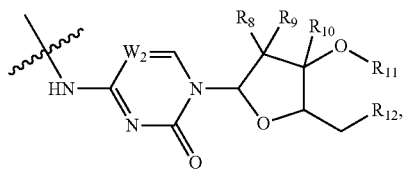

wherein $W_2$ is CF, $R_8$, $R_{10}$, and $R_{12}$ are H were synthesized according to the synthetic scheme below.

2 to 3: A mixture of D-ribose (2, 19.25 g, 128.33 mmol commercially available) in acetone (75 mL), methanol (75 mL) and Concentrated HCl (2 mL) was refluxed for 2 h. The reaction solution was diluted by $H_2O$ (200 mL) and extracted with $CHCl_3$ (3×200 mL). The organic phase was dried over $Na_2SO_4$, evaporated and dried under vacuum to give a thick yellow oil 3 (20.50 g, 78%), which was used for the next reaction without further purification.

3 to 4: Compound 3 (5.11 g, 25.05 mmol) was dissolved in pyridine (30 mL). Tosyl chloride (6.50 g, 34.09 mmol) was added to the solution. The mixture was stirred at room temperature for 18 h. The solvent was removed by evaporation under vacuum and the crude product was purified with flash column chromatography (1:4 EtOAc/hexane) to give a vacuum dried product as a white solid 4 (7.50 g, 84%).

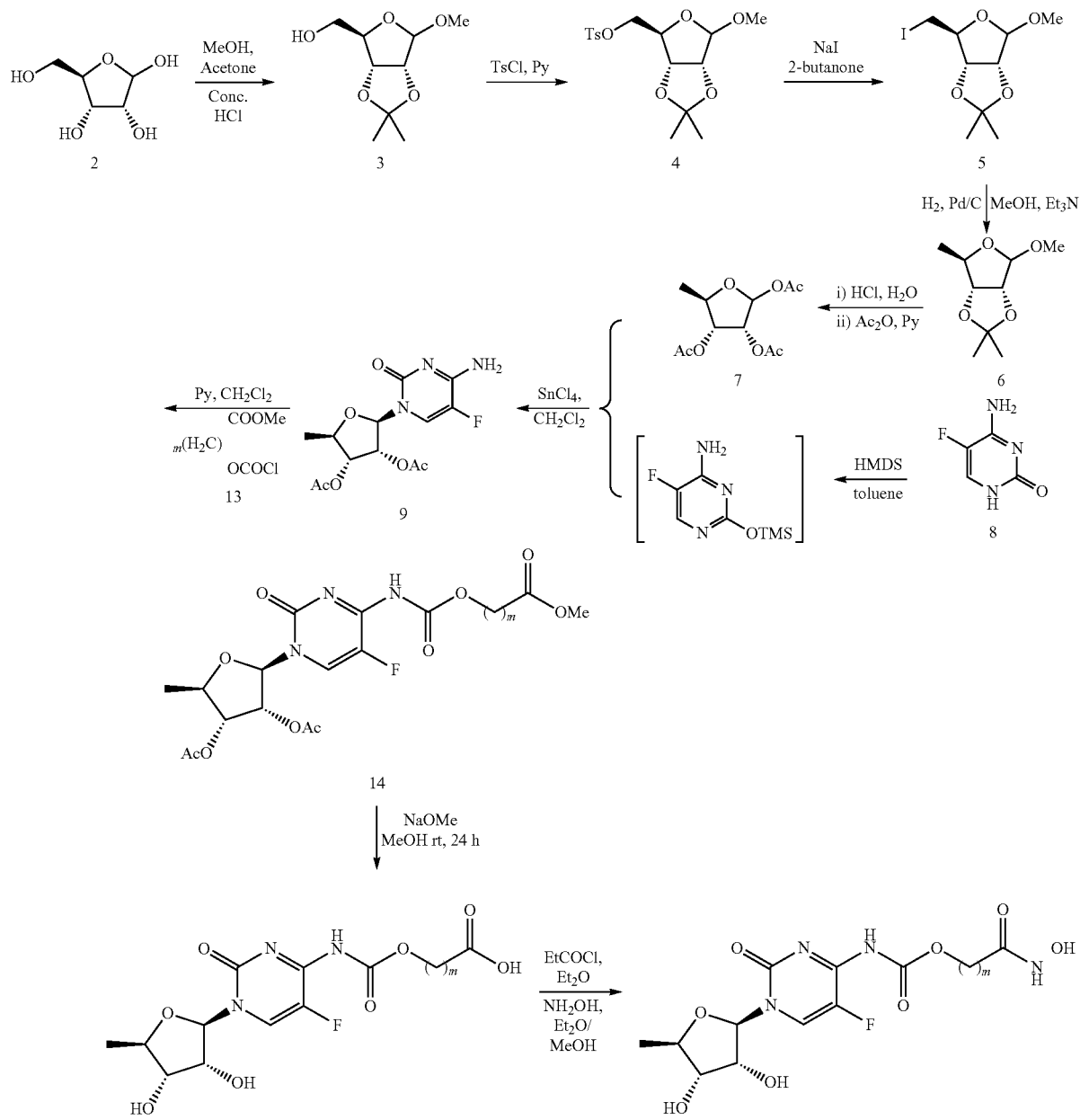

4 to 5: A mixture of compound 4 (4.40 g, 12.30 mmol), NaI (5.03 g, 33.53 mmol) in 2-butanone (50 mL) was refluxed for 24 h. The solvent was evaporated and the residue was diluted in Et$_2$O. Filtration gave a solution, which was evaporated and dried under vacuum to give light yellow oil 5 (3.75 g, 97%)

5 to 6: Compound 5 (3.67 g, 11.69 mmol) was dissolved in methanol (100 mL) and Et$_3$N (3.0 mL). 10% Pd/C (0.40 g) was added to the solution. The mixture was stirred at room temperature under H$_2$ for 24 h. The solution was filtrated though Celite. The solvent was removed by evaporation and dried under vacuum to give light yellow oil 6 (2.10 g, 95%)

6 to 7: A solution of the compound 6 (2.11 g, 11.22 mmol) in 1N HCl (1.5 mL) and H$_2$O (35 mL) was refluxed for 2 h. The solvent was removed and the residue was dissolved in acetic anhydride (5.0 mL) and pyridine (50 mL). The reaction mixture was stirred at room temperature for 24 h. The solvent was removed and the residue was diluted by CH$_2$Cl$_2$. The solution was washed with H$_2$O. The organic phase was dried over Na$_2$SO$_4$ and the solvent was removed by evaporation to give a colorless oil 7 (2.89 g, 99%). It was purified by recrystallization in diisopropyl ether to give a vacuum dried product as a white solid 7.

7+8 to 9: The mixture of 5-fluorocytosine (8, 0.30 g, 2.32 mmol commercially available) in toluene (1.5 mL) and HMDS (0.38 g, 2.32 mmol) was refluxed for 3 h. The solvent was removed by evaporation and the residue was dissolved in dichloromethane (5 mL). Compound 7 (0.66 g, 2.54 mmol) and SnCl$_4$ (0.72 g, 0.32 mmol) were added to the solution at 0° C. The mixture was stirred at 0° C. for 2 h. NaHCO$_3$ (1.2 g) and H$_2$O (0.5 mL) was added to the mixture. After the mixture was stirred at room temperature for 3 h, filtration gave a solution, which was washed by 1N NaHCO$_3$. The solvent was removed by evaporation to give a crude product, which was purified by flash column chromatography (1:20 MeOH/ EtOAc) to give a vacuum dried product as a white solid 9 (0.60 g, 78%).

9+13 to 14: The mixture of compound 9 (1.5 mmol) in dichloromethane (75 mL) and pyridine (6 mL) was cooled to 0° C. and compound 13 (2.2 mmol) was added to the mixture. The mixture was stirred at 0° C. for 1 h. After evaporation, the crude product was purified by flash column chromatography to give a vacuum dried product as a light yellow solid 14.

14 to 15: A solution of 14 (1 mmol) in MeOH (15 mL) was added NaOMe (0.25 g, 4.5 mmol). The reaction solution was stirred at room temperature for 24 h. Then the mixture was added with the HCl solution (1.4 mol/L) to pH 6.5 and evaporated. The residue was recrystallized from ethyl acetate.

15 to 1: To a solution of the acid 15 (1 mmol) in diethylether (5 mL) at 0° C. ethylchloroformate (1.2 mmol) and N-methylmorpholine (1.3 mmol) were added and the mixture was stirred for 10 min. The solid was filtered off and the filtrate was added to freshly prepared hydroxylamine (1.5 mmol) in methanol. The reaction mixture was stirred at room temperature for 15 min. The solvent was evaporated and the residue was purified by silica gel column chromatography to obtain the final product 1.

The following compounds were prepared by a slightly modified scheme of Example 14:

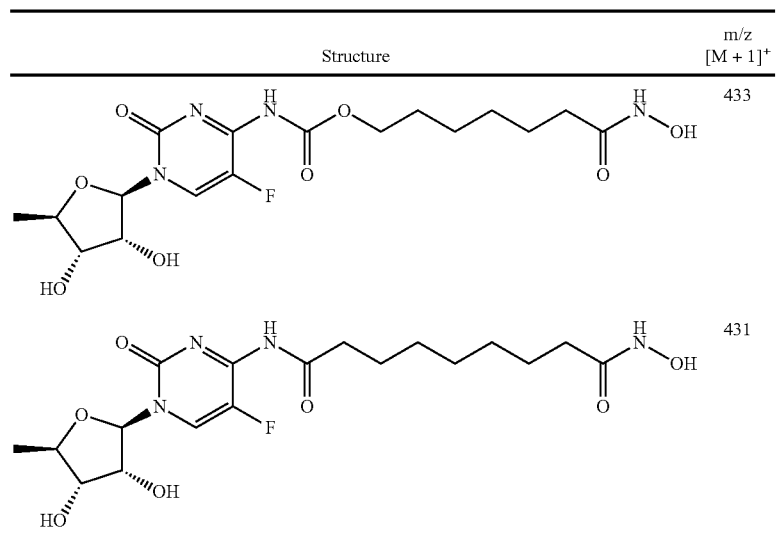

Biological Assays:

(a) Inhibition of Histone Deacetylase Enzymatic Activity

Hydroxamic acid is a well know metal-chelating agent, especially for Zn atom. The hydroxamic acid moiety has been demonstrated as the key structural element in many highly potent and selective inhibitors against a variety of metalloenzymes, such as matrix metalloproteinases (MMP), tumor necrosis factor-α converting enzyme (TACE), Histone Deacetylase (HDAC), Peptidyl deformylase (PDF), A Disintegrin And Metalloproteinase (ADAM), UDP-3-O—[R-3-hydroxymyristoyl]-GlcNAc deacetylase, Clostridium Histolytium Collagenase (ChC), Procollagen C-Proteinase (PCP), and Aggrecanase. Many of these metalloenzymes are well known important disease target, such as HDAC and MMP. All hydroxamic acid compounds exemplified in the application have been tested against one or multiple metalloenzymes. The following protocol is used to assay the compounds of the invention against the HDAC enzymes.

The buffer used in this assay is 25 mM HEPES, pH 8.0, 137 mM NaCl, 2.7 mM KCl, 1 mM MgCl$_2$ and the subtrate is Boc-Lys(Ac)-AMC (Fluor-de-Lys substrate, Cat. # KI-104) in a 50 mM stock solution in DMSO. The enzyme stock solution is 4 µg/mL in buffer. The compounds are pre-incubated (2 µl in DMSO diluted to 13 µl in buffer for transfer to assay plate) with enzyme (20 µl of 4 µg/ml) for 10 minutes at room temperature (35 µl pre-incubation volume). The mixture is pre-incubated for 5 minutes at room temperature. The reaction is started by bringing the temperature to 37° C. and adding 16 μl substrate. Total reaction volume is 50 μl. The reaction is stopped after 20 minutes by addition of 50 μl developer, prepared as directed by Biomol (Fluor-de-Lys developer, Cat. # KI-105). A plate is incubated in the dark for 10 minutes at room temperature before reading ($\gamma_{EX}$=360 nm, $\gamma_{Em}$=470 nm, Cutoff filter at 435 nm). Such assays, carried out with a range of doses of test compounds, allow the determination of an approximate IC50 value. The HDAC inhibitor SAHA was used as reference compound. All compounds exemplified in the application show inhibitory activity against one or more of HDAC-1, HDAC-2, HDAC-3, HDAC-4, HDAC-5, HDAC-6, HDAC-7, HDAC-8, HD AC-9, HDAC-10, and HDAC-11. Although the inhibitory properties of the compounds of the present invention vary with structural change as expected, the activity generally exhibited by these agents is in the range of IC50=1-1000 nM.

For example, the following is the structure of DNA alkylating drug Bendamustine and its corresponding hydroxamic acid derivative CY190602. The following table lists the HDAC IC50 values of the hydroxamic acid derivative CY190602.

Bendamustine
The Parental DNA Alkylating Drug

| HDAC subtype | CY190602 (nM) |
|---|---|
| HDAC-1 | 17 |
| HDAC-2 | 9 |
| HDAC-3 | 25 |
| HDAC-6 | 6 |
| HDAC-8 | 107 |
| HDAC-10 | 72 |

CY190602
Hydroxamic Derivative of Bendamustine

| SAHA (nM) | Bendamustine |
|---|---|
| 32 | No activity |
| 16 | No activity |
| 50 | No activity |
| 17 | No activity |
| 103 | No activity |
| 63 | No activity |

(b) In Vitro Anti-Proliferation Assay:

Cell antiproliferation was assayed by PerkinElmer ATPlite™ luminescence assay System. The cancer cell lines were plated at 10 k cells per well in Costar 96-well plates with different concentration of compounds for 72 hours with 5% FBS. After that, one lyophilized substrate solution vial was reconstituted by adding 5 mL of substrate buffer solution and was agitated gently until the solution is homogeneous. 50 μL of mammalian cell lysis solution was added to 100 μL of cell suspension per well of a microplate and the plate was shaken for five minutes in an orbital shaker at 700 rpm. This procedure will lyses the cells and stabilizes the ATP. Next, 50 μL substrate solution was added to the wells and microplate was shaken for five minutes in an orbital shaker at 700 rpm. Finally the luminescence was measured by a PerkinElmer TopCount® Microplate Scintillation Counter. Such assays, carried out with a range of doses of test compounds, allow the determination of an approximate IC50 value for the in vitro cell antiproliferation assay of cancer cell lines. Although the inhibitory properties of the compounds of the present invention vary with structural change as expected, the activity generally exhibited by these agents is in the range of IC50=0.01-200 uM.

For example, the following table lists the IC50 values of the Bendamustien and its hydroxamic acid derivative CY190602 in the cell anti-proliferative assays. The present inventors have surprisingly found that, in many cancer cell lines such as RPMI8226, MM1R, and MM1S, the anti-tumor activities of the hydroxamic acid derivative are significantly better than the parental drug Bendamustine.

| Cell line | RPMI8226(uM) | MM1S(uM) | MM1R(uM) |
|---|---|---|---|
| Bendamustine | 400 | 119 | 100 |
| CY190602 | 4.16 | 1.6 | 2.66 |
| Ratio | ~X 100 | ~X 70 | ~X 35 |

What is claimed is:

1. A compound of Formula I, or a pharmaceutically acceptable salt thereof:

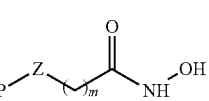

Formula I wherein

Z is deleted, C($R_a R_b$), O, S, C(O), N($R_a$), $SO_2$, OC(O), C(O)O, $OSO_2$, S($O_2$)O, C(O)S, SC(O), C(O)C(O), C(O)N($R_a$), N($R_a$)C(O), S($O_2$)N($R_a$), N($R_a$)S($O_2$), OC(O)N(R$_a$), N(R$_a$)C(O)O, N(R$_a$)C(O)S, or N(R$_a$)C(O)N(R$_b$), in which each of R$_a$ and R$_b$, independently, is H, alkyl, alkenyl, or alkynyl;

m is 5, 6, 7, 8, 9, 10, 11, 12, 13, 14, 15, or 16; and P is

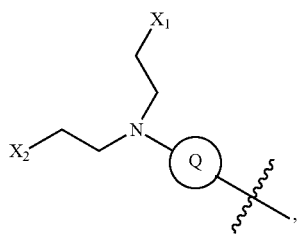

in which each of X$_1$ and X$_2$ independently, is halo or OSO$_2$R$_c$, in which R$_c$ is alkyl, alkenyl, or alkynyl; Q is cycloalkyl, heterocycloalkyl, cycloalkenyl, heterocycloalkenyl, aryl, or heteroaryl, each of which, independently, is optionally substituted with alkyl, alkenyl, alkynyl, cycloalkyl, heterocycloalkyl, cycloalkenyl, heterocycloalkenyl, aryl, heteroaryl, halo, nitro, oxo, —C≡NH, cyano, OR$_d$, OC(O)R$_d$, OC(O)OR$_d$, OC(O)SR$_d$, SR$_d$, C(O)R$_d$, C(O)OR$_d$, C(O)SR$_d$, C(O)NR$_e$R$_f$, SOR$_d$, SO$_2$R$_d$, NR$_e$R$_f$, or N(R$_e$)C(O)R$_f$, in which each of R$_d$, R$_e$, and R$_f$ independently, is H, alkyl, alkenyl, alkynyl, cycloalkyl, heterocycloalkyl, aryl, heteroaryl, halo, cyano, nitro, hydroxy, or alkoxy.

2. The compound or salt of claim 1, wherein Z is deleted, CH$_2$, O, CO, NH, SO$_2$, OC(O), C(O)O, C(O)S, NHC(O), C(O)NH, OC(O)NH, NHC(O)O, or NHC(O)S; m is 5, 6, 7, or 8.

3. The compound or salt of claim 2, wherein Q is an aryl or heteroaryl.

4. The compound or salt of claim 3, wherein Q is a 9-10 membered aryl or heteroaryl.

5. The compound or salt of claim 4, wherein P is

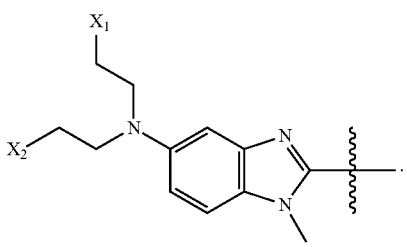

6. The compound or salt of claim 1, wherein the compound is

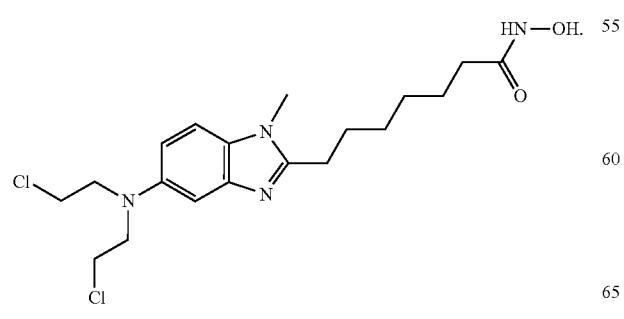

7. A pharmaceutical composition comprising a compound or salt of claim 1 and a pharmaceutically acceptable carrier.

8. A method of improving or relieving multiple myeloma, the method comprising administering to a subject in need thereof an effective amount of a compound or salt of claim 1.

9. A method of improving or relieving multiple myeloma, the method comprising administering to a subject in need thereof an effective amount of a compound or salt of claim 5.

10. A method of improving or relieving multiple myeloma, the method comprising administering to a subject in need thereof an effective amount of a compound or salt of claim 6.

11. The compound or salt of claim 1, wherein the compound is

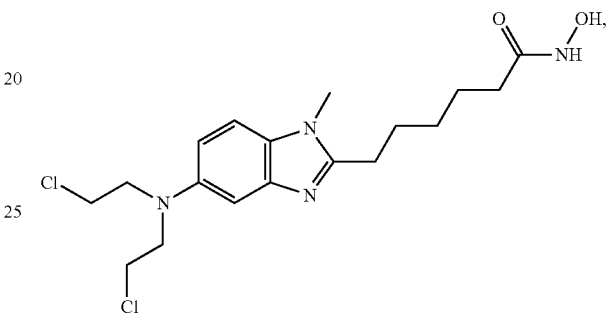

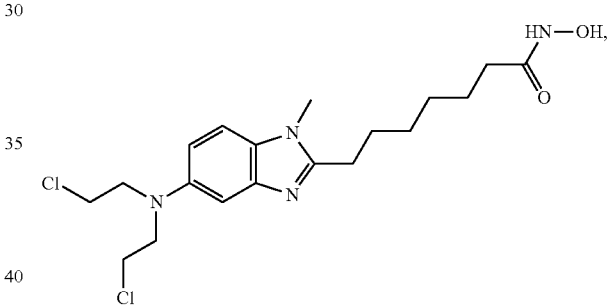

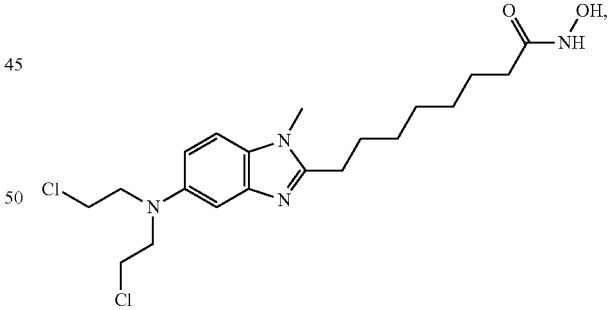

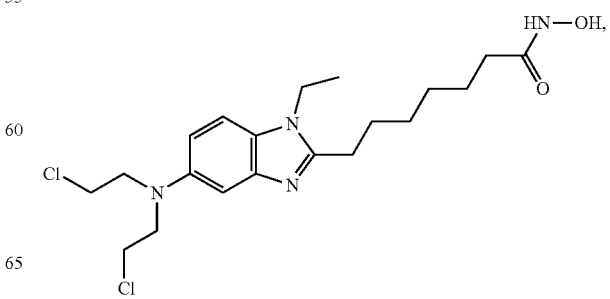

-continued

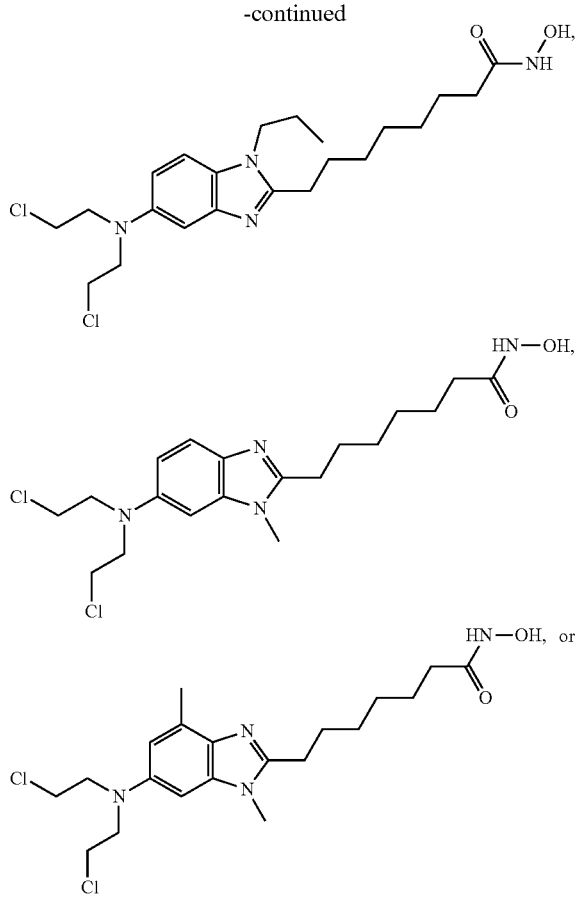

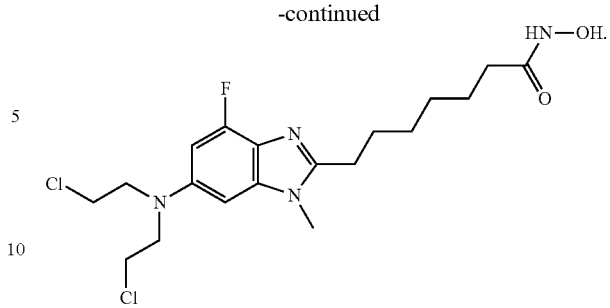

12. A method of improving or relieving multiple myeloma, the method comprising administering to a subject in need thereof an effective amount of a compound or salt of claim 11.

13. A pharmaceutical composition comprising a compound or salt of claim 5 and a pharmaceutically acceptable carrier.

14. A pharmaceutical composition comprising a compound or salt of claim 6 and a pharmaceutically acceptable carrier.

15. A pharmaceutical composition comprising a compound or salt of claim 11 and a pharmaceutically acceptable carrier.

16. The compound or salt of claim 6, wherein the salt is chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, or acetate.

\* \* \* \* \*